(12) United States Patent
Dothie et al.

(10) Patent No.: US 11,198,130 B2
(45) Date of Patent: Dec. 14, 2021

(54) EWOD SYSTEM AND METHODS TO INCREASE DYNAMIC RANGE FOR DIGITAL NUCLEIC ACID AMPLIFICATION

(71) Applicant: Sharp Life Science (EU) Limited, Oxford (GB)

(72) Inventors: Pamela Ann Dothie, Oxford (GB); Sally Anderson, Oxford (GB); Philip Mark Shryane Roberts, Oxford (GB)

(73) Assignee: Sharp Life Science (EU) Limited, Oxford (GB)

( * ) Notice: Subject to any disclaimer, the term of this patent is extended or adjusted under 35 U.S.C. 154(b) by 382 days.

(21) Appl. No.: 16/014,006

(22) Filed: Jun. 21, 2018

(65) Prior Publication Data
US 2019/0388894 A1  Dec. 26, 2019

(51) Int. Cl.
*B01L 3/00* (2006.01)
*B01F 13/00* (2006.01)

(52) U.S. Cl.
CPC .... *B01L 3/502792* (2013.01); *B01F 13/0071* (2013.01); *B01F 13/0084* (2013.01); *B01L 3/50273* (2013.01); *B01L 3/502746* (2013.01); *B01L 2400/0427* (2013.01)

(58) Field of Classification Search
CPC ....... B01L 3/502792; B01L 2400/0427; C12Q 1/6851
See application file for complete search history.

(56) References Cited

U.S. PATENT DOCUMENTS

| | | | |
|---|---|---|---|
| 6,565,727 B1 | 5/2003 | Shenderov | |
| 6,911,132 B2 | 6/2005 | Pamula et al. | |
| 7,163,612 B2 | 1/2007 | Sterling et al. | |
| 8,653,832 B2 | 2/2014 | Hadwen et al. | |
| 9,091,649 B2 | 7/2015 | Pollack et al. | |
| 9,539,573 B1 | 1/2017 | Hadwen et al. | |
| 2013/0288254 A1 | 10/2013 | Pollack et al. | |
| 2016/0310949 A1* | 10/2016 | Kwang | B01L 3/502792 |
| 2016/0375437 A1* | 12/2016 | Hadwen | B01F 13/0071 |
| | | | 204/451 |

FOREIGN PATENT DOCUMENTS

| | | |
|---|---|---|
| EP | 2570188 | 3/2013 |
| WO | WO 2014043581 | 3/2014 |
| WO | WO 2015063767 | 5/2015 |
| WO | WO 2016170109 | 10/2016 |

OTHER PUBLICATIONS

Lievens, Measuring Digital PCR Quality: Performance Parameters and Their Optimization, PLoS One, 11 (5):e0153317, doi: 10/1371/journal.pone.0153317, 2016. (Year: 2016).*
Korenkova, Pre-amplification in the context of high-throughput qPCR gene expression experiment, BMC Molecular Biology, 16:5, pp. 1-10, 2015. (Year: 2015).*
"Comparison of fluorescence-based quantitation with UV absorbance measurements Qubit® fluorometric quantitation vs. spectrophotometer measurements", 4 pages, lifetechnologies.com/qubit, 2014.
"Digital microfluidics: is a true lab-on-a-chip possible?", R.B. Fair, Microfluid Nanofluid (2007) 3:245-281).
"Digital microfluidics: is a true lab-on-a-chip possible?", R.B. Fair, Microfluid Nanofluid (2007) 3:245-281), XP019496789.

* cited by examiner

*Primary Examiner* — Samuel C Woolwine
*Assistant Examiner* — Carolyn L Greene
(74) *Attorney, Agent, or Firm* — Renner, Otto, Boisselle & Sklar, LLP

(57) ABSTRACT

A method of digital quantification of a species in an EWOD device includes inputting a sample volume and a diluent volume into the EWOD device; performing an electrowetting operation to generate a first sample droplet from the sample volume; performing an amplification process on the first sample droplet and measuring a turn-on value for the sample droplet; comparing the measured turn-on value to a target turn-on value for digital quantification; calculating a dilution factor based on the comparison of the measured and target turn-on values; performing an electrowetting operation to extract a second sample droplet from the sample volume; performing an electrowetting operation to dilute the second sample droplet with the diluent volume by the dilution factor to form a diluted second sample droplet; and performing a digital quantification on the diluted second sample droplet to quantify an initial concentration of the species in the sample volume.

17 Claims, 60 Drawing Sheets

Fig. 1: PRIOR ART

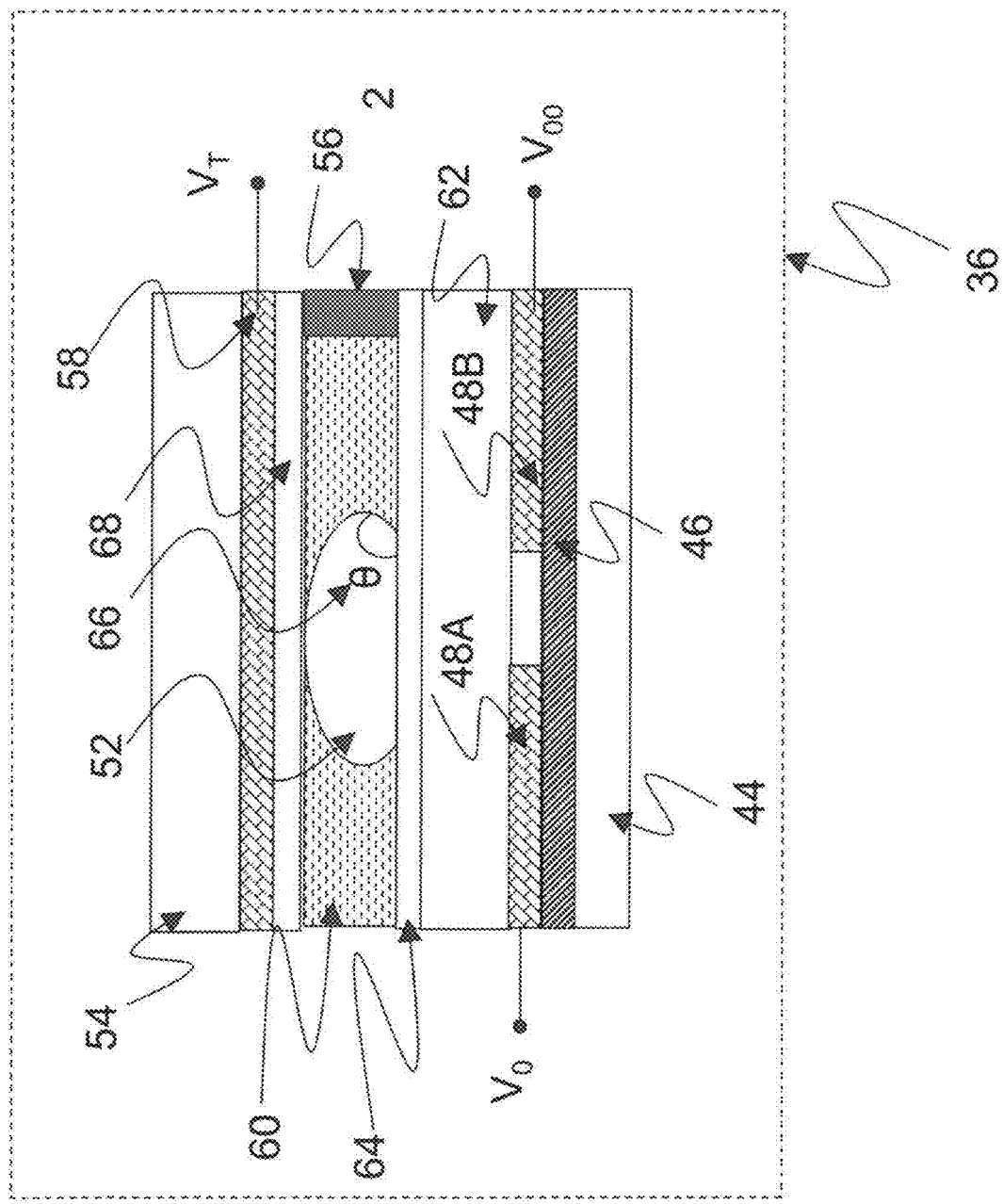

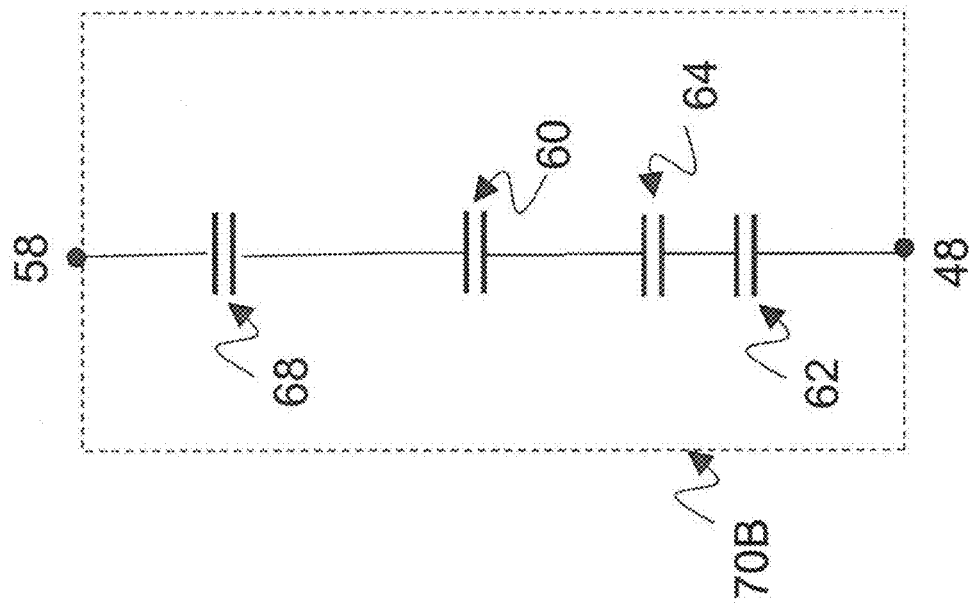
Figure 5B
Fig. 5
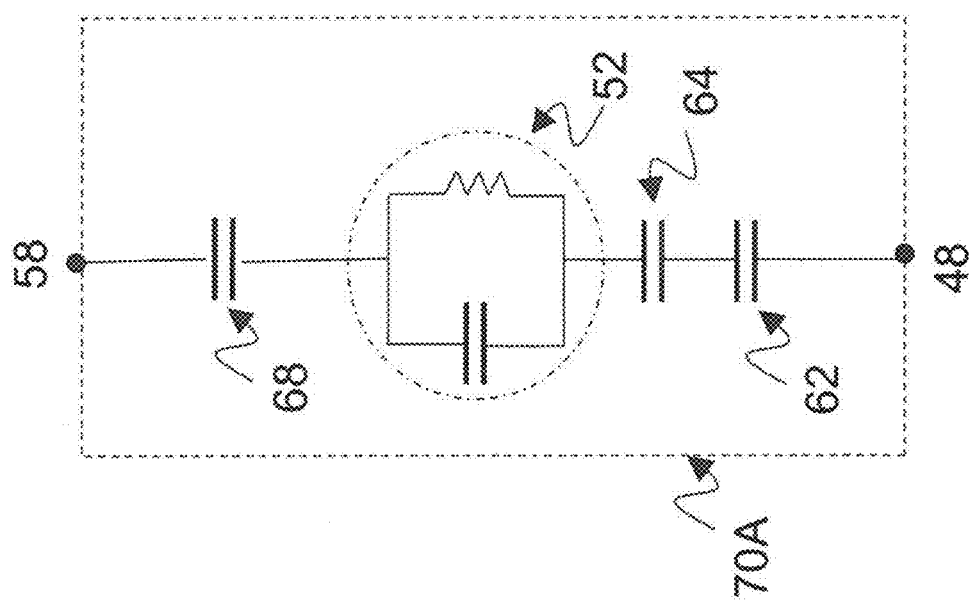
Figure 5A

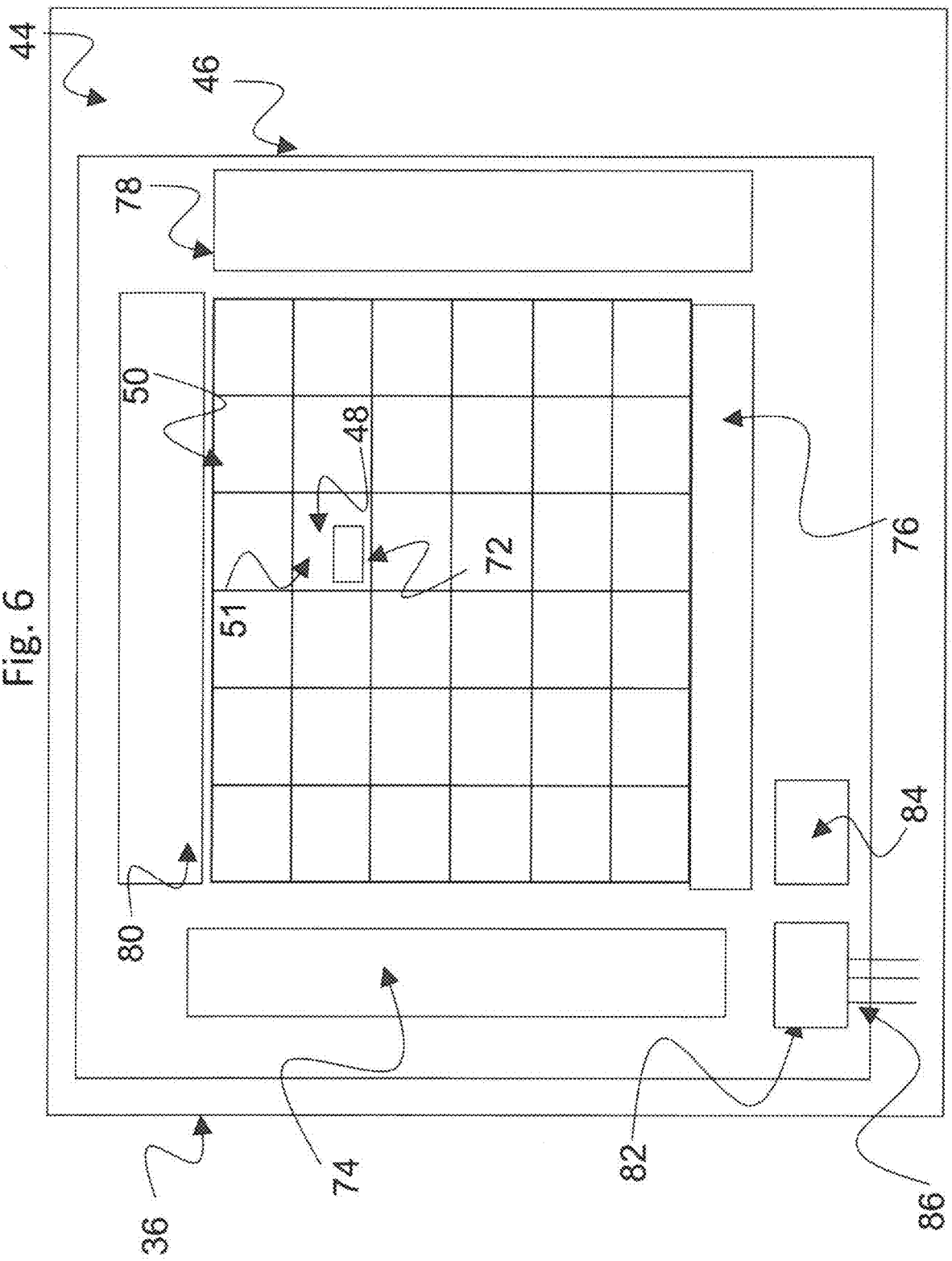

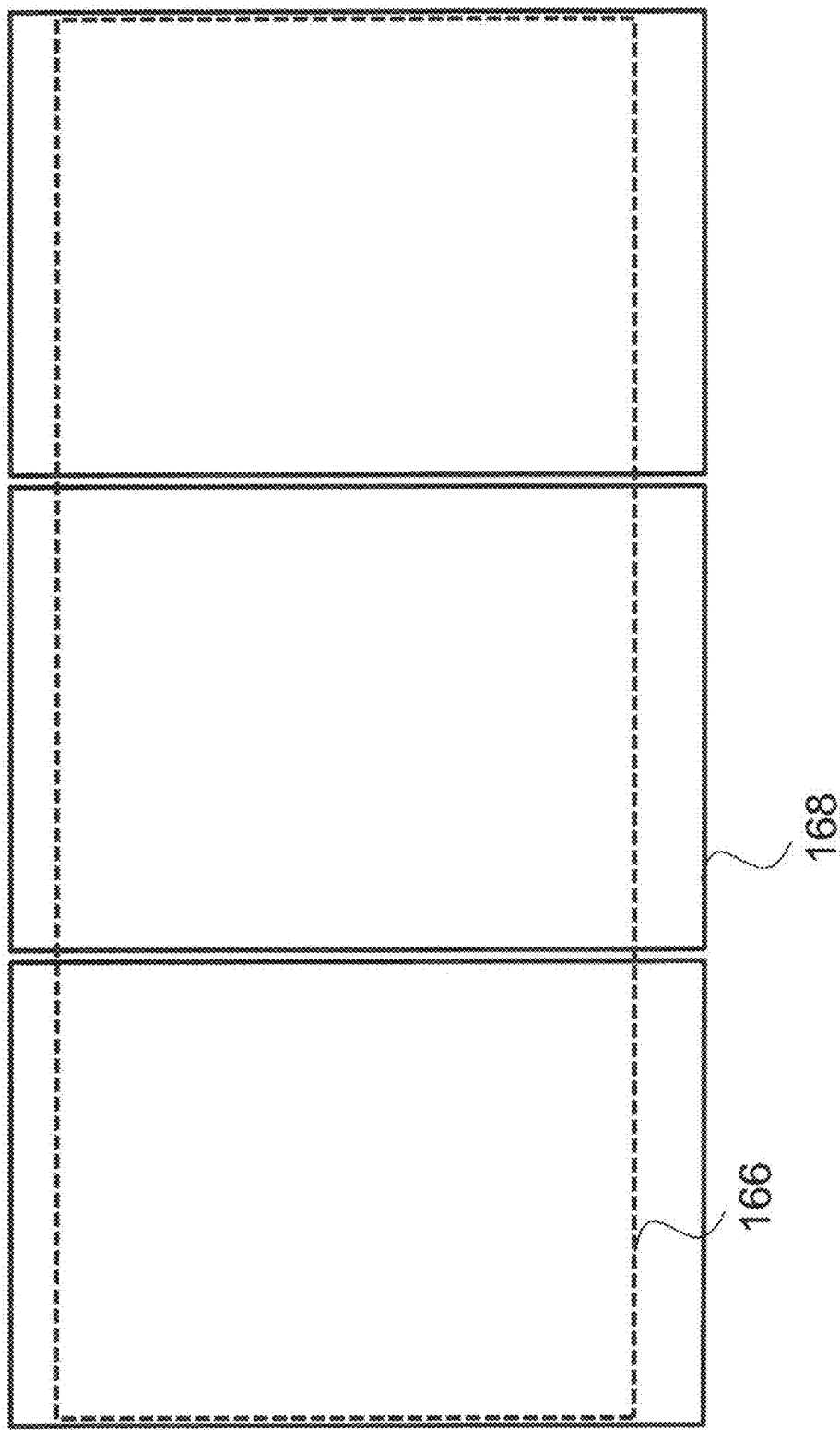

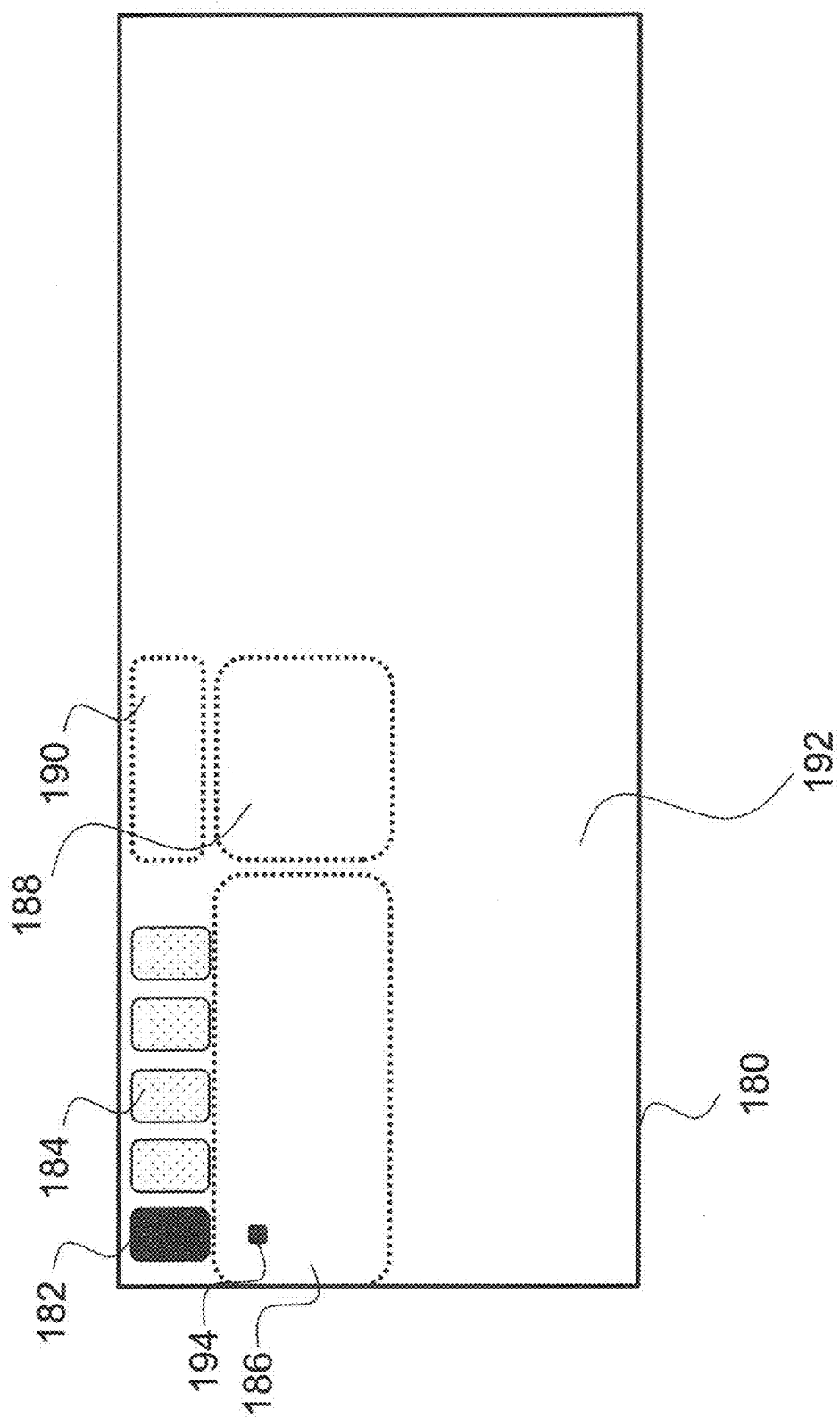

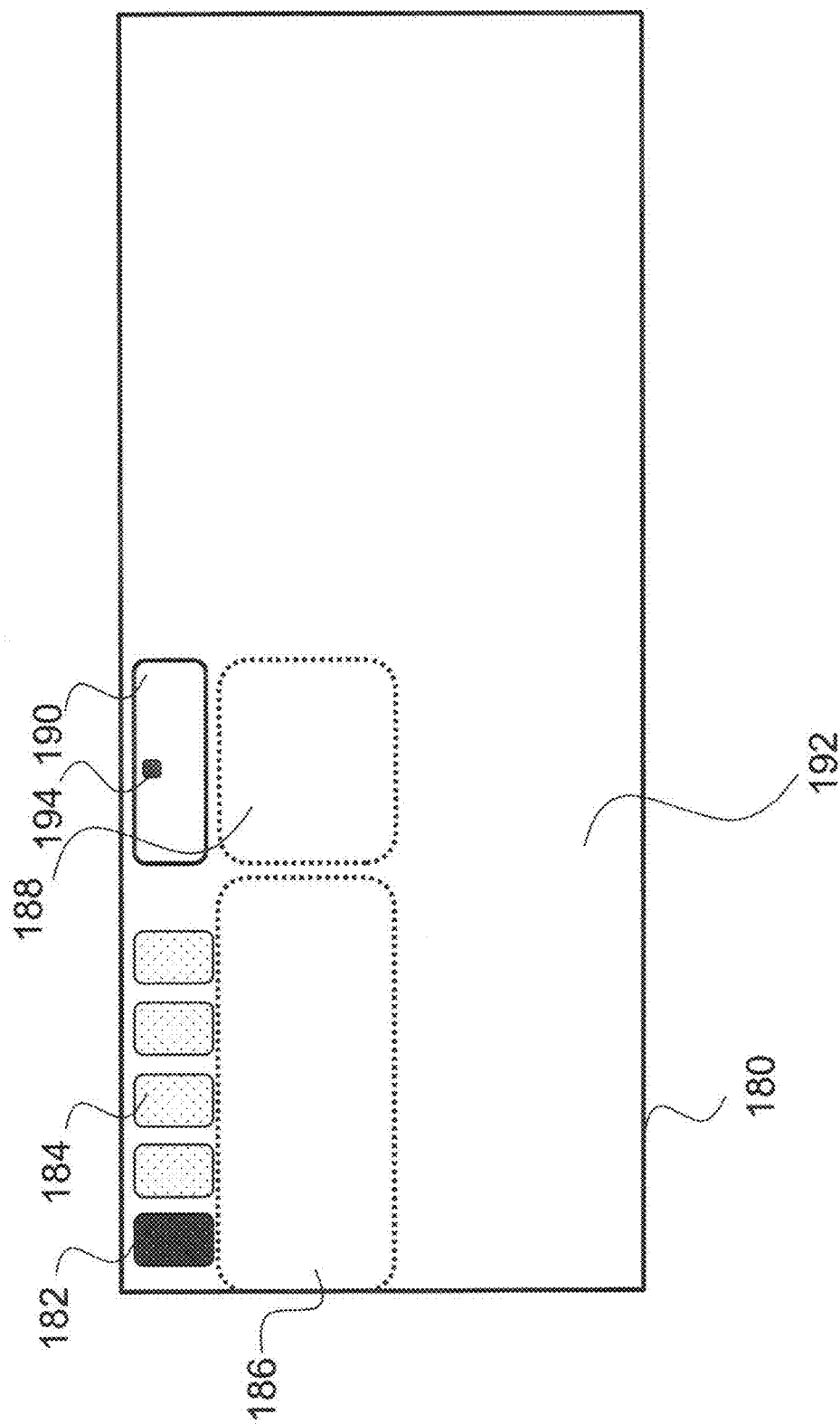

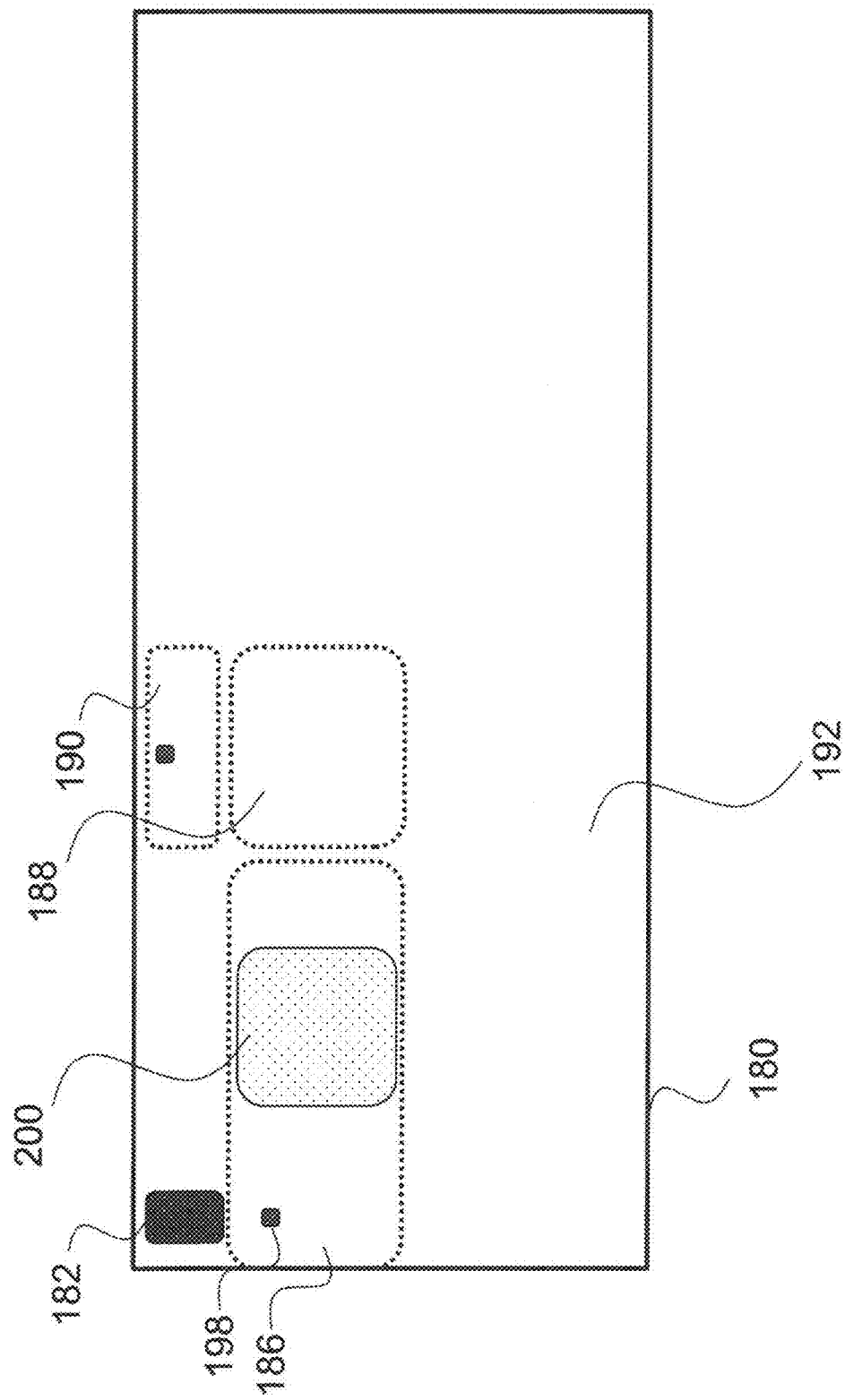

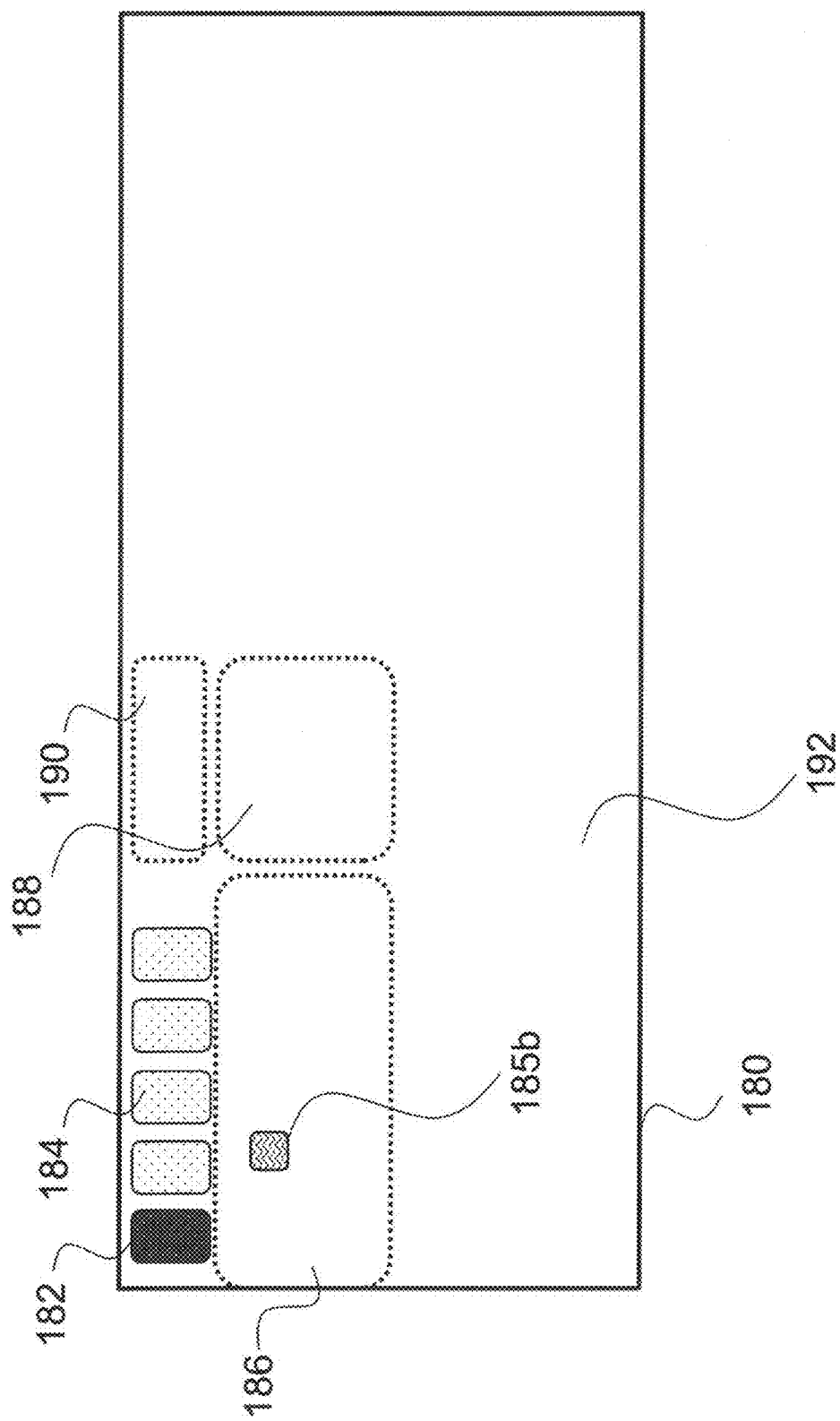

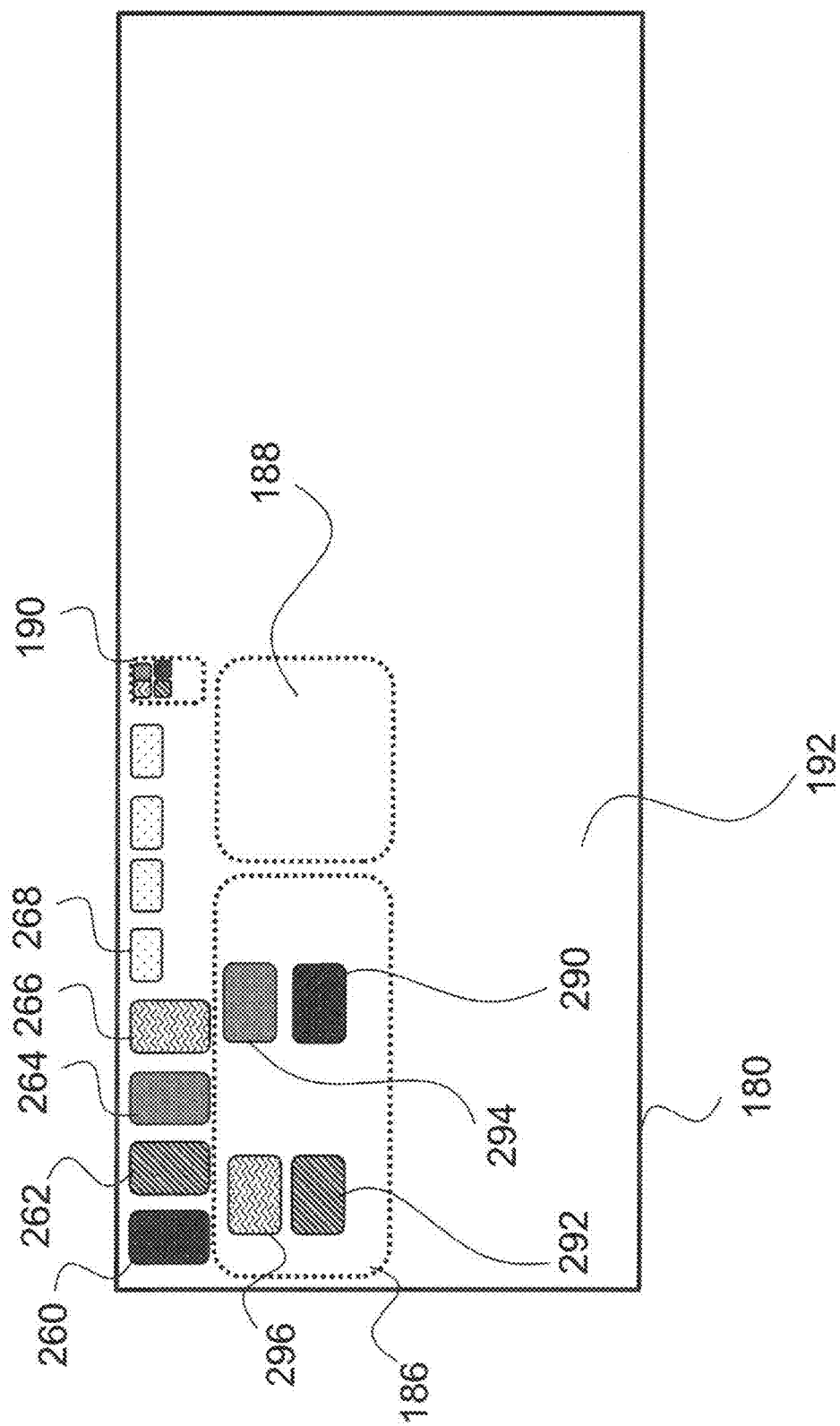

ness of the technology can be found in "Digital microfluidics: is a true lab-on-a-chip possible?", R. B. Fair, Microfluid Nanofluid (2007) 3:245-281).
EWOD SYSTEM AND METHODS TO INCREASE DYNAMIC RANGE FOR DIGITAL NUCLEIC ACID AMPLIFICATION

TECHNICAL FIELD

The present invention relates generally to Active Matrix Electro-wetting-On-Dielectric (AM-EWOD) devices and to digital assay amplification techniques, such as for example digital nucleic acid quantitation, ELISA for protein biomarker quantitation, enzymatic assays for quantitation of enzymatic turnover and cell based assays for phenotyping and genotyping. In particular, the invention relates to digital nucleic acid amplification techniques. More particularly, the invention relates to systems and methods of performing digital amplification assays, such as digital nucleic acid amplification techniques, on an AM-EWOD or EWOD device.

BACKGROUND ART

Electrowetting on dielectric (EWOD) is a well-known technique for manipulating droplets of fluid by the application of an electric field. Active Matrix EWOD (AM-EWOD) refers to implementation of EWOD in an active matrix array incorporating transistors, for example by using thin film transistors (TFTs). It is thus a candidate technology for digital microfluidics for lab-on-a-chip technology. An introduction to the basic principles of the technology can be found in "Digital microfluidics: is a true lab-on-a-chip possible?", R. B. Fair, Microfluid Nanofluid (2007) 3:245-281).

FIG. 1 shows a part of a conventional EWOD device in cross section. The device includes a lower substrate 10, the uppermost layer of which is formed from a conductive material which is patterned so that a plurality of array element electrodes 12 (e.g., 12A and 12B in FIG. 1) are realized. The electrode of a given array element may be termed the element electrode 12. A liquid droplet 14, including a polar material (which is commonly also aqueous and/or ionic), is constrained in a plane between the lower substrate 10 and a top substrate 16. A suitable gap between the two substrates may be realized by means of a spacer 18, and a non-polar surround fluid 20 (e.g. oil) may be used to occupy the volume not occupied by the liquid droplet 14. An insulator layer 22 disposed upon the lower substrate 10 separates the conductive element electrodes 12A, 12B from a first hydrophobic coating 24 upon which the liquid droplet 14 sits with a contact angle 26 represented by θ. The hydrophobic coating is formed from a hydrophobic material (commonly, but not necessarily, a fluoropolymer).

On the top substrate 16 is a second hydrophobic coating 28 with which the liquid droplet 14 may come into contact. Interposed between the top substrate 16 and the second hydrophobic coating 28 is a reference electrode 30.

The contact angle θ is defined as shown in FIG. 1, and is determined by the balancing of the surface tension components between the solid-to liquid ($\gamma_{SL}$), the liquid-to non-polar surrounding fluid ($\gamma_{LG}$) and the solid to non-polar surrounding fluid ($\gamma_{SG}$) interfaces, and in the case where no voltages are applied satisfies Young's law, the equation being given by:

$$\cos\theta = \frac{\gamma_{SG} - \gamma_{SL}}{\gamma_{LG}} \quad \text{(equation 1)}$$

In operation, voltages termed the EW drive voltages, (e.g. $V_T$, $V_0$ and $V_{00}$ in FIG. 1) may be externally applied to different electrodes (e.g. reference electrode 30, element electrodes 12, 12A and 12B, respectively). The resulting electrical forces that are set up effectively control the hydrophobicity of the hydrophobic coating 24. By arranging for different EW drive voltages (e.g. $V_0$ and $V_{00}$) to be applied to different element electrodes (e.g. 12A and 12B), the liquid droplet 14 may be moved in the lateral plane between the two substrates 10 and 16.

Example configurations and operation of EWOD devices are described in the following. U.S. Pat. No. 6,911,132 (Pamula et al., issued Jun. 28, 2005) discloses a two dimensional EWOD array to control the position and movement of droplets in two dimensions. U.S. Pat. No. 6,565,727 (Shenderov, issued May 20, 2003) further discloses methods for other droplet operations including the splitting and merging of droplets, and the mixing together of droplets of different materials. U.S. Pat. No. 7,163,612 (Sterling et al., issued Jan. 16, 2007) describes how TFT based thin film electronics may be used to control the addressing of voltage pulses to an EWOD array by using circuit arrangements very similar to those employed in AM display technologies.

The approach of U.S. Pat. No. 7,163,612 may be termed "Active Matrix Electrowetting on Dielectric" (AM-EWOD). There are several advantages in using TFT based thin film electronics to control an EWOD array, namely:

Electronic driver circuits can be integrated onto the lower substrate 10.

TFT-based thin film electronics are well suited to the AM-EWOD application. They are cheap to produce so that relatively large substrate areas can be produced at relatively low cost.

TFTs fabricated in standard processes can be designed to operate at much higher voltages than transistors fabricated in standard CMOS processes. This is significant since many EWOD technologies require electro-wetting voltages in excess of 20V to be applied.

EWOD droplet manipulation devices are a highly desirable platform for automation of chemical/biochemical reactions. Such devices may carry out chemical/biochemical reactions or reaction sequences in droplets that require complex droplet temperature profiles. Different steps of the reactions may need to be performed at different temperatures. There are many applications of EWOD devices that require the temperature of the sample/reagent droplets (and the products produced by combining them together) to be varied to facilitate the desired chemical or biochemical reaction. Many of these reaction protocols require droplets to be taken to multiple different temperatures at different times in the reaction sequence. Many reaction protocols require the droplets to be thermally cycled in time, in some cases undergoing many such thermal cycles.

A significant example of a reaction protocol that requires precise temperature control in an EWOD device over many reaction cycles is droplet based nucleic acid amplification via polymerase chain reaction (PCR). PCR is a well-known reaction protocol for nucleic acid amplification. Conventional PCR methods on EWOD devices include diluting samples by performing a number of serial dilutions (and end point analyses) until an optimum sample concentration is reached. Examples of such methods are taught in the following: U.S. Pat. No. 9,091,649 (Pollack et al., issued Jul. 28, 2015); US2013/0288254 (Pollack et al., published Oct. 31, 2015); WO2015/063767 (Shapiro et al., published May 7, 2015); WO2016170109 (Kwang, published Oct. 27, 2016); and U.S. Pat. No. 9,539,573 (Hadwen et al., issued Jan. 10, 2017). Such prior processes are time consuming, use significant amounts of reagents, and take up substantial space when performed on an EWOD device according to typical usage.

The previous processes demonstrate how a digital regime may be determined empirically by (a) performing a number of serial dilutions, (b) amplifying 100-1000s of the partitions within each of the dilutions, and (c) determining which of the serial dilutions produces a digital output at the end point analysis. The remaining sample can then be manually diluted by the user to the correct concentration and a higher number of partitions analyzed for absolute quantification, such as disclosed for example in WO2016170109 referenced above. These prior processes, however, have not been optimized for performing on an EWOD or AM-EWOD device.

A biology assay is defined as an assay that quantifies the concentration or activity of a biological entity in a sample container, readout may be performed for example using absorption spectroscopy, fluorescence spectroscopy or non-optical methods. (ref) In digital assays biological entities are partitioned into many small containers, these containers may be droplets in an emulsion or chambers that are physically isolated. The number of biological entities in each container is a discrete number (0, 1, 2, 3, 4 . . . ). During a digital assay each partition is individually assessed and the output is either 0—there are no biological entities in the partition or 1—there is at least one biological entity in the partition. Where the number of partitions is large then the binomial distribution that describes the discrete probability distribution that a particular partition contains a particular number of biological entities may be approximated by the Poisson distribution and the number of zeros used to precisely count the number of biological entities and hence the original sample concentration before partitioning. It is not necessary to carry out limiting dilution of biological entities and partitions may contain up to 4 or 5 biological entities although the noise is greater at higher loading.

Various digital PCR systems, which are not based on EWOD technology, are commercially available, and typically divide a ~20-25 uL sample into between 496 and 5,000,000 partitions. The optimal concentration for digital PCR quantification is between 0.7 and 1.6 mean copies per partition, and it follows that the more partitions you have for a given sample volume, the larger the dynamic range of the system is without requiring the user to manually change the sample concentration. The current commercially available digital PCR platforms are based on either (a) water in oil emulsions or (b) physical partitions. Emulsion based systems tend to have a first instrument for creating the emulsions (partitions in an oil phase), a second instrument for performing PCR thermal cycling, and a third instrument for taking fluorescent images of the partitions and to assign a positive or negative value to them. Physical partitioning systems physically create partitions using techniques such as through holes, or chambers impressed into a substrate.

Conventional digital PCR systems, however, have significant deficiencies. Conventional systems typically require that the user finds the correct sample concentration empirically. Usually, this takes the form of running multiple experiments, in parallel or series, in which the sample is diluted 10-fold for each run until a digitized sample output is obtained. If the sample is too concentrated, then all partitions will be positive and no quantitative information about sample concentration can be obtained. This is a wasteful approach both in terms of time and reagents. The conventional systems also are inefficient and may require multiple devices to perform different stages of the reaction protocol.

SUMMARY OF INVENTION

The present invention describes systems and methods for increasing the dynamic range of sample concentrations that can be quantified using digital assay amplification techniques, such as for example digital nucleic acid amplification techniques (including digital PCR), on an EWOD device. The digital PCR and other digital amplification methods calculate a dilution factor for a sample with an unknown starting concentration of template DNA to produce a digitized output for quantification. The present invention is particularly useful for performing high-ratio dilutions of a sample for digital PCR applications.

There is a need in the art for a nucleic acid amplification technique that can:
  Accurately quantify a sample concentration of nucleic acid less than 10 pg/uL.
  Perform the sample quantification step using less than 1 uL of the total sample volume, leaving more of the sample volume available for analysis.
  Determine the optimal dilution factor required to absolutely quantify the sample using digital nucleic acid amplification techniques.

There is a further need for a digital nucleic acid amplification technology that:
  Uses only a single instrument.
  Can integrate a sample quantification step into a more complex workflow, thus simplifying a user protocol.
  Automatically dilutes a sample by the correct ratio for quantification by digital nucleic acid amplification without any user intervention.
  Automatically partitions said optimally diluted sample for digital nucleic acid amplification.
  Automatically quantifies the absolute concentration of the nucleic acid sample.

There is yet a further need for a digital nucleic acid amplification technology that:
  Can automatically identify positive and negative partitions.
  Sorts said positive and negative partitions.
  Supports sample extraction of said sorted positive and negative partitions for further downstream processing.
  Reduces or eliminates the potential for cross-contamination by providing distinct zones for (a) quantification of sample concentration, (b) sample dilution, and (c) sample partitioning with nucleic acid amplification.

The present invention streamlines the process of high-ratio dilution and establishing the concentration suitable for digital nucleic acid amplification analysis by calculating a single, optimal dilution factor. This reduces (a) the volume of reagents used, and (b) the total area required to perform the dilution on an EWOD device. Advantages are achieved in decreasing the time to first result, and may offer further advantages by improving the accuracy of the end result. In relation to digital nucleic acid amplification applications on EWOD devices, the present invention enables a wide range of initial sample concentrations to be analyzed in a digital nucleic acid amplification format using as few as 100-2,000 droplets. This improves the dynamic range of an EWOD device, which would otherwise be restricted due to the relatively small number of droplets that can be accommodated on the device at any one time. The need to be able to perform a small number of high-ratio dilutions within a minimal footprint achieves a simple, low throughput digital nucleic acid amplification system.

An aspect of the invention, therefore, is an enhanced electrowetting on dielectric (EWOD) device and a related method of performing a digital assay amplification technique in an EWOD device. In exemplary embodiments, the method may include the steps of: inputting a sample volume containing a molecular species of interest into the EWOD device; inputting a diluent volume into the EWOD device; performing an electrowetting operation to extract a first sample droplet from the sample volume; performing an amplification on the first sample droplet within the EWOD device; measuring a turn-on value (e.g. a fluorescence above threshold value) for the sample droplet; comparing the measured turn-on value of the sample droplet to a bulk volume target turn-on value expected to support digital amplification of the molecular species in the sample; calculating a dilution factor based on the comparison of the measured turn-on value of the sample droplet to the target turn-on value; performing an electrowetting operation to extract a second sample droplet from the sample volume; performing an electrowetting operation to dilute the sample droplet with the diluent volume in accordance with the dilution factor to form a diluted sample droplet; and performing a digital amplification assay to quantify a concentration of a molecular species in the sample volume.

A further aspect of the invention, therefore, is an enhanced electrowetting on dielectric (EWOD) device and a related method of performing a digital nucleic acid amplification technique in an EWOD device. In exemplary embodiments, the method may include the steps of: inputting a sample volume containing a nucleic acid sample into the EWOD device; inputting a diluent volume into the EWOD device; performing an electrowetting operation to extract a first sample droplet from the sample volume; performing nucleic acid amplification on the first sample droplet within the EWOD device; measuring a turn-on value (e.g. a cycle threshold (Ct) or time to positive (Tp)) for the sample droplet; comparing the measured turn-on value of the sample droplet to a target turn-on value expected to support subsequent digital amplification of the nucleic acid sample; calculating a dilution factor based on the comparison of the measured turn-on value of the sample droplet to the target turn-on value; performing an electrowetting operation to extract a second sample droplet from the sample volume; performing an electrowetting operation to dilute the sample droplet with the diluent volume in accordance with the dilution factor to form a diluted sample droplet; and performing a digital nucleic acid amplification to quantify an initial concentration of the nucleic acid sample in the sample volume.

Another aspect of the invention is a non-transitory computer-readable medium storing program code which is executed by a processing device for controlling actuation voltages applied to array elements of an element array of an electro-wetting on dielectric (EWOD) device for performing droplet manipulations on droplets on the element array, the program code being executable by the processing device to perform the steps of the method of performing a digital amplification technique in an EWOD device.

According to another aspect of the invention, a microfluidic system includes an electro-wetting on dielectric (EWOD) device comprising an element array configured to receive one or more liquid droplets, the element array comprising a plurality of individual array elements; and a control system configured to control actuation voltages applied to the element array to perform manipulation operations as to the liquid droplets to perform the method of performing a digital nucleic acid amplification technique. A plurality of thermal control elements may be located at different spatial locations along the EWOD device, and wherein the control system includes a thermal control unit configured to control temperatures of the plurality of thermal control elements to generate a plurality of thermal zones located at different spatial locations along the EWOD device. In exemplary embodiments, the control system controls the actuation voltages applied to the element array to form separate zones includes a sample preparation zone to prepare the first sample droplet, a first amplification zone in which the nucleic acid amplification on the first sample droplet is performed, and a digital amplification zone in which the digital nucleic acid amplification is performed. The sample preparation zone, the first amplification zone, and the digital amplification zone spatially correspond to different thermal control elements.

It will be understood by those of ordinary skill in the art that principles of the present invention are not limited to digital PCR assays, and that the principles of the present invention are fully compatible with digital assays in biology, such as for example digital nucleic acid quantitation, ELISA for protein biomarker quantitation, enzymatic assays for quantitation of enzymatic turnover and cell based assays for phenotyping and genotyping.

Digital nucleic acid assays are performed to quantify the concentration of a nucleic acid sequence. A sample containing target DNA, polymerase chain reaction (PCR) reagents and fluorescent probes is partitioned with commercial systems generating between 1000 and 10 million partitions. The partitions are then thermal cycled at least 30 times. DNA in DNA containing partitions is amplified and the partition becomes fluorescent. No DNA amplification occurs in the DNA free partitions and these droplets do not become fluorescent. The proportion of non-fluorescent partitions is analysed with Poisson statistics to calculate the target DNA concentration.

Digital protein assays may be used to quantify proteins in samples, particularly low abundance biomarker proteins in serum samples using the ELISA. (ELISA is a widely used technique to detect any protein that can be bound to an antibody) or to quantify enzymes that have enzymatic activity.

Digital cell based assays involve the encapsulation of discrete numbers of cells in partitions and the measuring of features of cell phenotype and genotype e.g. cell secretions, cell surface biomarkers, cell metabolites etc usually by partitioning cells into partitions containing fluorogenic substrates for enzymatically amplified detection.

These and further features of the present invention will be apparent with reference to the following description and attached drawings. In the description and drawings, particular embodiments of the invention have been disclosed in detail as being indicative of some of the ways in which the principles of the invention may be employed, but it is understood that the invention is not limited correspondingly in scope. Rather, the invention includes all changes, modifications and equivalents coming within the spirit and terms of the claims appended hereto. Features that are described and/or illustrated with respect to one embodiment may be used in the same way or in a similar way in one or more other embodiments and/or in combination with or instead of the features of the other embodiments.

BRIEF DESCRIPTION OF DRAWINGS

FIG. 4 is a drawing depicting a cross section through some of the array elements of the exemplary AM-EWOD device of FIG. 3.

FIG. 5A is a drawing depicting a circuit representation of the electrical load presented at the element electrode when a liquid droplet is present.

FIG. 5B is a drawing depicting a circuit representation of the electrical load presented at the element electrode when no liquid droplet is present.

FIG. 6 is a drawing depicting an exemplary arrangement of thin film electronics in the exemplary AM-EWOD device of FIG. 3 in accordance with embodiments of the present invention.

FIG. 13A, FIG. 13B, and FIG. 13C are drawings depicting different exemplary configurations of thermal control elements to generate multiple temperature zones in an EWOD device.

FIG. 14A, FIG. 14B, FIG. 14C, FIG. 14D, FIG. 14E, FIG. 14F, FIG. 14G, FIG. 14H, and FIG. 14I are drawings depicting a progression of steps constituting an exemplary method of performing a digital PCR reaction protocol in accordance with embodiments of the present invention.

FIG. 17A, FIG. 17B, FIG. 17C, FIG. 17D, FIG. 17E, FIG. 17F, FIG. 17G, FIG. 17H, FIG. 17I, and FIG. 17J are drawings depicting a progression of steps constituting another exemplary method of performing a digital PCR reaction protocol in accordance with embodiments of the present invention, including a determination of efficiency of reaction.

FIG. 21A, FIG. 21B, FIG. 21C, FIG. 21D, FIG. 21E, FIG. 21F, and FIG. 21G are drawings depicting a progression of steps constituting another exemplary method of performing a digital PCR reaction protocol in accordance with embodiments of the present invention, including the use of internal reference targets for more accurate determinations.

DESCRIPTION OF EMBODIMENTS

Figure 1:
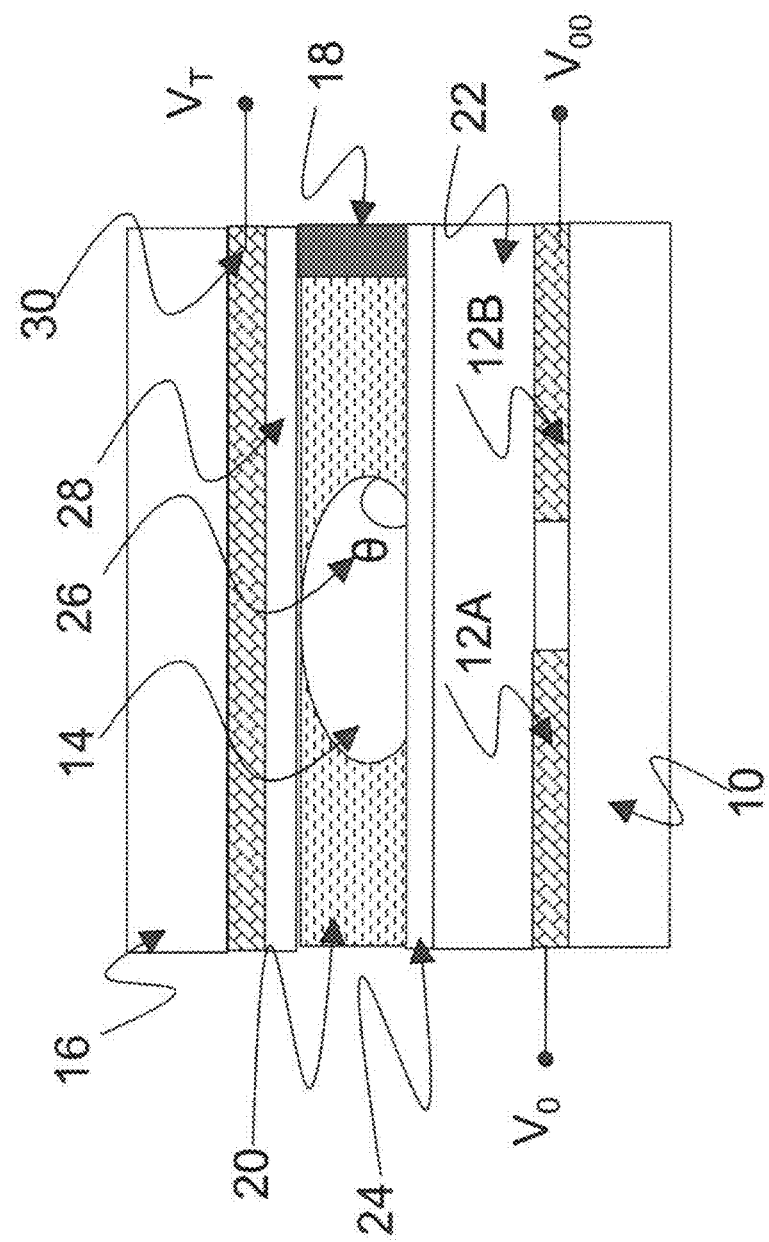
FIG. 1 is a drawing depicting a conventional EWOD device in cross-section.

Embodiments of the present invention will now be described with reference to the drawings, wherein like reference numerals are used to refer to like elements throughout. It will be understood that the figures are not necessarily to scale.

Figure 2:
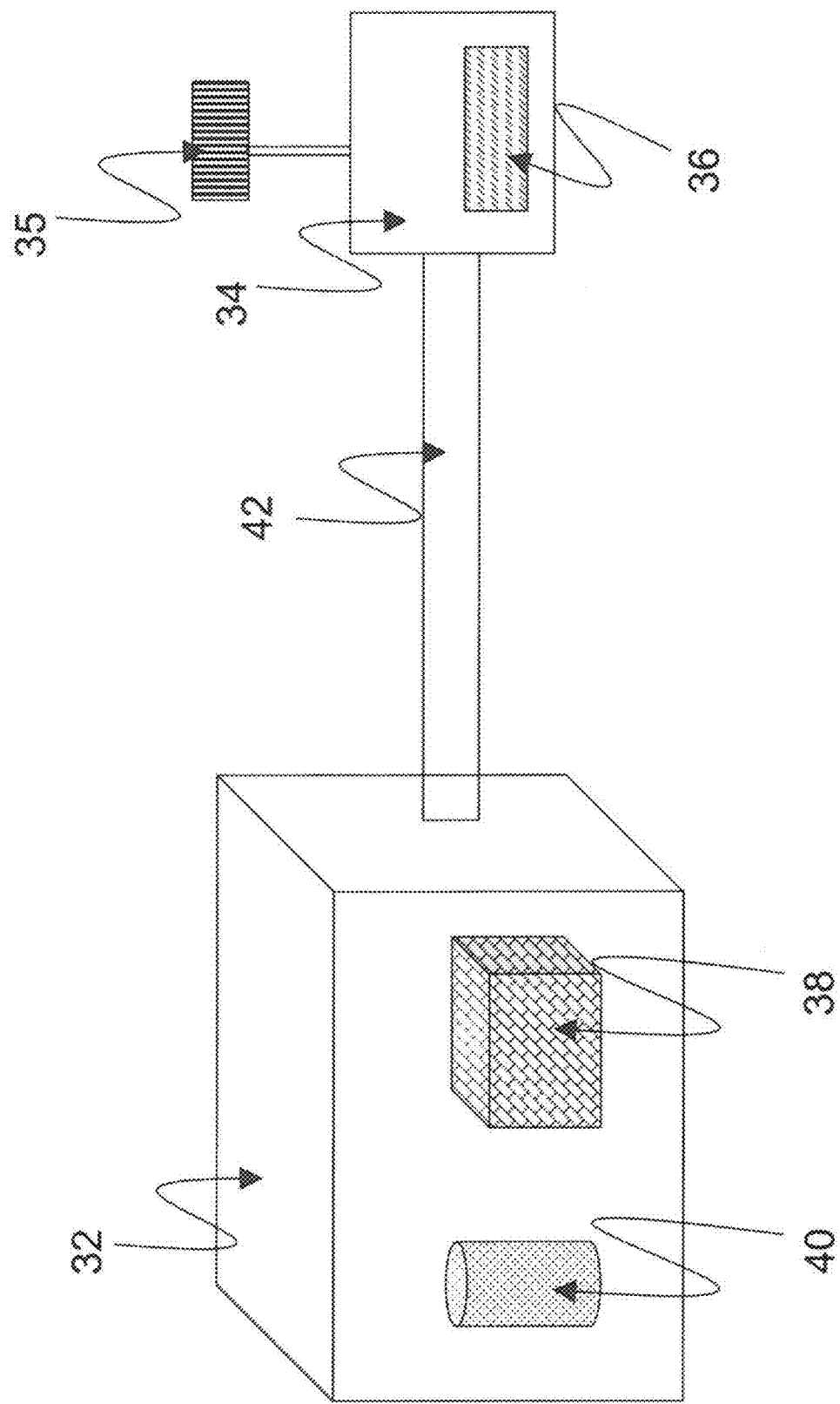
FIG. 2 is a drawing depicting an exemplary EWOD based microfluidic system according to embodiments of the present invention.

FIG. 2 is a drawing depicting an exemplary EWOD based microfluidic system according to embodiments of the present invention. In the example of FIG. 2, the measurement system includes a reader 32 and a cartridge 34. The cartridge 34 may contain a microfluidic device, such as an EWOD or AM-EWOD device 36, as well as (not shown) fluid input ports into the device and an electrical connection as are conventional. The fluid input ports may perform the function of inputting fluid into the AM-EWOD device 36 and generating droplets within the device, for example by dispensing from input reservoirs as controlled by electro-wetting. As further detailed below, the microfluidic device includes an electrode array configured to receive the inputted fluid droplets.

The microfluidic system further may include a control system configured to control actuation voltages applied to the electrode array of the microfluidic device to perform manipulation operations to the fluid droplets. For example, the reader 32 may contain such a control system configured as control electronics 38 and a storage device 40 that may store any application software any data associated with the system. The control electronics 38 may include suitable circuitry and/or processing devices that are configured to carry out various control operations relating to control of the AM-EWOD device 36, such as a CPU, microcontroller or microprocessor.

Among their functions, to implement the features of the present invention, the control electronics may comprise a part of the overall control system that may execute program code embodied as a control application within the storage device 40. It will be apparent to a person having ordinary skill in the art of computer programming, and specifically in application programming for electronic control devices, how to program the control system to operate and carry out logical functions associated with the stored control application. Accordingly, details as to specific programming code have been left out for the sake of brevity. The storage device 40 may be configured as a non-transitory computer readable medium, such as random access memory (RAM), a read-only memory (ROM), an erasable programmable read-only memory (EPROM or Flash memory), or any other suitable medium. Also, while the code may be executed by control electronics 38 in accordance with an exemplary embodiment, such control system functionality could also be carried out via dedicated hardware, firmware, software, or combinations thereof, without departing from the scope of the invention.

The control system may be configured to perform some or all of the following functions:
  Define the appropriate timing signals to manipulate liquid droplets on the AM-EWOD device 36.
  Interpret input data representative of sensor information measured by a sensor or sensor circuitry associated with the AM-EWOD device 36, including computing the locations, sizes, centroids and perimeters of liquid droplets on the AM-EWOD device 36.
  Use calculated sensor data to define the appropriate timing signals to manipulate liquid droplets on the AM-EWOD device 36, i.e. acting in a feedback mode.
  Provide for implementation of a graphical user interface (GUI) whereby the user may program commands such as droplet operations (e.g. move a droplet), assay operations (e.g. perform an assay), and the GUI may report the results of such operations to the user.
  In accordance with embodiments of the present invention, and as further detailed below, the control system may include a thermal control unit configured to control temperature of the EWOD device within the EWOD channel as is suitable for a given reaction protocol.

In the example of FIG. 2, an external sensor module 35 may be provided for sensing droplet properties. For example, optical sensors as are known in the art may be employed as external sensors for sensing droplet properties. Suitable optical sensors include camera devices, light sensors, charged coupled devices (CCDs) and image similar image sensors, and the like. A sensor alternatively may be configured as internal sensor circuitry incorporated as part of the drive circuitry in each array element. Such sensor circuitry may sense droplet properties by the detection of an electrical property at the array element, such as impedance or capacitance.

The control system, such as via the control electronics 38, may supply and control the actuation voltages applied to the electrode array of the microfluidics device 36, such as required voltage and timing signals to perform droplet manipulation operations and sense liquid droplets on the AM-EWOD device 36. The control electronics further may execute the application software to generate and output control voltages for droplet sensing and performing sensing operations. The reader 32 and cartridge 34 may be electrically connected together while in use, for example by a cable of connecting wires 42, although various other methods (e.g. wireless connection) of providing electrical communication may be used as are known to those of ordinary skill in the art.

Figure 3:
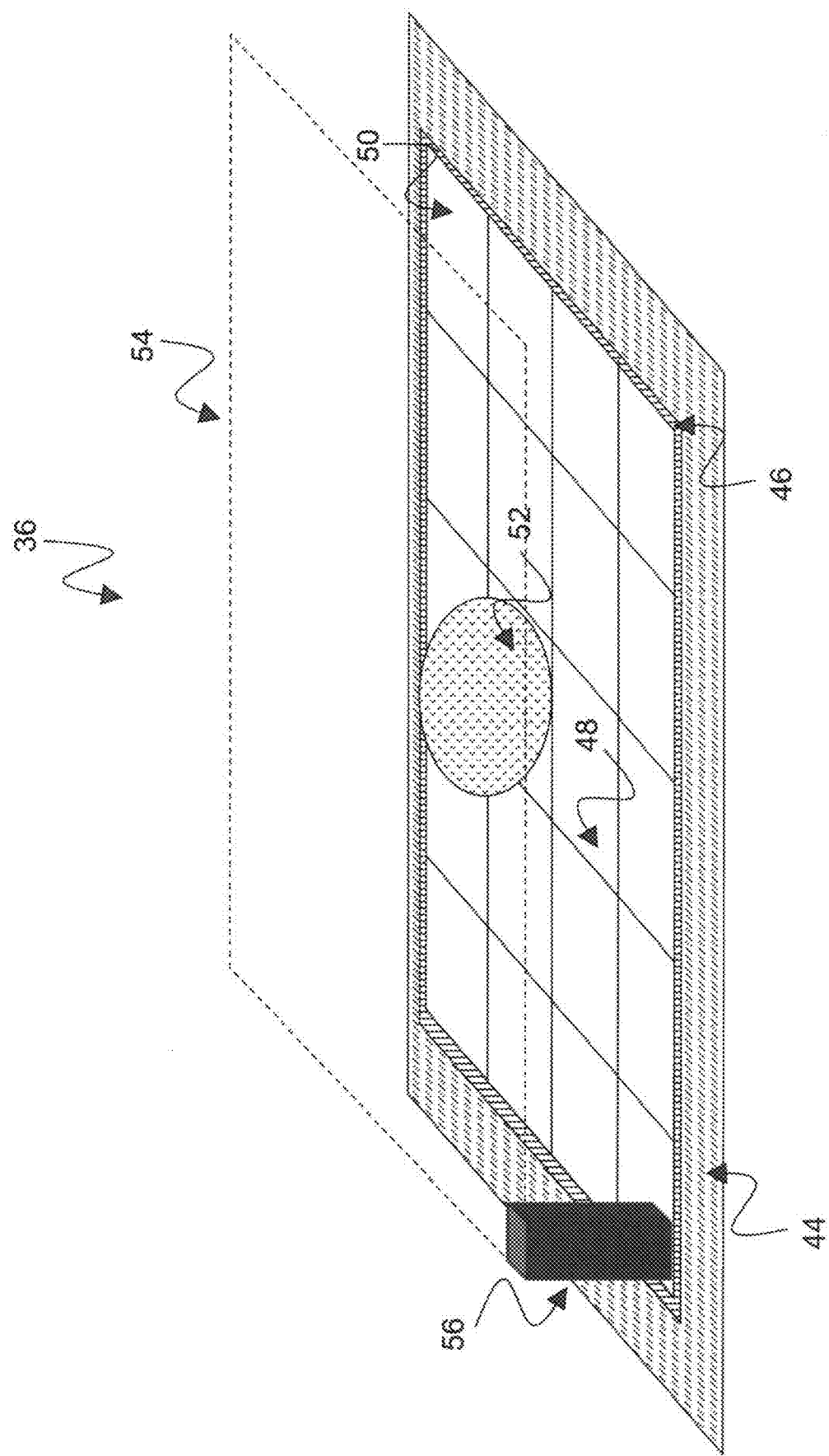
FIG. 3 is a drawing depicting an exemplary AM-EWOD device in schematic perspective in accordance with embodiments of the present invention.

FIG. 3 is a drawing depicting additional details of the exemplary AM-EWOD device 36 in schematic perspective in accordance with embodiments of the present invention. The AM-EWOD device 36 has a lower substrate 44 with thin film electronics 46 disposed upon the lower substrate 44. The thin film electronics 46 are arranged to drive array element electrodes 48. A plurality of array element electrodes 48 are arranged in an electrode or element array 50, having X by Y array elements where X and Y may be any integer. A liquid droplet 52 which may include any polar liquid and which typically may be aqueous, is enclosed between the lower substrate 44 and a top substrate 54 separated by a spacer 56, although it will be appreciated that multiple liquid droplets 52 can be present.

FIG. 4 is a drawing depicting a cross section through some of the array elements of the exemplary AM-EWOD 36 device of FIG. 3. In the portion of the AM-EWOD device depicted in FIG. 4, the device includes a pair of the array element electrodes 48A and 48B that are shown in cross section that may be utilized in the electrode or element array 50 of the AM-EWOD device 36 of FIG. 3. The device configuration is similar to the conventional configuration shown in FIG. 1, with the AM-EWOD device 36 further incorporating the thin-film electronics 46 disposed on the lower substrate 44, which is separated from the upper substrate 54 by the spacer 56. The uppermost layer of the lower substrate 44 (which may be considered a part of the thin film electronics layer 46) is patterned so that a plurality of the array element electrodes 48 (e.g. specific examples of array element electrodes are 48A and 48B in FIG. 4) are realized. The term element electrode 48 may be taken in what follows to refer both to the physical electrode structure 48 associated with a particular array element, and also to the node of an electrical circuit directly connected to this physical structure. A reference electrode 58 is shown in FIG. 4 disposed upon the top substrate 54, but the reference electrode alternatively may be disposed upon the lower substrate 44 to realize an in-plane reference electrode geometry. The term reference electrode 58 may also be taken in what follows to refer to both or either of the physical electrode structure and also to the node of an electrical circuit directly connected to this physical structure.

Also similarly to the conventional structure of FIG. 1, in the AM-EWOD device 36, a non-polar fluid 60 (e.g. oil) may be used to occupy the volume not occupied by the liquid droplet 52. An insulator layer 62 may be disposed upon the lower substrate 44 that separates the conductive element electrodes 48A and 48B from a first hydrophobic coating 64 upon which the liquid droplet 52 sits with a contact angle 66 represented by θ. The hydrophobic coating is formed from a hydrophobic material (commonly, but not necessarily, a fluoropolymer). On the top substrate 54 is a second hydrophobic coating 68 with which the liquid droplet 52 may come into contact. The reference electrode 58 is interposed between the top substrate 54 and the second hydrophobic coating 68.

FIG. 5A shows a circuit representation of the electrical load 70A between the element electrode 48 and the reference electrode 58 in the case where a liquid droplet 52 is present. The liquid droplet 52 can usually be modeled as a resistor and capacitor in parallel. Typically, the resistance of the droplet will be relatively low (e.g. if the droplet contains ions) and the capacitance of the droplet will be relatively high (e.g. because the relative permittivity of polar liquids is relatively high, e.g. ~80 if the liquid droplet is aqueous). In many situations the droplet resistance is relatively small, such that at the frequencies of interest for electro-wetting, the liquid droplet 52 may function effectively as an electrical short circuit. The hydrophobic coatings 64 and 68 have electrical characteristics that may be modelled as capacitors, and the insulator 62 may also be modelled as a capacitor. The overall impedance between the element electrode 48 and the reference electrode 58 may be approximated by a capacitor whose value is typically dominated by the contribution of the insulator 62 and hydrophobic coatings 64 and 68 contributions, and which for typical layer thicknesses and materials may be on the order of a pico-Farad in value.

FIG. 5B shows a circuit representation of the electrical load 70B between the element electrode 48 and the reference electrode 58 in the case where no liquid droplet is present. In this case the liquid droplet components are replaced by a capacitor representing the capacitance of the non-polar fluid 60 which occupies the space between the top and lower substrates. In this case the overall impedance between the element electrode 48 and the reference electrode 58 may be approximated by a capacitor whose value is dominated by the capacitance of the non-polar fluid and which is typically small, of the order of femto-Farads.

For the purposes of driving and sensing the array elements, the electrical load 70A/70B overall functions in effect as a capacitor, whose value depends on whether a liquid droplet 52 is present or not at a given element electrode 48. In the case where a droplet is present, the capacitance is relatively high (typically of order pico-Farads), whereas if there is no liquid droplet present the capacitance is low (typically of order femto-Farads). If a droplet partially covers a given electrode 48 then the capacitance may approximately represent the extent of coverage of the element electrode 48 by the liquid droplet 52.

FIG. 6 is a drawing depicting an exemplary arrangement of thin film electronics 46 in the exemplary AM-EWOD device 36 of FIG. 3 in accordance with embodiments of the present invention. The thin film electronics 46 is located upon the lower substrate 44. Each array element 51 of the array of elements 50 contains an array element circuit 72 for controlling the electrode potential of a corresponding element electrode 48. Integrated row driver 74 and column driver 76 circuits are also implemented in thin film electronics 46 to supply control signals to the array element circuit 72. The array element circuit 72 may also contain a sensing capability for detecting the presence or absence of a liquid droplet in the location of the array element. Integrated sensor row addressing 78 and column detection circuits 80 may further be implemented in thin film electronics for the addressing and readout of the sensor circuitry in each array element.

A serial interface 82 may also be provided to process a serial input data stream and facilitate the programming of the required voltages to the element electrodes 48 in the array 50. A voltage supply interface 84 provides the corresponding supply voltages, top substrate drive voltages, and other requisite voltage inputs as further described herein. A number of connecting wires 86 between the lower substrate 44 and external control electronics, power supplies and any other components can be made relatively few, even for large array sizes. Optionally, the serial data input may be partially parallelized. For example, if two data input lines are used the first may supply data for columns 1 to X/2, and the second for columns (1+X/2) to M with minor modifications to the column driver circuits 76. In this way the rate at which data can be programmed to the array is increased, which is a standard technique used in Liquid Crystal Display driving circuitry.

Generally, an exemplary AM-EWOD device 36 that includes thin film electronics 46 may be configured as follows. The AM-EWOD device 36 includes the reference electrode 58 mentioned above (which, optionally, could be an in-plane reference electrode) and a plurality of individual array elements 51 on the array of elements 50, each array element 51 including an array element electrode 48 and array element circuitry 72. Relatedly, the AM-EWOD device 36 may be configured to perform a method of actuating the array elements to manipulate liquid droplets on the array by controlling an electro-wetting voltage to be applied to a plurality of array elements. The applied voltages may be provided by operation of the control system described as to FIG. 2, including the control electronics 38 and applications and data stored on the storage device 40. The electro-wetting voltage at each array element 51 is defined by a potential difference between the array element electrode 48 and the reference electrode 58. The method of controlling the electro-wetting voltage at a given array element typically includes the steps of supplying a voltage to the array element electrode 48, and supplying a voltage to the reference electrode 58, by operation of the control system.

Figure 7:
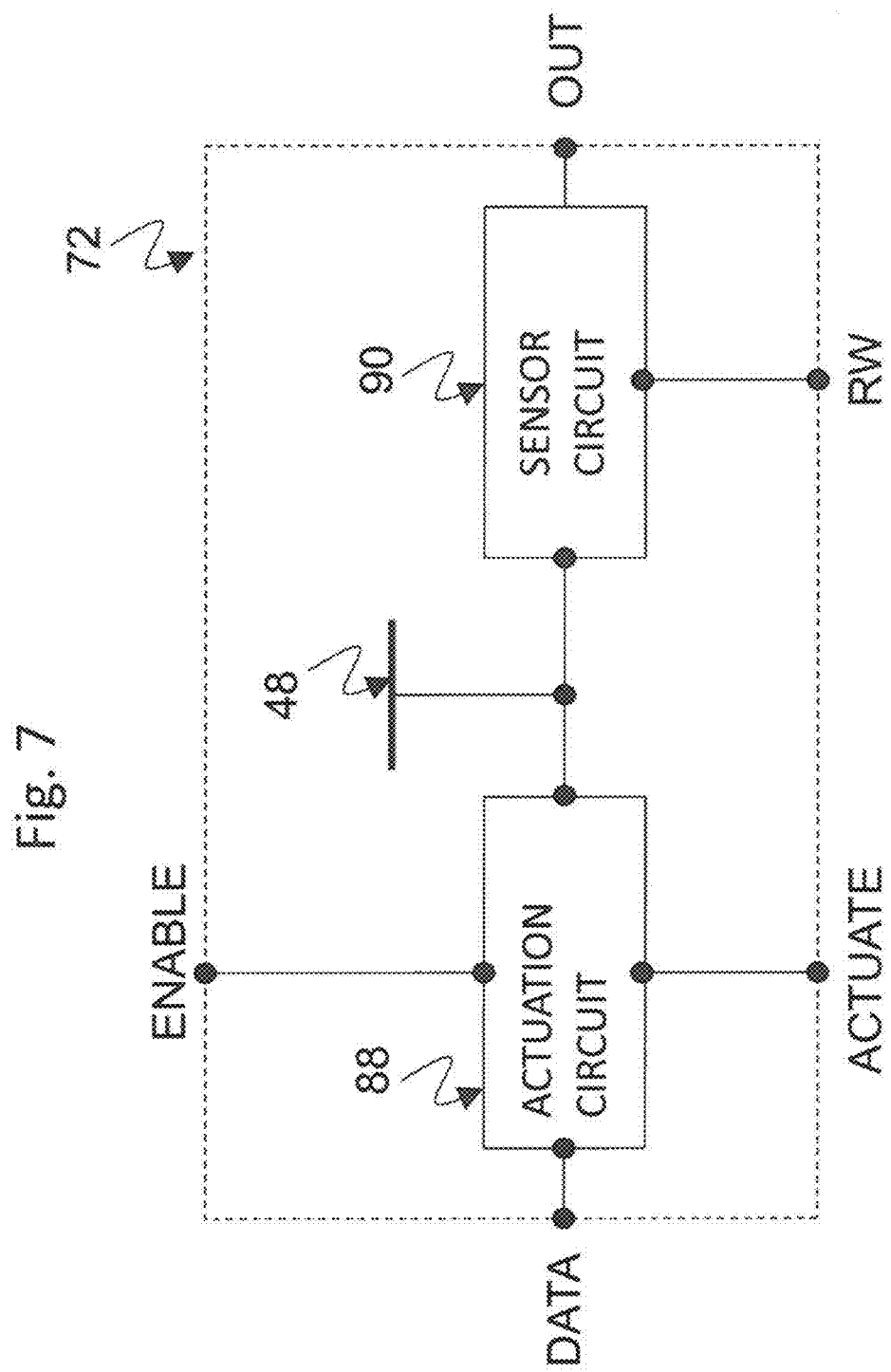
FIG. 7 is a drawing depicting an exemplary arrangement of the array element circuit in accordance with embodiments of the present invention.

FIG. 7 is a drawing depicting an exemplary arrangement of the array element circuit 72 present in each array element 51, in accordance with embodiments of the present invention. The array element circuit 72 may contain an actuation circuit 88, having inputs ENABLE, DATA and ACTUATE, and an output which is connected to an element electrode 48. The array element circuit 72 also may contain a droplet sensing circuit 90, which may be in electrical communication with the element electrode 48. Typically, the read-out of the droplet sensing circuit 90 may be controlled by one or more addressing lines (e.g. RW) that may be common to elements in the same row of the array, and may also have one or more outputs, e.g. OUT, which may be common to all elements in the same column of the array.

The array element circuit 72 may typically perform the functions of:
(i) Selectively actuating the element electrode 48 by supplying a voltage to the array element electrode. Accordingly, any liquid droplet present at the array element 51 may be actuated or de-actuated by the electro-wetting effect.
(ii) Sensing the presence or absence of a liquid droplet at the location of the array element 51. The means of sensing may be capacitive, optical, thermal or some other means. Capacitive sensing may be employed conveniently and effectively using an impedance sensor circuit as part of the array element circuitry.

Exemplary configurations of array element circuits 72 including impedance sensor circuitry are known in the art, and for example are described in detail in U.S. Pat. No. 8,653,832 referenced in the background art section, and commonly assigned UK application GB1500261.1, both of which are incorporated here by reference. These patent documents include descriptions of how the droplet may be actuated (by means of electro-wetting) and how the droplet may be sensed by capacitive or impedance sensing means. Typically, capacitive and impedance sensing may be analogue and may be performed simultaneously, or near simultaneously, at every element in the array. By processing the returned information from such a sensor (for example in the application software in the storage device 40 of the reader 32), the control system described above can determine in real-time, or almost real-time the position, size, centroid and perimeter of each liquid droplet present in the array of elements 50. As referenced in connection with FIG. 2, an alternative to sensor circuitry is to provide an external sensor (e.g., sensor 35), such as an optical sensor that can be used to sense droplet properties.

Common PCR methods include performing portions of the reaction protocol at different temperatures. Accordingly, the present invention uses enhanced control of temperature in an EWOD device to optimize temperature in the EWOD channel where the droplet manipulations and reactions occur. A complete description of an exemplary EWOD device incorporating enhanced temperature control is provided in Applicant's application Ser. No. 15/607,940 filed on May 30, 2017, the content of which is incorporated here by reference. For illustration purposes, a portion of such description is provided herein. It will be appreciated that the following is an example, and any suitable temperature control within the EWOD device may be employed.

Figure 8:
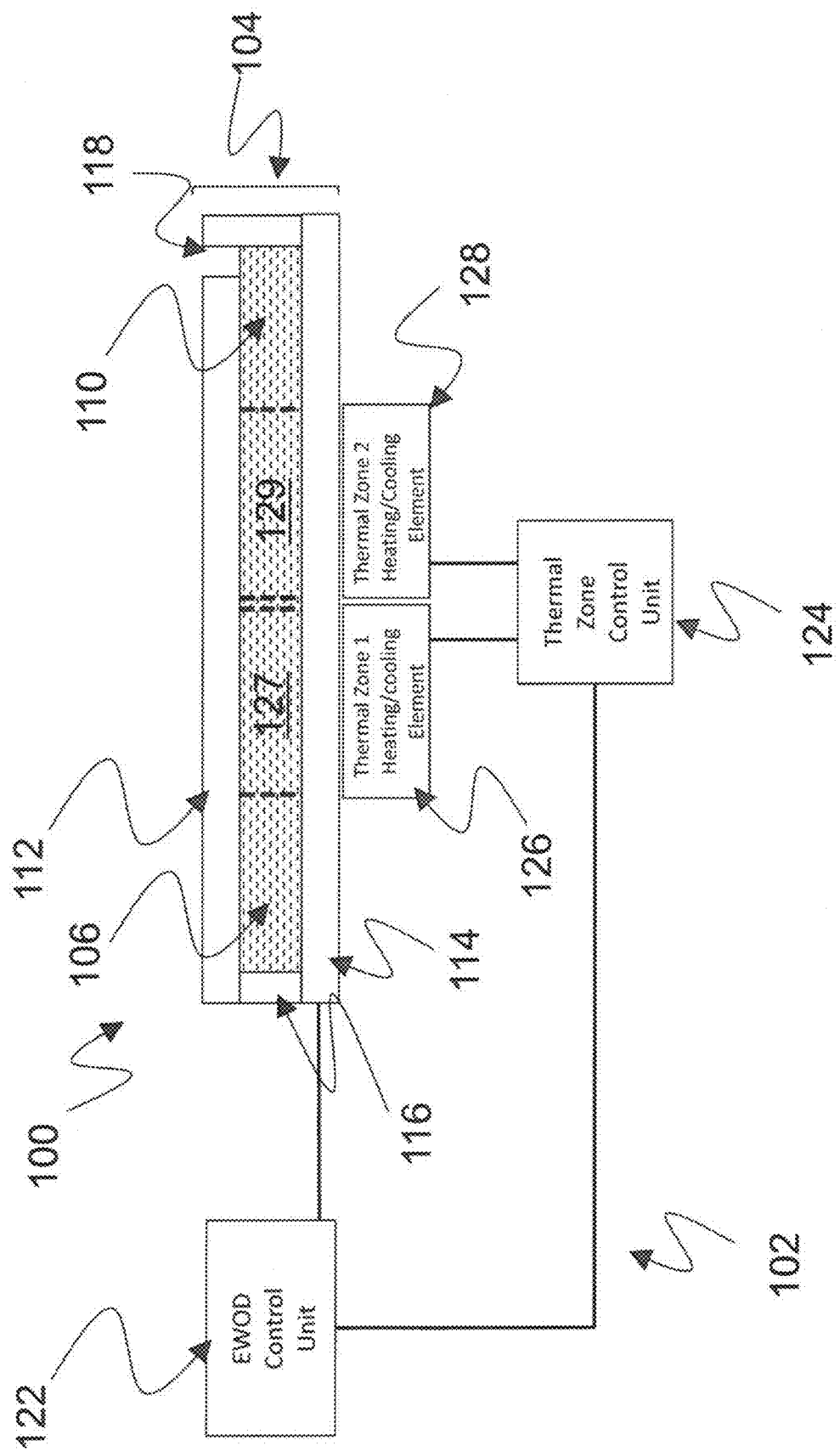
FIG. 8 is a drawing depicting an exemplary microfluidic system in accordance with embodiments of the present invention including thermal control elements.
Figure 9:
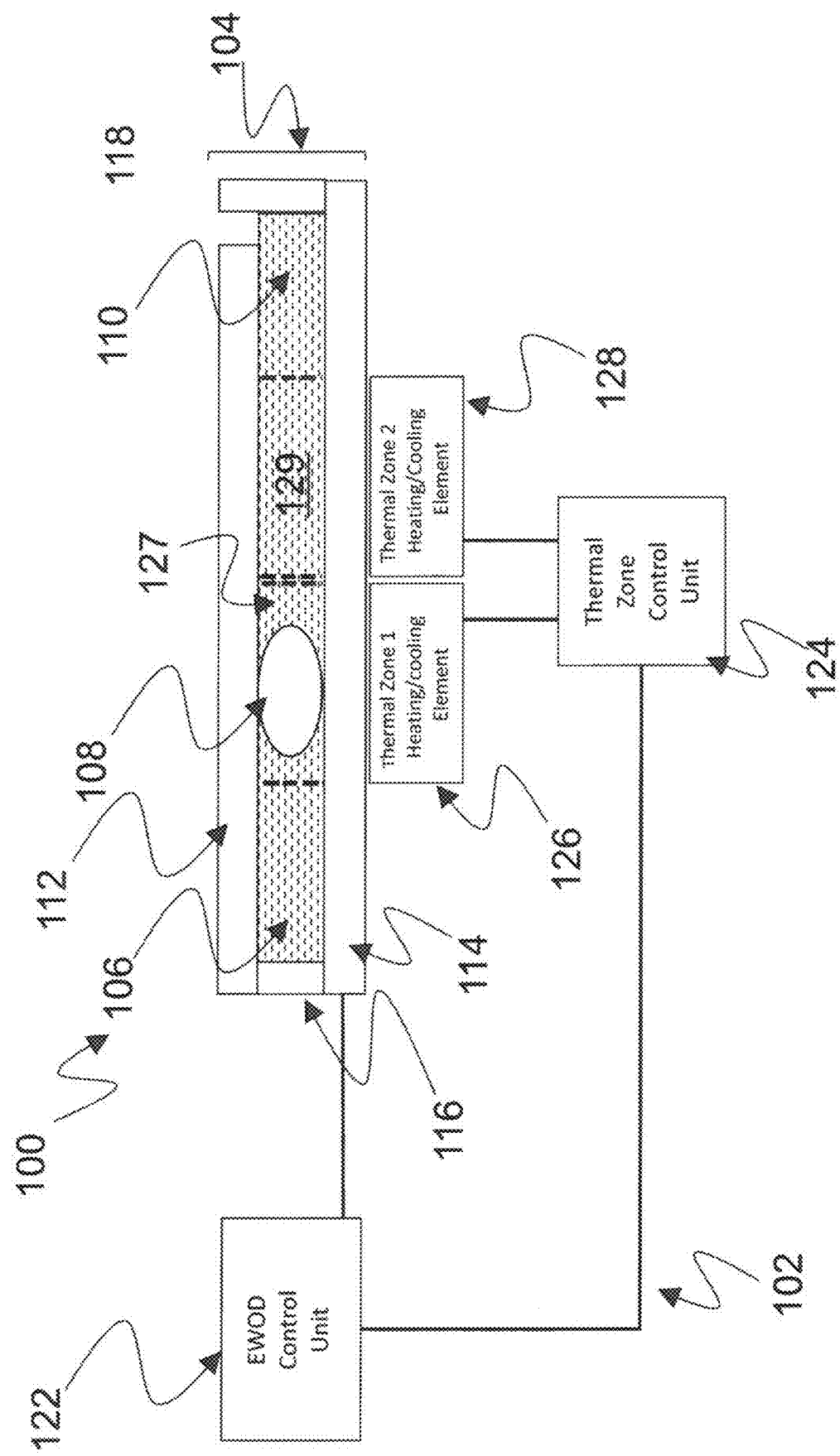
FIG. 9 is a drawing depicting the microfluidic system of FIG. 8 showing an example location of a liquid droplet within the EWOD channel.

FIG. 8 is a drawing depicting an exemplary microfluidic system 100 in accordance with embodiments of the present invention, which includes a control system 102 and an EWOD device 104 (which in particular may be an AM-EWOD device) that defines an EWOD channel 106. FIG. 9 is a drawing depicting the microfluidic system 100 of FIG. 8 showing an example location of a liquid droplet 108 within the EWOD channel 106. A non-polar fluid 110 (e.g. oil) may be used to occupy the volume not occupied by the liquid droplet 108. The EWOD device may include a first (top) substrate assembly 112 and a second (bottom) substrate assembly 114 separated by a spacer 116, which define the EWOD channel 106. For simplicity of illustration of pertinent features, the individual layers of the EWOD device components are omitted. Accordingly, the first and second substrate assemblies may include the associated substrates, insulating layers, electrode layers, and related structures that form the EWOD device, such as for example the various components described with respect to FIGS. 3-7. FIGS. 8 and 9 also show a representative fluid input structure 118 for input of fluid into the EWOD channel. Various configurations of the input structure are known in the art, and therefore any suitable input structure may be employed.

As referenced above, the microfluidic system 100 further includes a control system 102. The control system 102 may be configured comparably as the control system described in connection with FIG. 2, including control electronics that may execute program code embodied as a control application incorporated within a non-transitory computer readable medium or storage device. The control system 102 may include an EWOD control unit 122 that has control electronics and CPU processing devices for controlling the movement of droplets on the EWOD device by the control of actuation voltages applied to the array elements of the EWOD device. The control system 102 further includes a thermal zone control unit 124 and a plurality of thermal control elements. In the depicted example, two thermal control elements 126 and 128 are shown positioned at different spatial locations along the EWOD device. It will be appreciated that any suitable number of a plurality of thermal control elements may be employed in a given device as may be suitable for particular microfluidic operations. The thermal zone control unit 124, similarly as the EWOD control unit 122, contains control electronics and CPU or processing devices, for controlling the temperature of the thermal control elements to generate different temperature control zones within the EWOD device. The control electronics of the thermal zone control unit likewise may similarly execute program code embodied as a thermal control application incorporated within a non-transitory computer readable medium or storage device within the thermal zone control unit.

The thermal control elements 126 and 128 may be capable of actively heating, cooling, or both heating and cooling the EWOD device as required and as determined by the thermal zone control unit 124 in accordance with any desired reaction protocol. Heating and/or cooling may be implemented by any well-known mechanism. For example, heating may be by Joule heating or resistance heating, and cooling may be by means of the Peltier effect as are known in the art for heating and cooling. A region of the EWOD channel 106 within the EWOD device whose temperature is controlled by one of the thermal control elements is referred to herein as a thermal zone. In FIGS. 8 and 9, for example, the first thermal control element 126 is operable to control the temperature of a first thermal zone 127 within the EWOD channel, and the second thermal control element 128 is operable to control the temperature of a second thermal zone 129 within the EWOD channel. Accordingly, the first and second thermal zones 127 and 129 are located at different spatial locations along the EWOD device based on corresponding locations of the thermal control elements. Again, any suitable number of a plurality of thermal control elements may be employed, which would control temperature in a corresponding number of thermal zones located at different spatial locations along the EWOD device.

A liquid droplet assumes a temperature of any thermal zone in which the liquid droplet is located. Because of the minute size of the droplet, rapid temperature equalization occurs as between the liquid droplet and the thermal zone. In the example of FIG. 9, the liquid droplet 108 is located in the first thermal zone 127, and thus would assume the temperature of the first thermal zone 127 as controlled by the first thermal control element 126. By application of appropriate actuation voltages, the liquid droplet 108 may be moved to the second thermal zone 129, and thus would then assume the temperature of the second thermal zone 129 as controlled by the second thermal control element 128.

The EWOD control unit 122 applies actuation voltages to the array elements of the EWOD device to move liquid droplets from one thermal zone to another thermal zone. The thermal zone control unit 124 and EWOD control unit 122 are organized to work together to configure dynamically controlled thermal zones which may vary the temperature in the channel in accordance with the locations of liquid droplets within the channel of the EWOD device. The position of liquid droplets in the EWOD channel may be read out with droplet position sensors (e.g., using the external sensor 35 of FIG. 3 or the droplet sensing circuit 90 of FIG. 7 based on sensing droplet impedance) which may be integrated into the EWOD droplet manipulation device. By combining spatial and temporal control of temperature in the channel of the EWOD device, the temperature profile required for the execution of a given biochemical/chemical reaction or sequence of reactions is optimized, and in turn the number and size of the thermal zones are optimized. The inclusion of the droplet position sensor(s) further enhances the system since feedback control of the droplet position may be used to determine the time at which changes to the temperature of thermal zones are implemented.

The thermal control elements 126 and 128 may be arranged to be in thermal contact with one of the substrate layers of the EWOD device, such as being arranged on either an outer surface or internally as part of the substrate layers of the EWOD device. In the example of FIGS. 8 and 9, the thermal control elements are both located on the outer surface of the second (bottom) substrate 114, although various other configurations of locating the thermal control elements may be employed, as taught in application Ser. No. 15/607,940.

Thermal control of various portions of the EWOD device may be combined with droplet manipulation control of different portions of the EWOD device to perform the methods of the present invention. In exemplary embodiments, the control system operates to apply suitable actuation voltages to pertinent array elements in a suitable sequence at a predetermined time, rate, and duration in accordance with a specified or preset duty cycle, and/or based on actual real time sensed properties of the droplet. In this manner, by using intermittent actuation patterns applied to different portions of the EWOD element array, different droplet manipulation operations may be performed at different portions of the EWOD device array. Details of applying intermittent actuation patterns to different portions of the EWOD device array are described, for example, in Applicant's application Ser. No. 15/475,410 filed on Mar. 31, 2017, the content of which also is incorporated here by reference.

The following definitions are employed in connection with the present EWOD system, device and method:

Sample Droplet: A droplet volume that contains a known or unknown concentration of molecular species of interest; in certain circumstances the sample droplet may not contain any molecular species of interest. The molecular species of interest may be free in solution, attached to a bead or attached to a surface upon which the sample droplet is positioned. In digital assays, some of the sample droplets will contain a molecular species of interest resulting in a positive droplet, while other sample droplets will not contain a molecular species of interest resulting in a negative droplet.

Fluidic Operation: An operation performed on a droplet, or plurality of droplets, via electrowetting forces, e.g. move, split, partition, mix, concentrate, and/or heat.

Extract: Extracting or extracting a portion, or droplet of liquid, from a source volume.

Aspects of the invention are directed to methods of performing digital nucleic acid amplification techniques, including for example digital polymerase chain reaction (PCR) protocols. As illustrative of PCR, the following terms commonly used in connection with PCR reaction protocols are described by ThermoFisher Scientific's Real-time PCR Handbook.

For real-time PCR, also referred to as qPCR, it is recommended that 10-1,000 copies of template nucleic acid are used for each real-time PCR reaction. This is equivalent to ~100 pg-3.3 ng of genomic DNA, or cDNA generated from 1 pg-100 ng of total RNA. The estimation of the concentration of a DNA sample is traditionally performed using a UV absorbance measurement at 260/280 nm. This measurement ratio is well known in the art. A 260/280 ratio of ~1.8 is generally accepted as "pure" for DNA, and a ratio of ~2.0 is generally accepted as "pure" for RNA. The reported low end for quantitation using a microvolume UV spectrophotometer is 2 ng/uL, with samples containing 10 ng/uL of DNA only being read to within 5% of the actual concentration.

Fluorescence based measurements are more sensitive than absorption measurements, and Qubit Fluorimeter is known that quantifies DNA in samples with concentrations as low as 10 pg/uL to within 12% of the actual concentration, with samples containing 10 ng/uL of DNA being accurately read to within 1% of the actual concentration. This is described in Invitrogens' Technical Note on "Comparison of fluorescence-based quantitation with UV absorbance measurements—Qubit fluorometric quantitation vs, spectrophotometer measurements" (2014). A 10 pg/uL DNA sample concentration is the equivalent of approximately $6.2 \times 10^7$ copies/uL assuming a 150 bp dsDNA molecule. For each typical qPCR reaction, DNA starting concentrations are in the region of $1-1 \times 10^6$ copies per uL, preferably between $10-1 \times 10^5$ copies per 20 uL, with qPCR standards for generating standard curves covering the range between 5 and $5 \times 10^4$ copies per uL.

Neither Qubit nor standard UV absorbance measurements are capable of quantifying DNA concentration within the range of $1-1 \times 10^6$ copies per uL. Rather, the DNA must be amplified to a detectable level before an estimation of concentration can be established using these methods. Furthermore, sample volumes between 1-20 uL are required for the quantification of sample concentration on the Qubit and occasionally even larger for UV spectrophotometry. This is significantly greater than the volumes that would be used for concentration quantification using an EWOD platform, e.g. 1-500 nL, leaving more of the sample available for analysis.

The following sets forth definitions as are employed in connection with real-time PCR or qPCR. The definitions are taken from ThermoFisher referenced above.

Baseline: The baseline of a qPCR reaction refers to the low level signal, or noise, in the early PCR cycles when there is little change in the fluorescence intensity, normally between cycles 3 to 15.

Threshold: The baseline is set above this "background" but not so high that it includes a statistically significant increase over the baseline signal. Real-time PCR systems usually automatically set the threshold value to 10 times the standard deviation of the baseline fluorescence. However, the value of the threshold can be set to any point in the exponential phase of PCR.

Threshold Cycle (Ct): The threshold cycle, Ct, is the PCR cycle number where the fluorescence intensity crosses the threshold. The Ct value is used to calculate the initial concentration of nucleic acid in a sample because the Ct value is inversely proportional to the starting concentration. Assuming that a reaction is 100% efficient, a 10-fold dilution series will have Ct values that are ~3.32 cycles apart.

Standard Curve: A dilution series of known initial template nucleic acid concentrations can be used to establish a standard curve which then enables the concentration of a sample with an unknown nucleic acid concentration to be calculated. Standard curves typically plot the Ct value on the y-axis and the Starting Quantity of DNA or RNA on the x-axis. The slope, y-intercept and correlation coefficient values provide information about the performance of the PCR reaction.

Efficiency: A PCR efficiency of 100% corresponds to a slope of −3.32 in the standard curve as governed by Eqns. 1a and 1b below. An amplification efficiency of 2, or 100%, means that the template nucleic acid doubles after each thermal cycle.

$$\text{Efficiency} = 10^{(-1/slope)} \qquad \text{(Eqn. 1a)}$$

$$\% \text{ Efficiency} = \left(10^{\left(-\frac{1}{slope}\right)} - 1\right) \times 100 \qquad \text{(Eqn. 1b)}$$

Y-intercept: The y-intercept in the standard curve corresponds to the theoretical limit of detection of the reaction. While it is theoretically possible to detect a single copy of a target using qPCR, copy numbers in the range of 2-10 are more frequently specified as the lowest level that can be reliably quantified.

The following definition is employed in connection with isothermal nucleic amplification techniques:

Time to Positive (Tp): The time at which the fluorescence intensity crosses the threshold. Typically, threshold values are set to 10 times the standard deviation of the baseline fluorescence, but can be set to any point in the amplification phase.

More generally, 'Turn-on' refers to the point at which the fluorescence crosses a threshold value, usually ~10 times the standard deviation of the baseline fluorescence, and can mean either the Threshold Cycle (Ct) or Time to Positive (Tp) depending on the type of amplification assay being performed. Ct and Tp values correspond to a concentration of molecules per volume, therefore 'turn-on' can also be defined as copies of molecules per volume, e.g. copies/20 uL, copies/uL and/or copies/partition.

Figure 10:
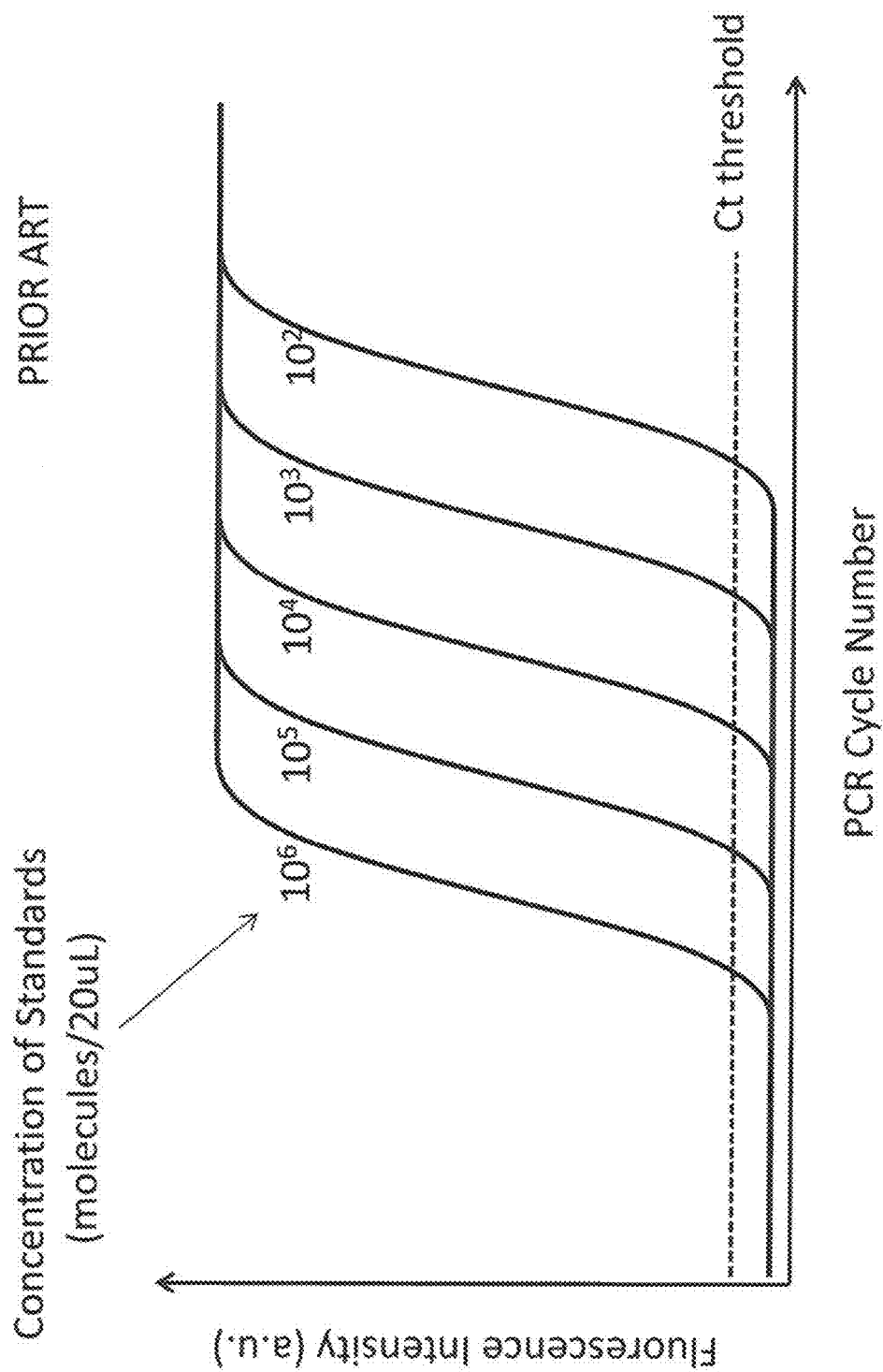
FIG. 10 is a graph depicting amplification curves for an example series of standards from $10^6$ to $10^2$ copies per 20 ul.
Figure 11:
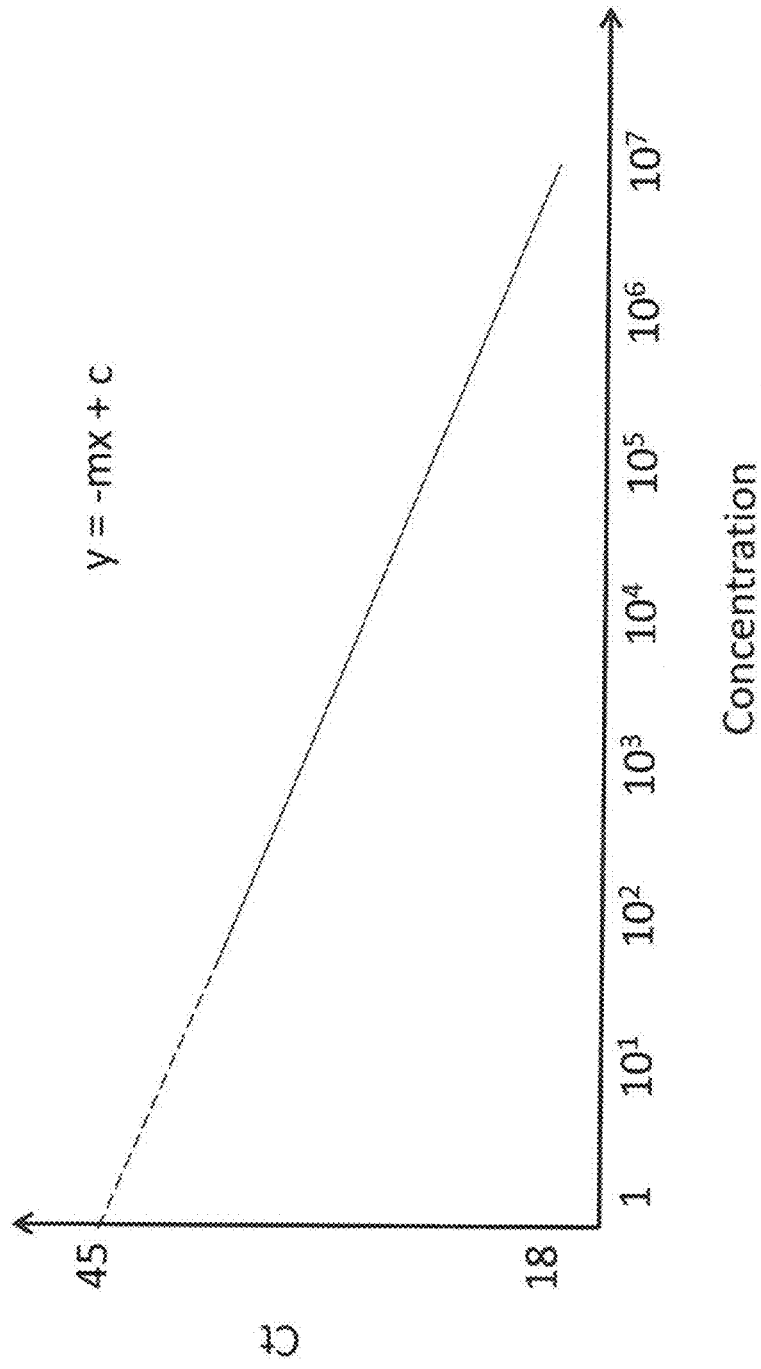
FIG. 11 is a drawing depicting an example standard curve for the amplification curves of the series of FIG. 10.

A typical set of amplification curves using a series of standards from $10^6$ to $10^2$ copies per 20 ul is shown in FIG. 10, with an example standard curve shown in FIG. 11. A standard curve typically has the format:

$$y = -mx + c \qquad \text{(Eqn 2)}$$

where m is the gradient of the line, c is the y-intercept, x is the log of sample concentration and y is the Ct value.

In order to obtain quantitative or semi-quantitative data from PCR (qPCR) a set of calibrated standards must be run alongside the sample. Without a sufficient set of standards in every experiment, only an approximation of sample concentration can be made. This is due, in part, to batch to batch variability of PCR reagents.

For optimum PCR, a reaction mixture must cycle through three discrete temperatures typically 35 to 45 times. An exemplary reaction protocol may include process steps performed, for example, at 95° C. to denature the double stranded DNA; 55-60° C. to anneal the primers to ssDNA; and 70-75° C. for optimum extension of the new DNA strand. In some examples, it is possible to cycle the PCR reaction mixture typically 35 to 45 times between 95° C. to denature the double stranded DNA, and 55-60° C. for both the anneal and extension steps.

Primers are short strands of DNA approximately 18-22 base pairs long. They are used as a starting point for DNA replication, and they define a region of interest, or target, on the template DNA strand for amplification. Different primers can be used to amplify different targets, or regions of interest, within a DNA sample. In traditional qPCR 96-well plate experiments, a DNA sample is pipetted into each of the 96 wells and different target primers are pipetted into each well so that a single DNA sample can be screened against up to 96 different targets.

A PCR ready droplet, or a PCR sample droplet, typically contains all the reagents required for a DNA sample to be amplified. A reaction may include mastermix, primer(s), probe(s) and the DNA sample to be amplified. A control droplet, or one that does not contain any DNA sample, typically contains all the reagents required for a nucleic acid to be amplified but without any sample. A control droplet may include mastermix, primer(s) and probe(s).

Instead of starting with DNA, it is possible to start with RNA and perform reverse-transcription to generate complementary DNA which can then be amplified. Reverse-transcription PCR can be performed either as a single-step or two-step process.

In contrast to reaction protocols that include reaction steps at different temperatures, isothermal reaction protocols for nucleic acid amplification alternatively may be performed. Isothermal amplification techniques exist by which DNA amplification is performed at a fixed temperature rather than thermally cycling a sample many times between 95° C. and 60° C. as used in traditional PCR. Common isothermal techniques include recombinase polymerase amplification (RPA), loop-mediated isothermal amplification (LAMP), strand displacement amplification (SDA), helicase-dependent amplification (HAD), and nicking enzyme amplification reaction (NEAR).

The systems and methods of the present invention may be combined with any suitable readout format as are known in the art. Readout mechanisms may include intercalating dyes, hydrolysis probes and hybridization probes. The instruments may be designed to be compatible with a single optical wavelength, or include multiplexing capabilities in which two or more different wavelengths can be excited, detected and monitored. Intercalating dyes include, but are not limited to, SYBR Green I, LC Green, LC Green Plus, Resolight, EvaGreen, Chromofy, and SYTO 9. Common fluorophores for hydrolysis probes include, but are not limited to, FAM, JOE, VIC, HEX, TAMRA, Cy3.5, Cy5 and ROX. Common donor/acceptor pairs for hybridization probes include, but are not limited to, Fluorescein/Tetramethylrhodamine, IAE-DANS/Fluorescein, EDANS/Dabcyl, Fluorescein/QSY7, and Fluorescein/QSY9 dyes.

Digital PCR absolutely quantifies a sample by dividing the sample into a number of partitions, and uses discrete Poisson statistics to calculate the concentration based on the number of partitions that amplify, referred to as positive partitions, versus partitions that do not amplify, referred to as negative partitions.

The Poisson distribution, in the context of digital assays, gives the probability, p, that there are k target molecules in a given partition based on an average concentration per partition, v.λ, where v is the partition volume (uL) and λ is the bulk concentration (molecules/uL).

$$p = \frac{((v \cdot \lambda)^k e^{-(v \cdot \lambda)})}{k!} \qquad \text{(Eqn. 3)}$$

In digital PCR, any partition that has k>0 molecules is identified as being positive. If k=0, then Eqn. 3 simplifies to Eqn. 4 to give the probability p that a given partition will not contain any target molecules and the partition is negative.

$$p = e^{-(v \cdot \lambda)} \qquad \text{(Eqn. 4)}$$

In systems in which each partition has the same volume, the number of negative partitions, b, out of the total number of partitions, n, can be used as an estimate for p, so expected results can be estimated from known concentrations (Eqn. 5), or observed results can be used to calculate expected concentrations (Eqn. 6).

$$b = n \cdot e^{-(v \cdot \lambda)} \qquad \text{(Eqn 5)}$$

$$\lambda = \frac{-\ln\left(\frac{b}{n}\right)}{v} \qquad \text{(Eqn 6)}$$

The following definition is employed in connection with the present EWOD system, device and method:

Digital Quantification: Identifying which partitions, from a plurality of partitions, are positive for a molecular species of interest and which are negative. The number of positive and/or negative partitions can be counted. Digital quantification can be used to calculate the concentration of a sample, using discrete Poisson statistics, based on the number of partitions that are positive and the number of partitions that are negative.

Figure 12:
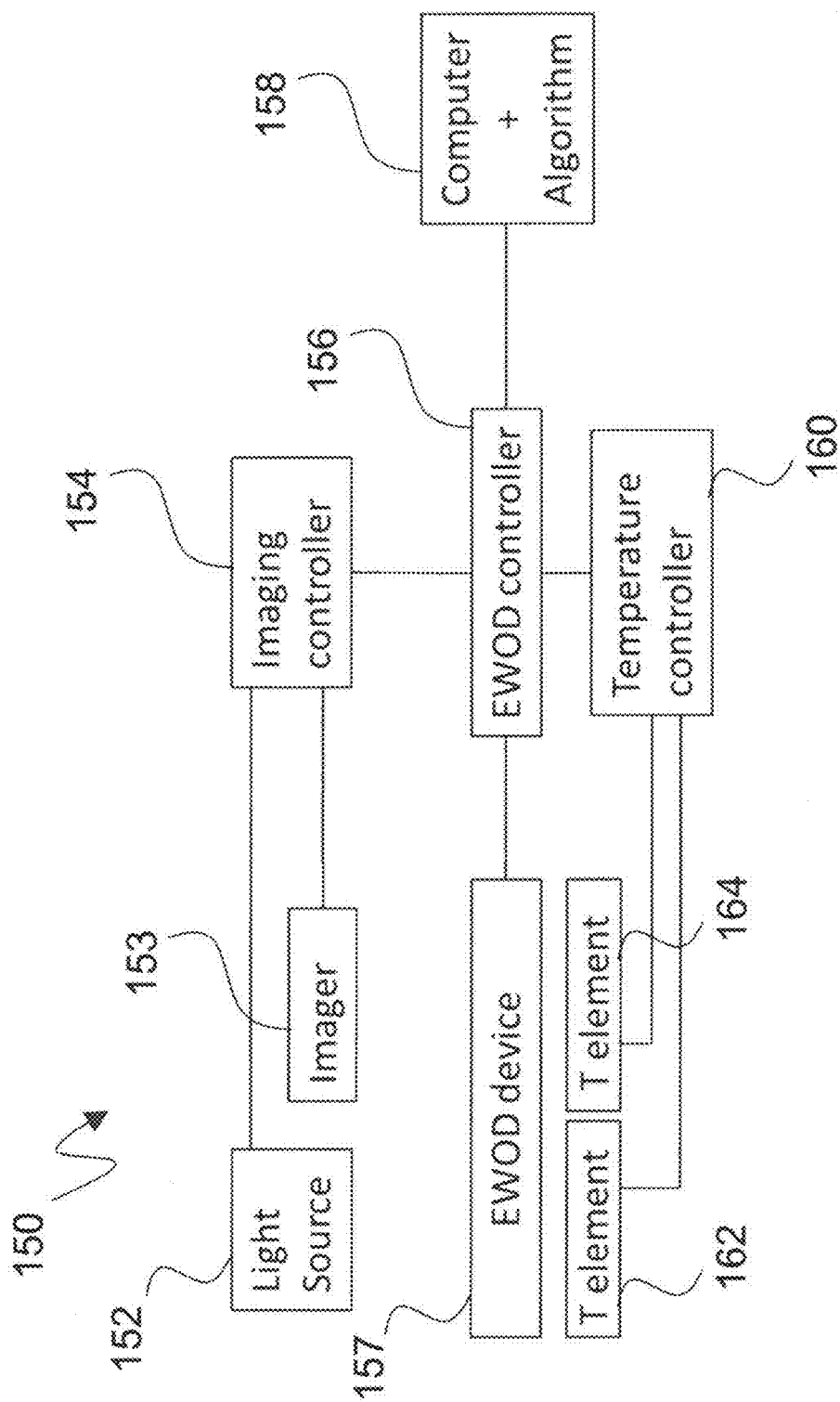
FIG. 12 is a drawing depicting an exemplary digital nucleic acid amplification system in accordance with embodiments of the present invention.

FIG. 12 is a drawing depicting an exemplary digital assay amplification system 150 in accordance with embodiments of the present invention. To make the fluorescence measurements, the system 150 may include a light source 152 for emission of the measurement light as referenced above, and an imager 153 for detecting received light from the reaction droplets for performing the fluorescence measurements as is known in the art. The operation of the light source and imager may be controlled and analyzed by an imaging controller 154.

The light source, imager, and imaging controller may be combined with a microfluidic system to perform the digital nucleic acid amplification, such as for example digital PCR. The microfluidic system may be configured as an EWOD or AM-EWOD based system in accordance with the systems described with respect to FIGS. 2-9 above. For general reference as shown in FIG. 12, the microfluidic system may include an EWOD controller 156 that may be configured comparably as the control system described above, which controls actuation of an array of electrowetting elements incorporated into and EWOD device 157. As part of the control application incorporated into such controller, a computer and algorithm 158 for performing the amplification operations may be provided and stored within a non-transitory computer readable medium or storage device. The computer and algorithm 158 may also store the target turn-on values, reference or target turn-on values, standard curve data and/or calibration curve data. Such values can be accessed, stored, and/or inputted as necessary. These turn-on values can be accessed by the system to assist in the calculation of dilution factors as required. The microfluidic system further includes a temperature controller 160 and a plurality of thermal control elements (T-elements). In the depicted example, two thermal control elements 162 and 164 are shown, but again it will be appreciated that any suitable number of a plurality of thermal control elements may be employed in a given device as may be suitable for particular microfluidic operations. The temperature controller 160 contains the control electronics and CPU or processing devices, for controlling the temperature of the thermal control elements to generate different temperature control zones within the EWOD device as referenced above and described in application Ser. No. 15/607,940. In addition, although the imaging controller 154, EWOD controller 156, computer and algorithm 158, and temperature controller 160 are illustrated as separate elements in FIG. 12, it will be appreciated that multiple control components may be combined into a single control system component.

Figure 13B:
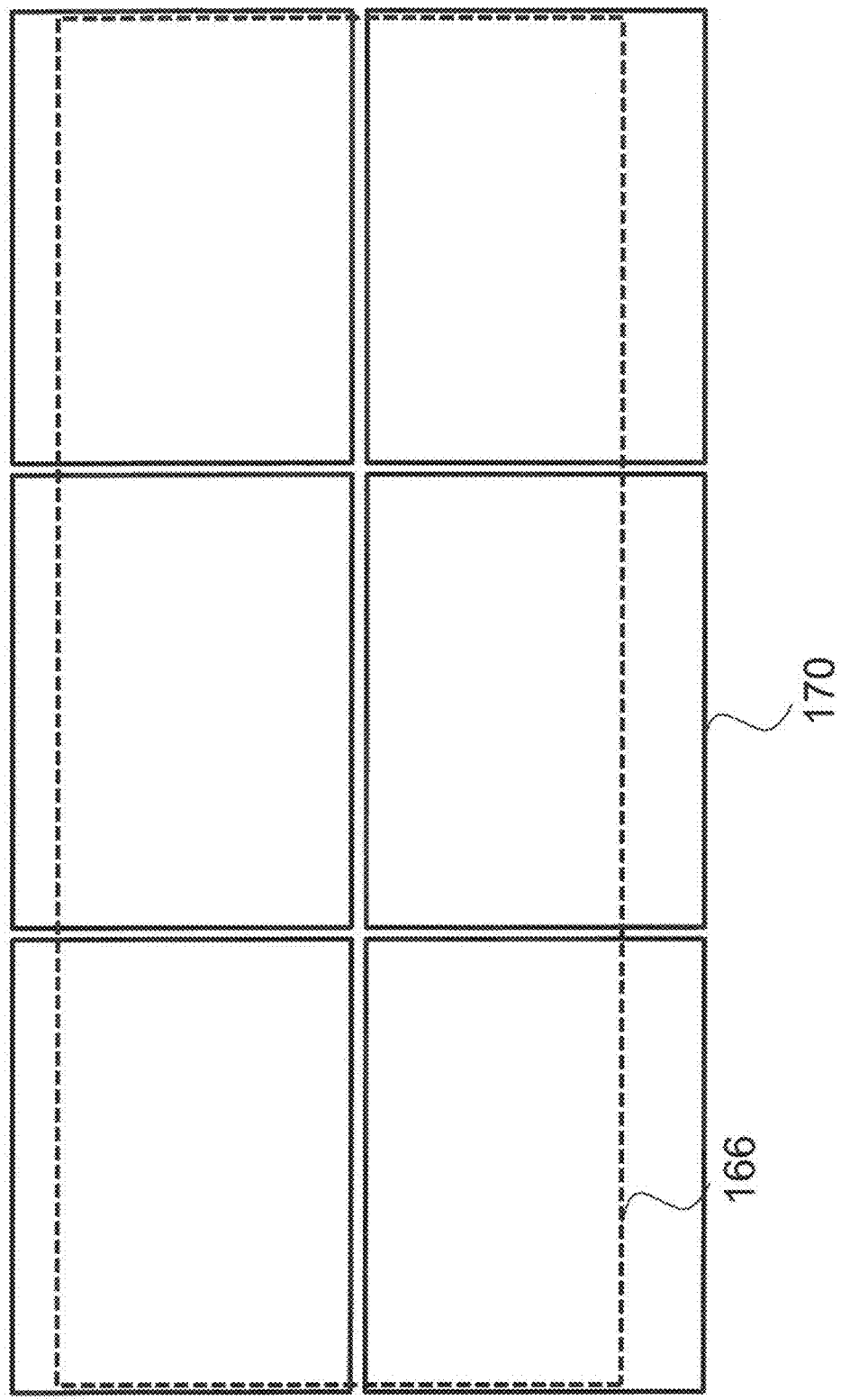
Figure 13C:
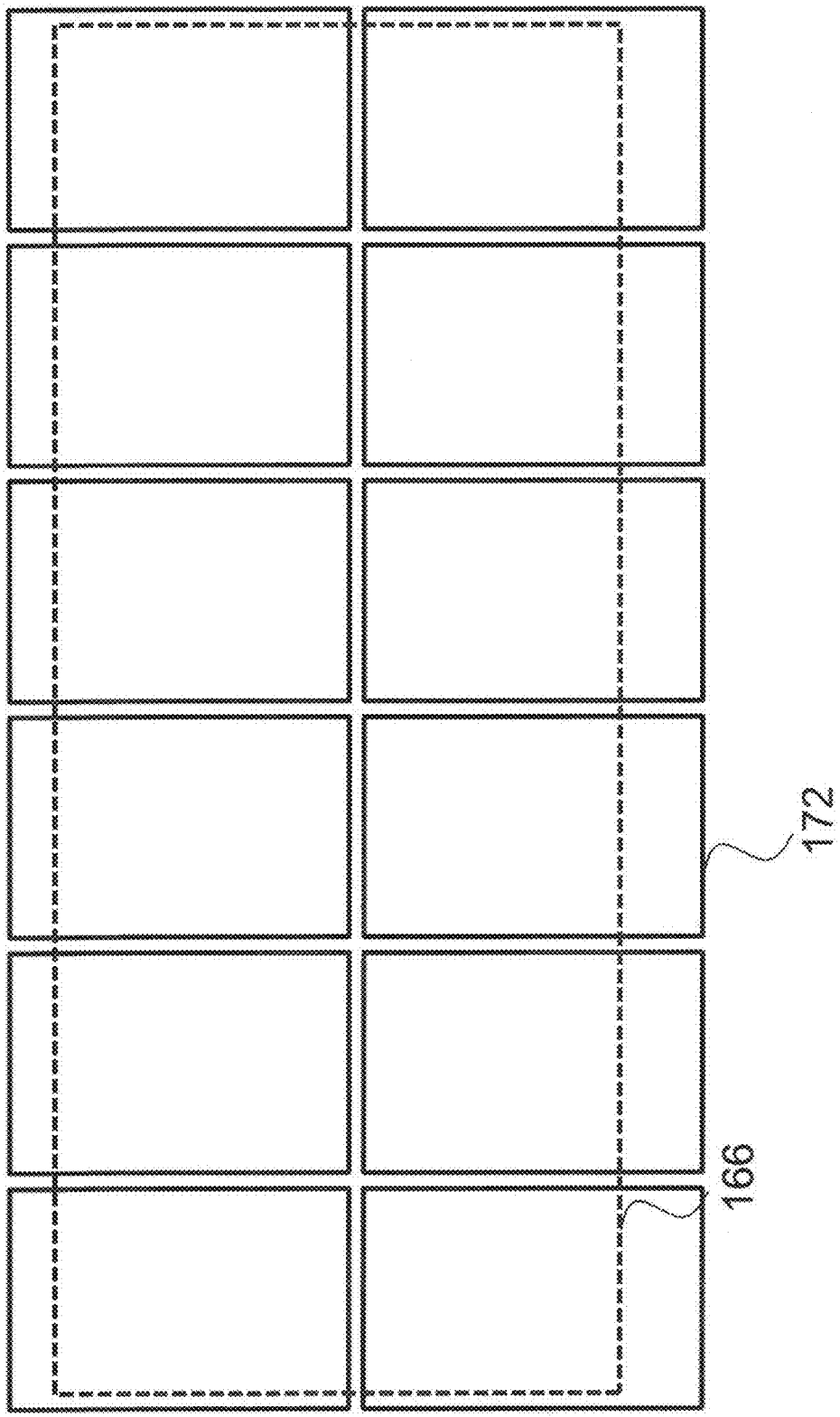

FIGS. 13A-13C are drawings depicting different exemplary configurations of thermal control elements to generate multiple temperature zones in the EWOD device. In these examples, an EWOD cartridge 166 containing an EWOD array of actuation elements is represented in block form as delineated by the dotted line. The solid lines delineate the positioning of multiple thermal control elements, whereby each thermal control element may be employed to generate a corresponding temperature zone in a portion of the EWOD array. In the example of FIG. 13A, there are three thermal control elements 168 that correspond to three temperature zones in the EWOD array of the cartridge 166; in the example of FIG. 13B, there are six thermal control elements 170 that correspond to six temperature zones in the EWOD array; in the example of FIG. 13C, there are twelve thermal control elements 172 that correspond to twelve temperature zones in the EWOD array. The number of thermal control elements and resultant thermal control zones represents a tradeoff between the precision of temperature control versus the complexity of the device, and any suitable number of thermal control elements may be employed.

The exemplary methods of digital PCR described below employ the 12-element configuration of FIG. 13C as illustrative.

In the exemplary reaction protocols for digital nucleic acid amplification, including digital PCR, described below, the following is an example set of parameters associated with the EWOD device configuration and operation. It will be appreciated that the following is illustrative and may be adjusted as would be suitable to particular circumstances. A typical EWOD device may have 316×130 TFT pixels, where each TFT pixel is 210 um×210 um and the cell gap is 130 um. This is the equivalent of 41,080 pixels, and thus such an EWOD device can accommodate a maximum volume of ~235 uL of droplets. Usable droplet sizes, for example, may be 1×1, 2×1, 2×2, or 3×3 pixels or comparable, and there may be allotted a gap between droplets of two to three pixels. From these droplet arrangements and the size of the EWOD array, one can then calculate the number of droplets and the volume of each partition associated with the digital amplification protocol. In addition, embodiments of the present invention predominantly are described with respect to employing the PCR and digital PCR amplification techniques, although the present invention is not limited to such techniques and can be used with a wide variety of nucleic acid amplification techniques. Other suitable amplification techniques include isothermal amplification techniques.

Figure 14A:
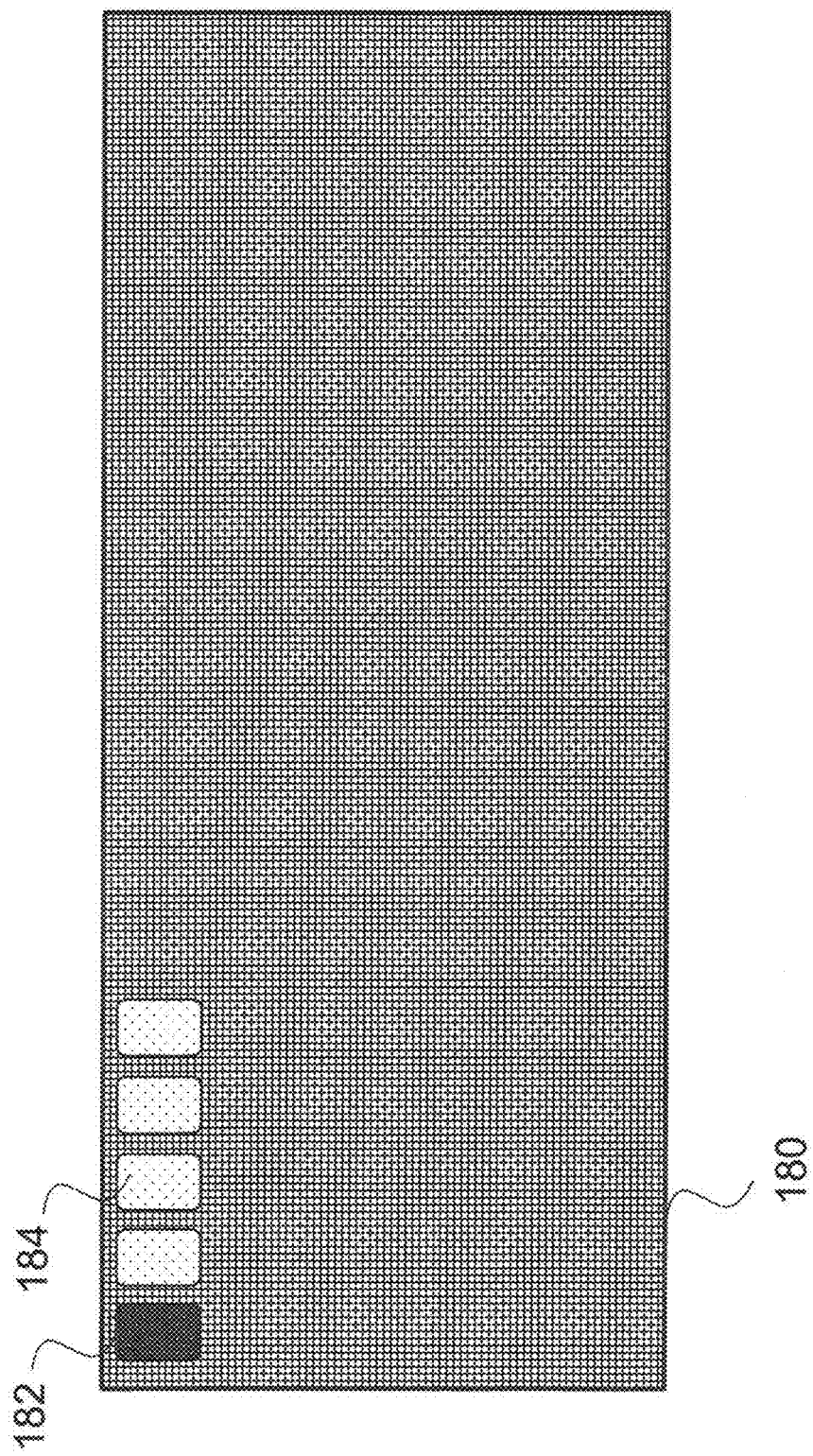

FIGS. 14A-14I are drawings depicting a progression of steps constituting an exemplary method of performing a digital PCR reaction protocol in accordance with embodiments of the present invention. FIG. 14A illustrates an initial preparation of an EWOD cartridge 180 in a simplified fashion for purposes of illustration. It will be appreciated that the EWOD cartridge 180 would have a structure comparable to the embodiments of the EWOD devices described above.

Figure 14C:
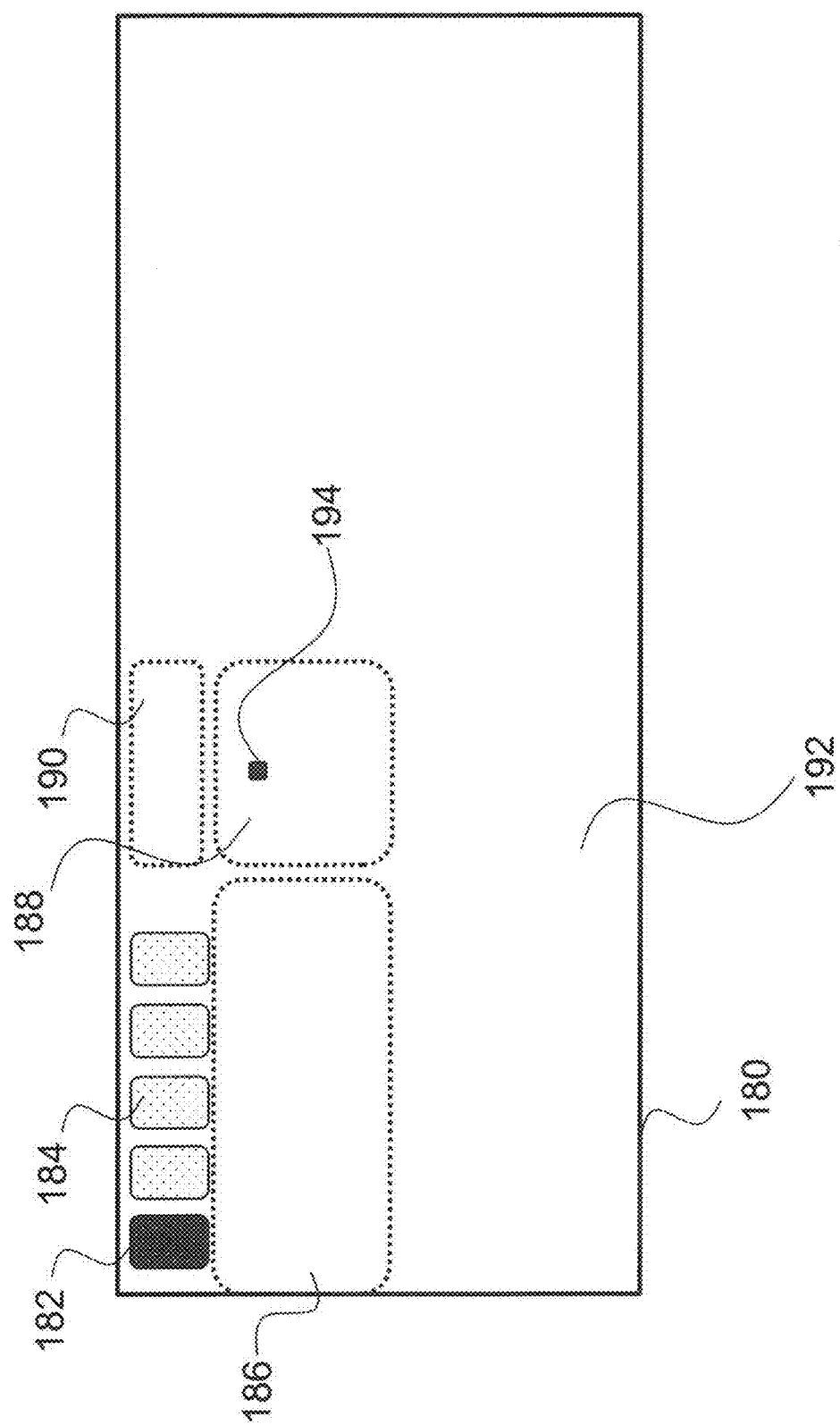

Generally, as further detailed below, in a complete digital PCR reaction protocol, a first portion of the reaction protocol is to determine an appropriate dilution factor for a first sample droplet, as illustrated with respect to FIGS. 14B-14F. A second portion of the reaction protocol is then to utilize the calculated dilution factor to dilute a second sample droplet, and perform digital PCR by partitioning the diluted sample droplet, as illustrated in FIGS. 14G-14I. In addition, although the digital amplification process is described below principally in connection with PCR amplification processes, it again will be appreciated that comparable principles may be employed to perform digital amplification and analysis using alternative amplification processes other than PCR, including for example isothermal amplification processes.

With the example of FIGS. 14A-14I, FIG. 14A is a drawing depicting the EWOD cartridge 180 including an EWOD array into which there have been inputted a sample volume 182 and four diluent volumes 184. An example sample volume 182 includes the nucleic acid sample (e.g., DNA) having a target portion to undergo the amplification process, primers, probe(s) and mastermix. The diluent volumes 184 may be used to dilute the sample volume as further described below, and include primers, probe(s) and mastermix at the same concentration as in the sample volume 182 but lacking the nucleic acid sample. FIG. 14B is a drawing depicting how the EWOD cartridge 180 can be operated to generate different actuation zones for different stages of the digital PCR reaction protocol. The different actuation zones may include a sample preparation zone 186, a first nucleic acid amplification zone 188, and a waste zone 190. The EWOD cartridge 180 further can be operated to generate a digital amplification zone 192 where for example digital PCR may be performed. The different zones may be generated by actuating different groups of EWOD elements during the different stages of digital PCR reaction protocol, and the operations performed in each zone are described below as the different steps in the digital PCR reaction protocol are described.

In a first step of the reaction protocol as shown in FIG. 14B, the electrowetting operation of the EWOD cartridge 180 is used to extract a first sample droplet 194 from the sample volume 182 into the sample preparation zone 186. In this particular example, generating the first sample droplet 194 from the sample volume 182 amounts to the entirety of the sample preparation operations (additional preparation operations may be performed as shown in examples below). As no further sample preparation is required at this stage, in a second step of the reaction protocol the sample droplet 194 is moved into the first amplification zone 188, as shown in FIG. 14C.

Figure 14D:
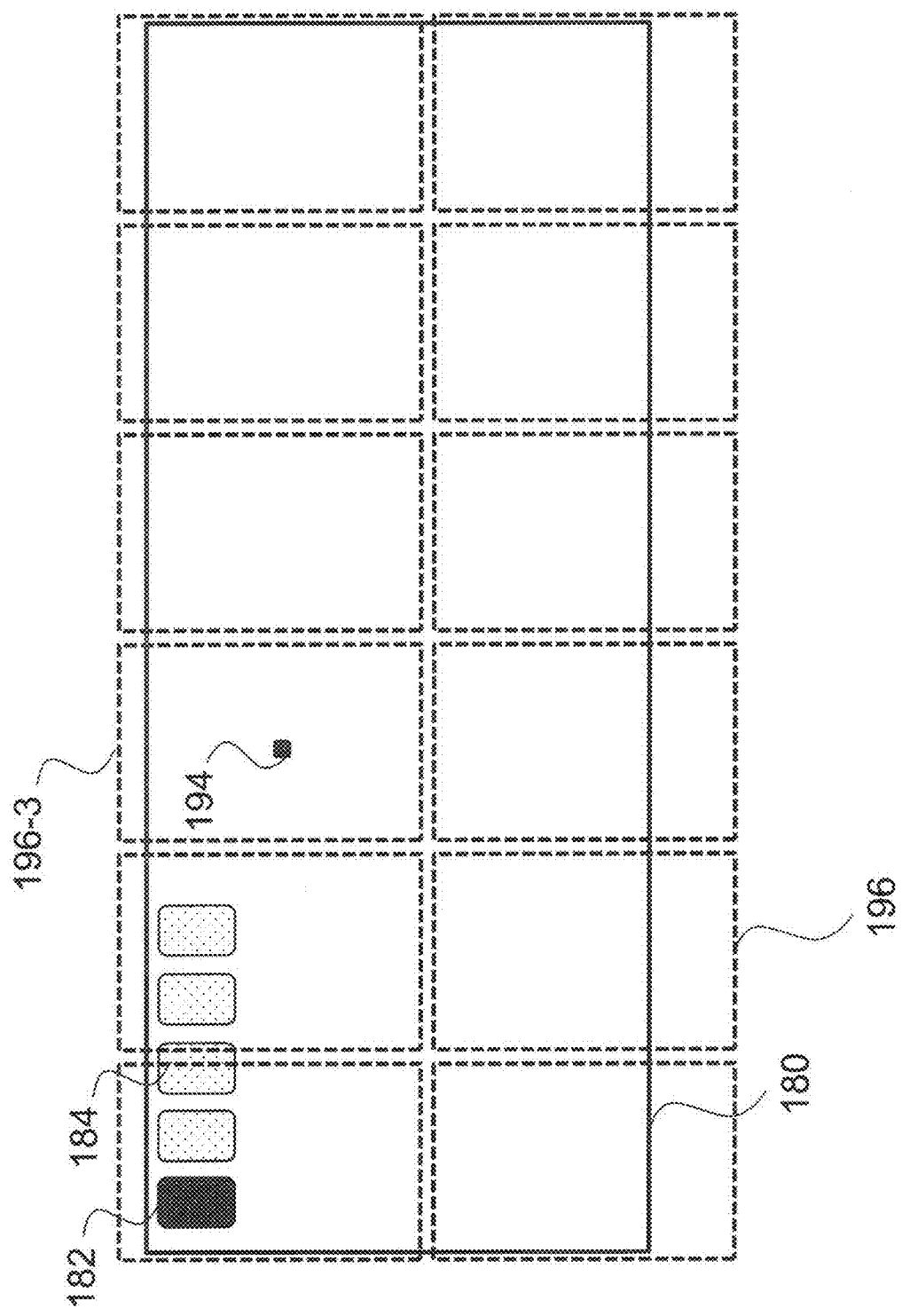

FIG. 14D is a drawing depicting the exemplary EWOD cartridge 180 with the EWOD array overlaid onto a plurality of thermal control elements 196. This example employs the 12-element configuration described above with respect to FIG. 13C. If the first row of thermal control elements is denoted elements 1-6, and the second row of thermal control elements is denoted elements 7-12, then the first amplification zone 188 is positioned in correspondence with thermal control element number three, identified in FIG. 14D as element 196-3. In a third step of digital PCR, an amplification process may be performed as to the first sample droplet 194 within the first amplification zone 188. Because the sample droplet 194 is positioned above thermal control element 196-3, such thermal control element can be independently controlled to cycle the sample droplet 194 between 95° C. and 60° C. to perform a PCR amplification process. Each time the thermal control element 196-3 (and therefore the sample droplet 194) is cooled to 60° C., a fluorescence image is taken and the thermal cycling process continues until the fluorescence value is greater than a pre-defined threshold, which permits determination of the threshold cycle Ct. The number of cycles may vary and need not require the full 35-45 cycles common in PCR, and the thermal cycling can stop as soon as the Ct value can be calculated. The remaining thermal zones, i.e., the thermal zones corresponding to the thermal control elements other than 196-3, may be kept at the optimal temperature for any reagents within a given thermal zone, or can remain at room temperature.

Figure 14E:
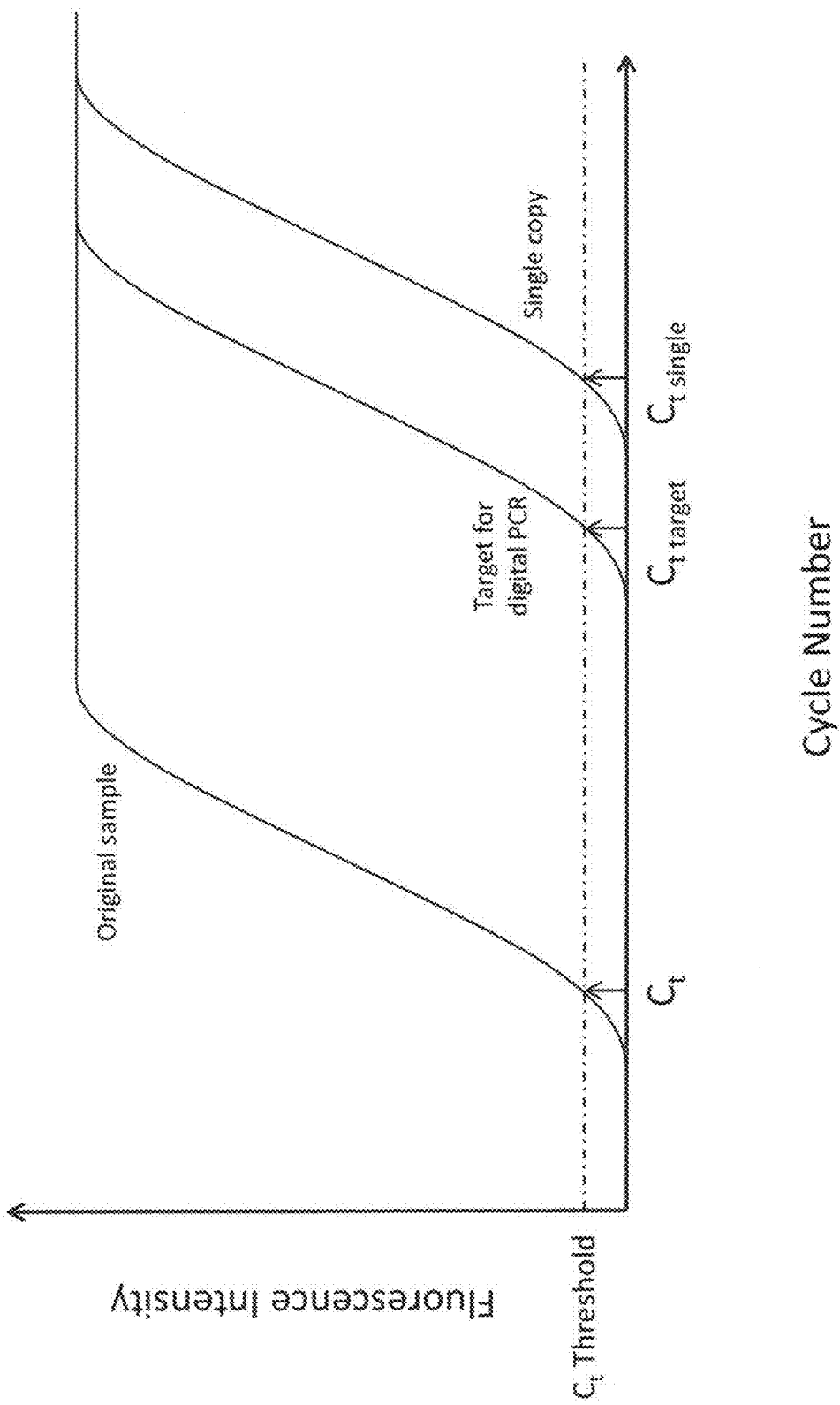
Figure 14H:
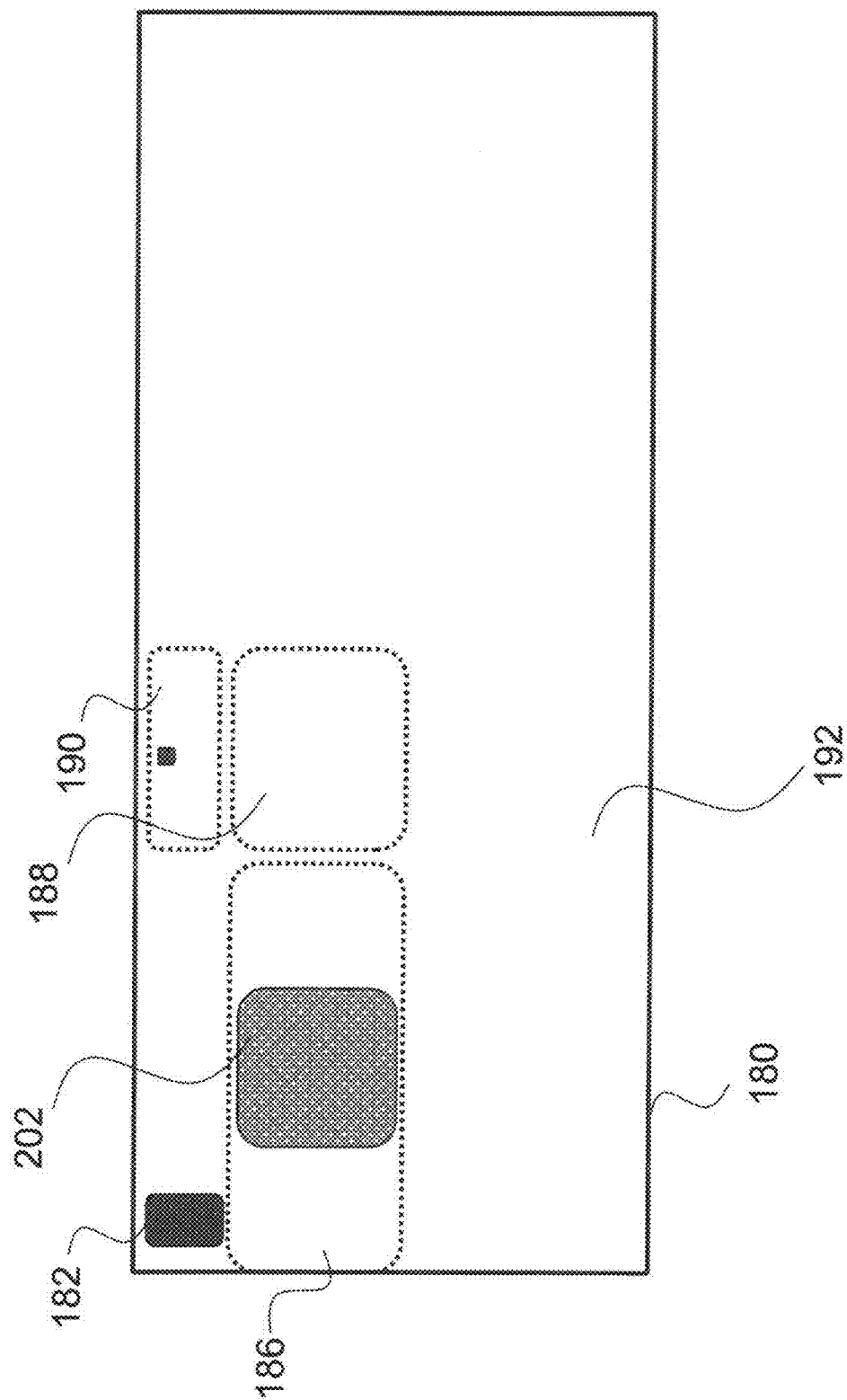
Figure 14I:
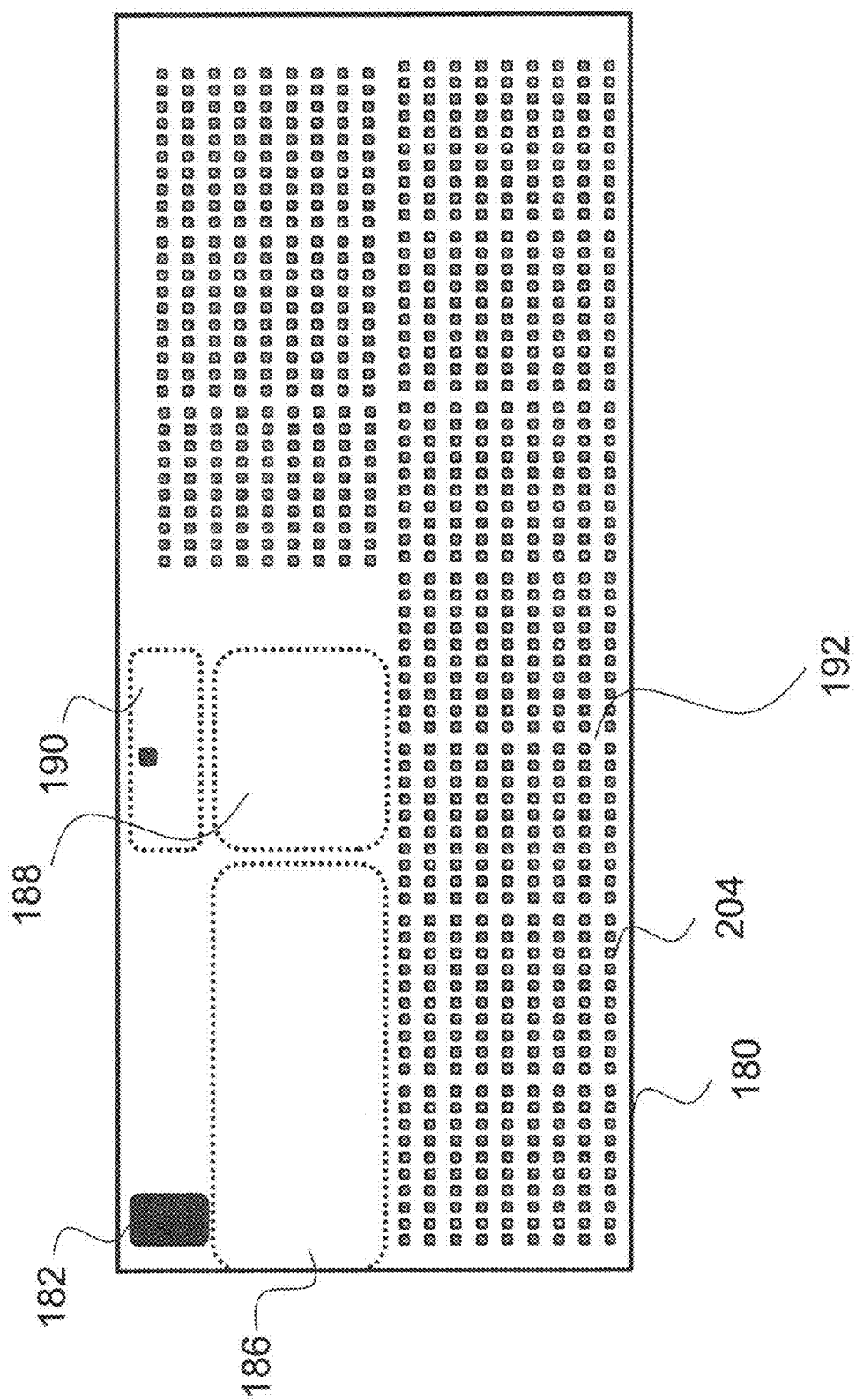

FIG. 14E is a graph depicting an example of a fluorescence intensity curve that illustrates representative calculations associated with this example. As known to those of ordinary skill in the art, the fluorescence intensity curve constitutes a relationship of fluorescent intensity as a function of cycle number for the sample, and is used to determine the turn-on value at which the DNA in the sample droplet is detectable via the fluorescence measurements. The target turn-on value, $Ct_{target}$, is the bulk volume turn-on value identified to support subsequent digital PCR quantification when the bulk volume is partitioned. The target turn-on value, $Ct_{target}$, and the threshold fluorescence for a single copy, $Ct_{single}$, can be saved values generated from prior experimentation, and/or can be derived from the experiment being performed. The fluorescence intensity curve for the sample droplet also is plotted, from which the Ct value for the sample droplet is determined. Once the Ct value has been determined through the fluorescence intensity curve for the sample droplet, the concentration of the sample droplet can be estimated by inputting the Ct value into a reference standard curve equation (such as that comparable to FIG. 11) for the reaction saved on the systems' computer. The dilution factor can be calculated by comparing the sample concentration to the target sample concentration that will support subsequent digital PCR quantification when the sample is partitioned, using Eqn. 7.

$$\text{Dilution Factor} = \text{Efficiency}^{(Ct_{target} - Ct)} \qquad (\text{Eqn. 7})$$

For a reaction that is 100% efficient, the "Efficiency" term in Eqn. 7 is 2.

Ct values correspond to a concentration, e.g. number of copies/20 ul. The target turn-on value, $Ct_{target}$, is calculated using knowledge of (a) the number of partitions the system will use for digital quantification, (b) the volume of each of those partitions and (c) knowledge that the optimal concentration range for digital PCR quantification is equivalent to ~0.7-1.6 copies per partition. Once in the digital regime, the turn-on for each partition that contains a single copy of DNA will be $Ct_{single}$.

For example, assume a sample has a bulk concentration of 1000 copies per 20 ul with a turn-on value Ct. The system is designed to perform a digital quantification assay using 100 partitions, each 0.2 ul in volume. Taking the optimal concentration range for digital quantification to be ~0.7-1.6 copies per partition, it is possible to calculate that the bulk volume will need to have between (0.7*100=) 70 and (1.6*100=) 160 copies per 20 ul. Setting the target concentration to 1 copy per partition, the target bulk volume concentration will be equivalent to (1*100=) 100 copies per 20 ul. Therefore, the original sample has to be diluted 10-fold in order to reduce the concentration from 1000 copies per 20 ul to 100 copies per 20 ul. The diluted sample will have a turn-on value of $Ct_{target}$. The diluted sample is then partitioned into 100 partitions. Poisson statistics can be used to calculate that 63 out of the 100 partitions will be positive, and of those partitions that contain a single DNA molecule, the turn-on value will be $C_{tsingle}$.

It will be appreciated that the microfluidic system of the present invention is fully automated. Accordingly, the electrowetting operations and requisite calculations are all performed by the control system and computer without requiring user intervention.

As shown in FIG. 14F, the first sample droplet 194 as amplified using PCR is then moved into waste zone 190, from which the sample droplet 194 can be removed from the EWOD cartridge 180. The temperature of the third thermal control element 196-3 may then be returned to the same temperature as the other thermal control elements, preferably a temperature between 15-25° C.

Accordingly, FIGS. 14B-14F illustrate a first portion of a digital PCR reaction protocol, by which an appropriate dilution factor is determined automatically by the system. FIGS. 14G-14I illustrate a second portion of the reaction protocol, by which this dilution factor subsequently is employed by the system, again automatically to perform the digital nucleic acid amplification, such as for example digital PCR.

FIG. 14G is a drawing depicting a sample preparation step of digital PCR using the EWOD cartridge 180. In particular, the electrowetting operation of the EWOD cartridge 180 is used to extract a second sample droplet 198 from the sample volume 182 into the sample preparation zone 186, alongside a diluent droplet 200 generated from one or more of the diluent volumes 184. The diluent droplet 200 is generated to be of a volume sufficient for diluting the second sample droplet 198 by the dilution factor calculated using Eqn. 7. As illustrated in FIG. 14H, electrowetting forces are used to the mix the second sample droplet 198 and the diluent droplet 200 into a diluted sample droplet 202 within the sample preparation zone 186, using a combination of requisite droplet manipulations, such as for example moving, pulsing, kneading, splitting and re-merging droplet manipulation techniques.

As illustrated in FIG. 14I, once the diluted sample droplet 202 has been fully mixed, the diluted sample droplet 202 can be split via electrowetting forces into a plurality of partitions 204 capable of quantifying the diluted sample droplet 202 by digital nucleic acid amplification, such as digital PCR. The optimal concentration for digital nucleic acid amplification is typically ~0.7-1.6 copies per partition. The sample is split into a number of partitions 204, and the partitions are moved into the digital amplification zone 192. The digital amplification zone 192 preferably excludes the first amplification zone 188 so that any possible contamination issues can be avoided. In a preferred embodiment, all of the diluted sample droplet 202 will be split into partitions 204 for quantification. Thermal control elements 4-12 of the thermal control elements 196 can then be set to thermally cycle all of the partitions between 95° C. and 60° C. In an exemplary embodiment, thermal control elements 1-3 of the thermal control elements 196 will be held at room temperature, or a specified temperature between 15-25° C., or will be thermally cycled between 95° C. and 60° C. in the same way as the other thermal control elements. After about 35-45 cycles as is typical of PCR, the number of positive and negative partitions can be counted as part of the digital PCR analysis. Poisson statistics as set forth by Eqns. 3-6 above can then be used to quantify (a) the diluted sample droplet concentration, and therefore (b) the original sample droplet concentration.

Following the completion of the digital PCR reaction protocol and analysis, the partition droplets 204 can be discarded or extracted for further reactions. In one exemplary embodiment, the EWOD cartridge 180 is disposable, and the entire cartridge may be discarded with the partition droplets and replaced by a replacement EWOD cartridge 180.

FIGS. 15A-15E are drawings depicting a progression of steps constituting a first portion of an exemplary method of performing a digital PCR reaction protocol in accordance with embodiments of the present invention, said first portion constituting a variation on determining the appropriate dilution factor. FIGS. 15A-15E are similarity to FIGS. 14B-14F of the previous embodiment, in that a progression of steps for calculating an appropriate dilution factor is described. Accordingly, like components in these figures are identified with like reference numerals. Principally, the embodiment of FIGS. 15A-15E differs in that there is an additional preparation step of diluting the first sample droplet used to calculate the dilution factor. For example, if there is a limited sample volume, or if the sample volume is particularly precious, or if it is suspected that the sample volume is highly concentrated, a dilution step may be performed prior to initial determination of the Ct value to reduce the amount of sample used for the dilution factor determination step.

Figure 15A:
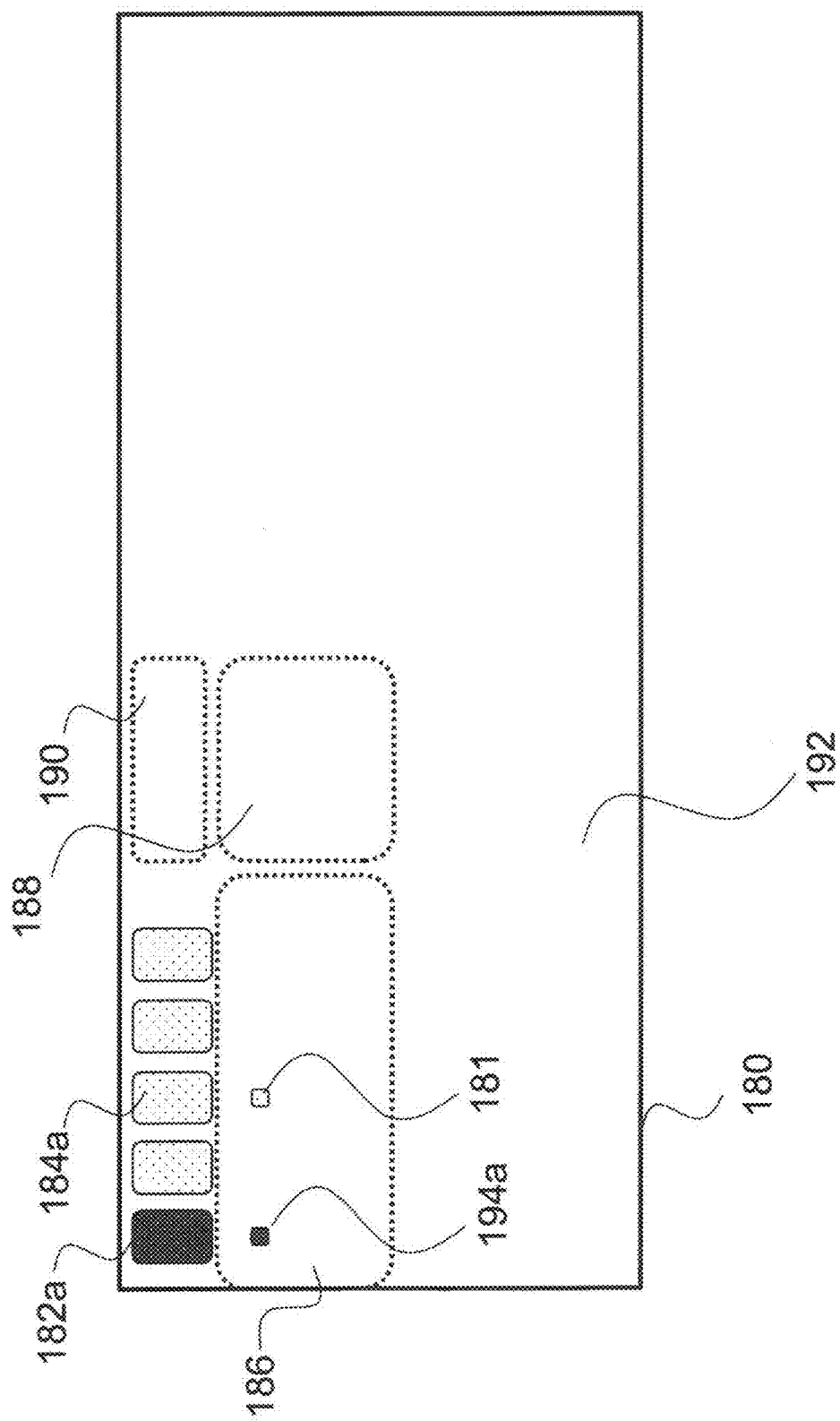
FIG. 15A, FIG. 15B, FIG. 15C, FIG. 15D, and FIG. 15E are drawings depicting a progression of steps constituting a first portion of an exemplary method of performing a digital PCR reaction protocol in accordance with embodiments of the present invention to determine an appropriate dilution factor.
Figure 15B:
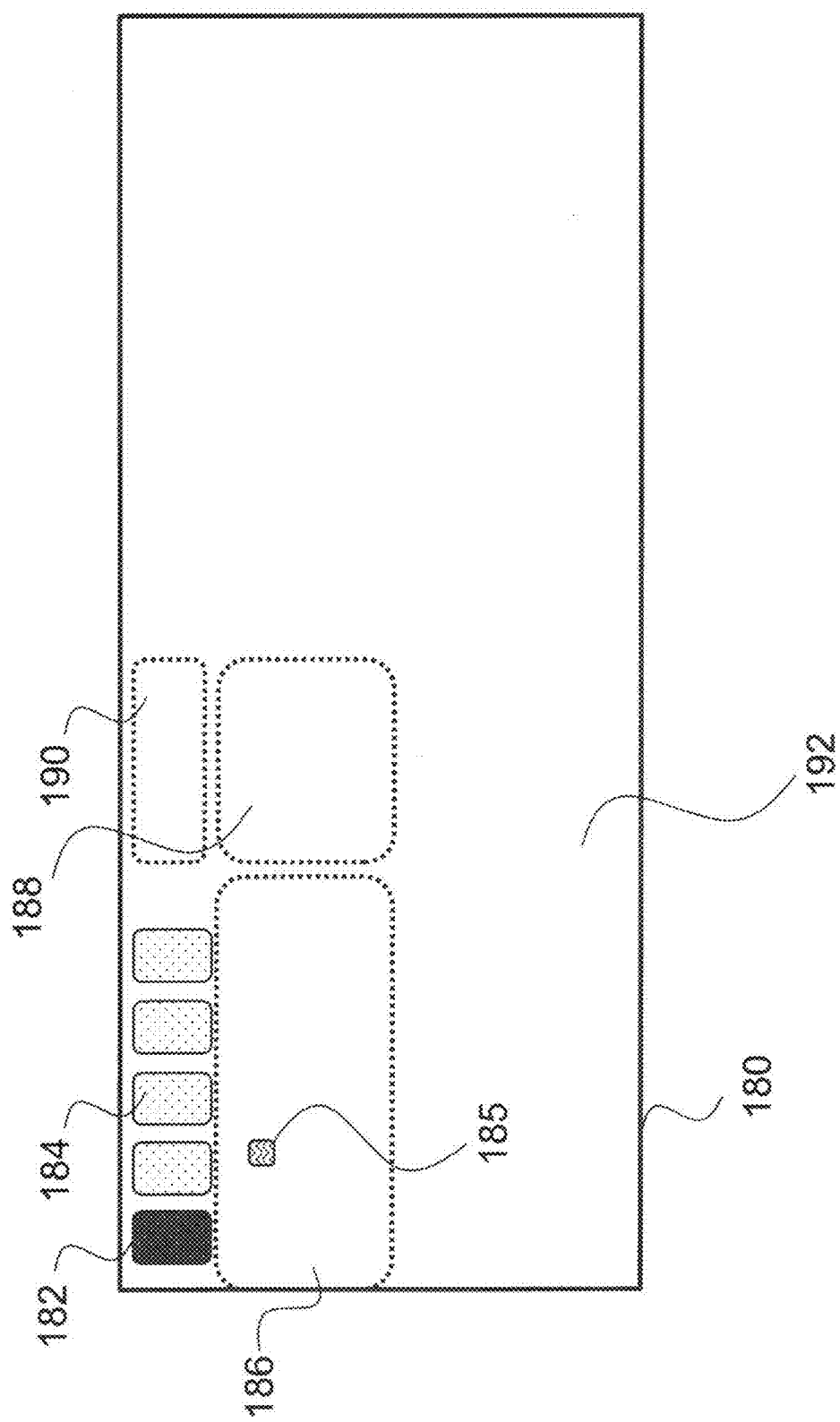
Figure 15C:
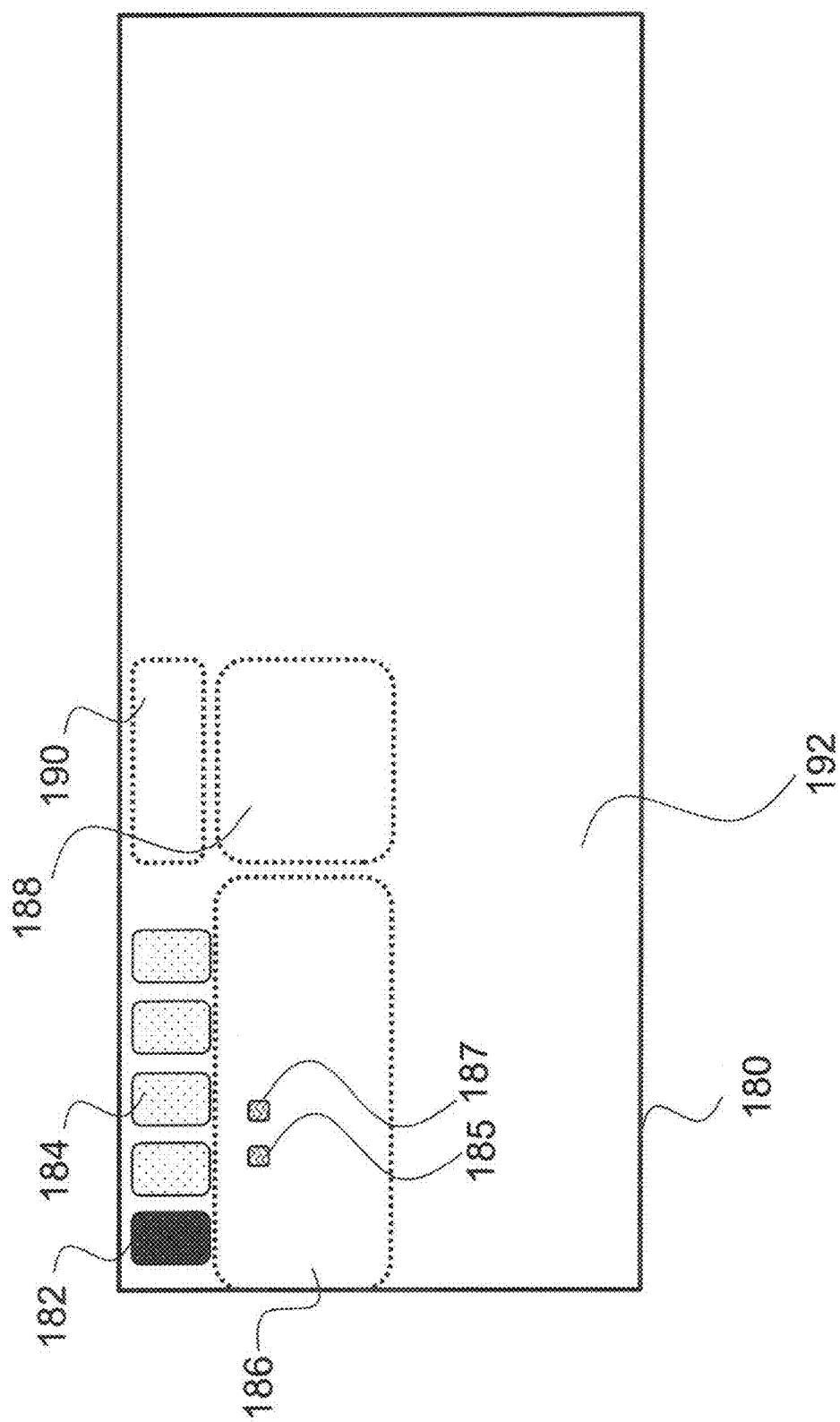

With the example of FIGS. 15A-15E, FIG. 15A is a drawing depicting the EWOD cartridge 180 including the EWOD array into which there has been inputted a sample volume 182a and four diluent volumes 184a, similarly as in the previous embodiment. Again, the example sample volume 182a includes the DNA having a target portion to undergo the amplification process, primers, probe(s) and mastermix. The diluent volumes 184a may be used to dilute the sample volume 182a, and includes primers, probe(s) and mastermix at the same concentration as in the sample volume 182a but lacking the DNA. In a first step of the reaction protocol as shown in FIG. 15A, the electrowetting operation of the EWOD cartridge 180 is used to extract a first sample droplet 194a from the sample volume 182a into the sample preparation zone 186. In this particular example, a diluent droplet 181 also is dispensed into the sample preparation zone 186 using electrowetting forces. As shown in FIG. 15B, the droplets 194a and 181 are then mixed and merged into an initial diluted sample droplet 185 using electrowetting forces to perform droplet manipulation operations comparably as referenced above with respect to FIG. 14G. As shown in FIG. 15C, once the sample droplet 182a and the diluent droplet 181 are mixed thoroughly and merged into the initial diluted sample droplet 185, the initial diluted sample droplet may be split into a number of smaller diluted daughter droplets 187, or a single daughter droplet 187 may be dispensed from the initial diluted sample droplet 185.

Figure 15D:
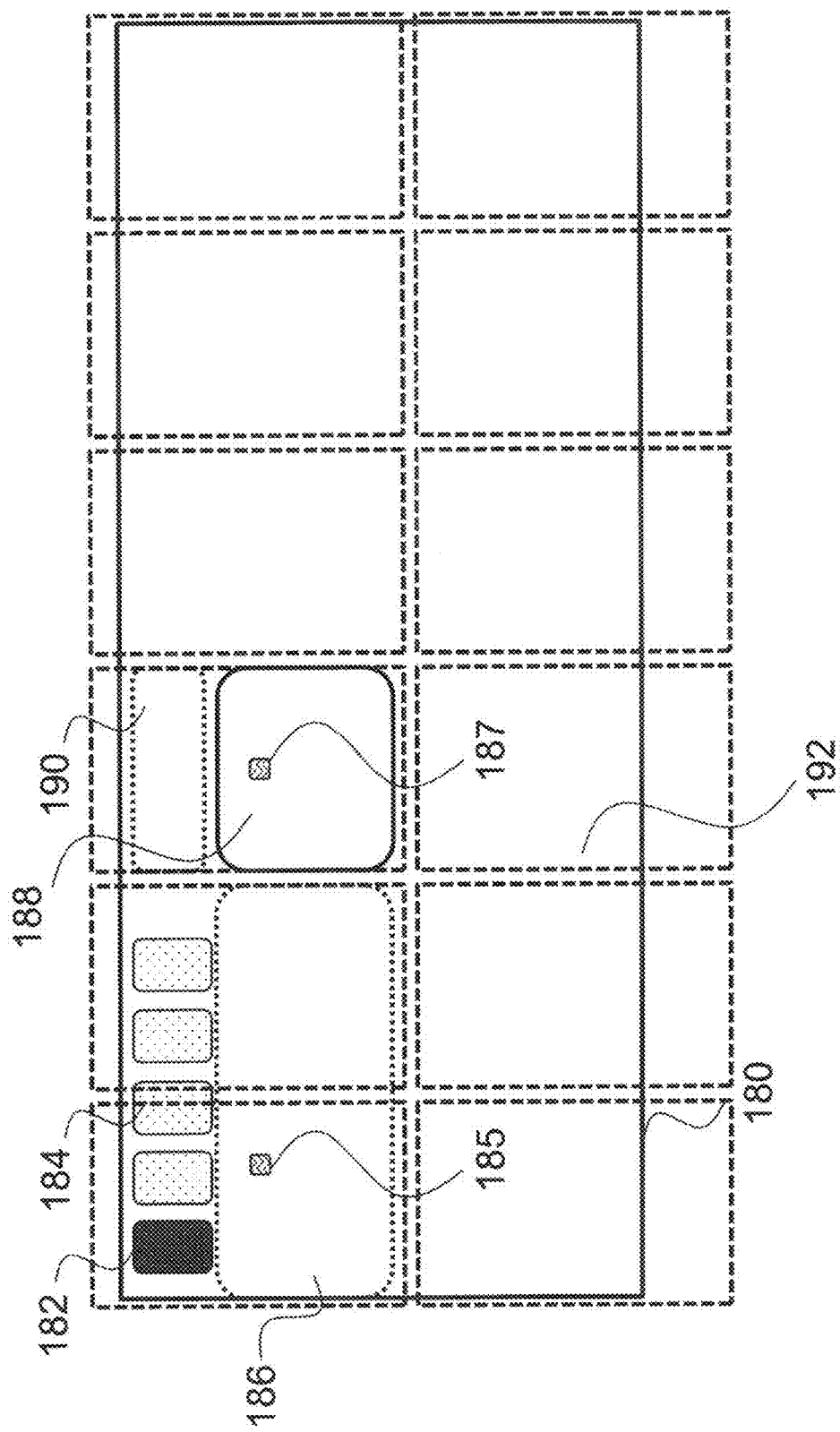

FIG. 15D is a drawing depicting the exemplary EWOD cartridge 180 with the EWOD array overlaid onto a plurality of thermal control elements 196 (similarly as FIG. 14D). This example again employs the 12-element configuration described above with respect to FIG. 13C. As further shown in FIG. 15D, a single, or optionally multiple, daughter droplets 187 is moved into the first nucleic acid amplification zone 188 via electrowetting forces, where thermal control element 196-3 is used to thermally cycle the droplet between 95° C. and 60° C. to perform a PCR amplification process comparably as in the previous embodiment. Each time the droplet is cooled to 60° C., a fluorescence image is taken and the thermal cycling process continues until the fluorescence value is greater than a pre-defined threshold, which permits determination of the threshold cycle Ct. The number of cycles may vary and need not require the full 35-45 cycles common in PCR, and the thermal cycling can stop as soon as the Ct value can be calculated. The remaining thermal zones, i.e., the zones corresponding to the thermal control elements other than 196-3, may be kept at the optimal temperature for any reagents within a given thermal zone, or can remain at room temperature.

Figure 15E:
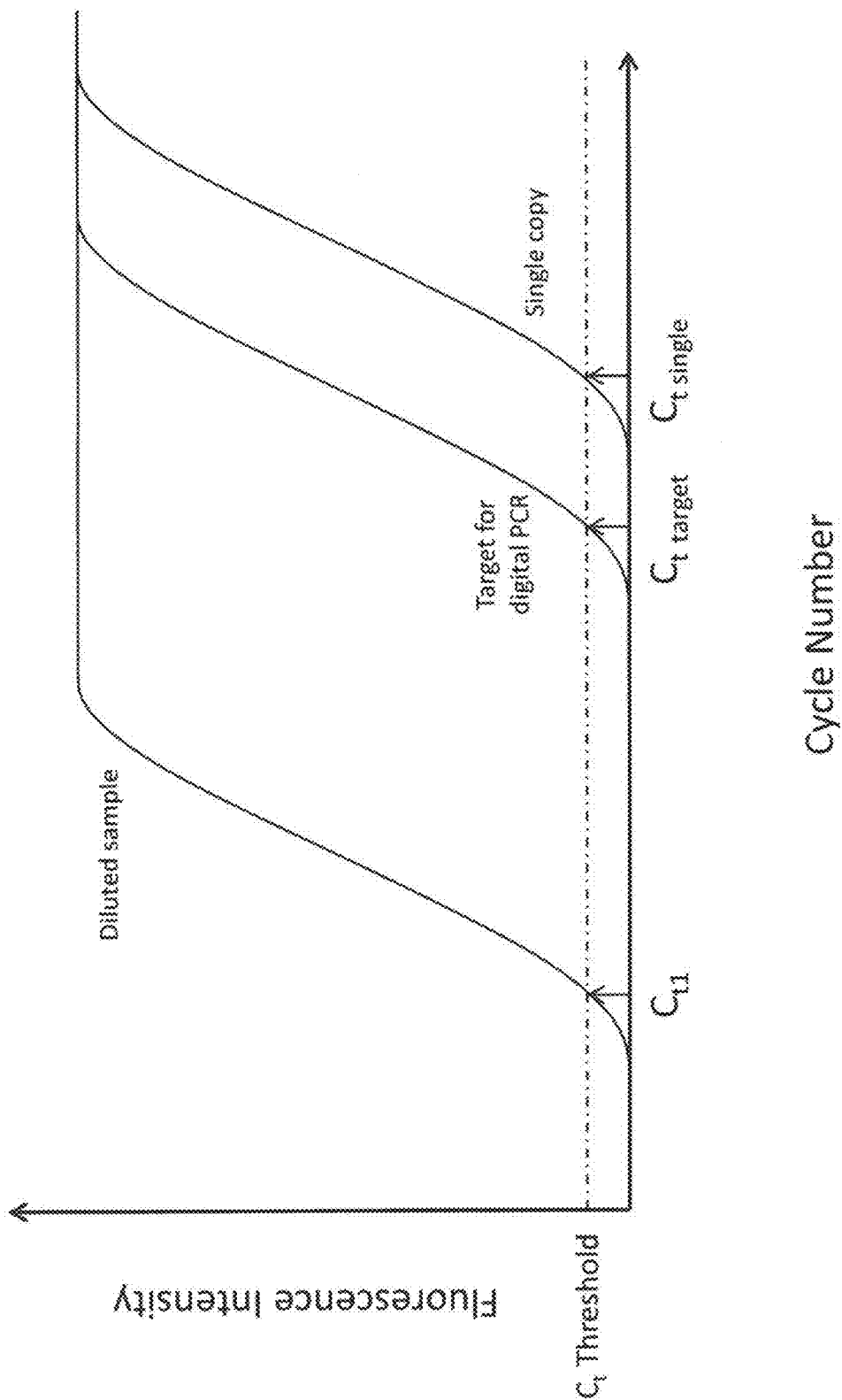

FIG. 15E is a graph depicting an example of a fluorescence intensity curve that illustrates representative calculations associated with this example for the initial diluted sample droplet 187 to determine the threshold cycle Ct1 for such droplet. As referenced above, the target cycle number $Ct_{target}$, and/or equivalent concentration, to enable subsequent digital PCR quantification, and the turn-on value, $Ct_{single}$, for the threshold fluorescence for a single copy can be known values generated from prior experimentation. The fluorescence intensity curve for the initial diluted sample droplet also is plotted here for clarity. Once the Ct1 value has been determined through the fluorescence intensity curve for the diluted sample daughter droplet, the concentration of the sample can be estimated by inputting the Ct1 value into a reference standard curve equation for the reaction saved on the system's computer. The dilution factor can then be calculated by comparing the diluted sample concentration to the target concentration, required for subsequent digital PCR analysis, using Eqn. 7 above. Accordingly, referring to FIG. 15E, the system then uses the saved reference equation for the reaction and the measured Ct1 value to calculate the concentration of (a) the diluted sample and therefore (b) the original sample (given that the original sample dilution factor is already known). The Ct for the original sample can then be used with the $Ct_{target}$, the target concentration for supporting subsequent digital PCR quantification, in Eqn. 7 to calculate the optimal dilution factor for the sample. The dilution factor aims to dilute the sample to an optimal concentration equivalent to, typically, ~0.7-1.6 copies/partition.

The system then may perform digital PCR based on the calculated dilution factor comparably as described with respect to FIGS. 14G-14I above. The system automatically dilutes the original sample by the calculated dilution factor for digital PCR quantification, and partitions the diluted sample into the correct number of partitions. The partitions are moved into the digital PCR zone 192. In an exemplary embodiment, all of the diluted sample will be split into partitions for quantification. Thermal control elements 4-12 can then be set to thermally cycle all of the partitions between 95° C. and 60° C. After typically 35-45 cycles, the number of positive and negative partitions can be counted, and Poisson statistics (Eqns. 3-6) can then be used to quantify (a) the diluted sample and therefore (b) the original sample concentration.

In another exemplary embodiment, the determination of the dilution factor may be performed by a combination of the FIG. 14 series steps and FIG. 15 series steps, which essentially provides for a double checking of the calculated dilution factor. Generally, this embodiment includes an additional PCR step after an initial calculation of the dilution factor to confirm that the diluted sample is in the correct concentration range for digital PCR quantification before proceeding with the full digital PCR quantification.

Figure 16A:
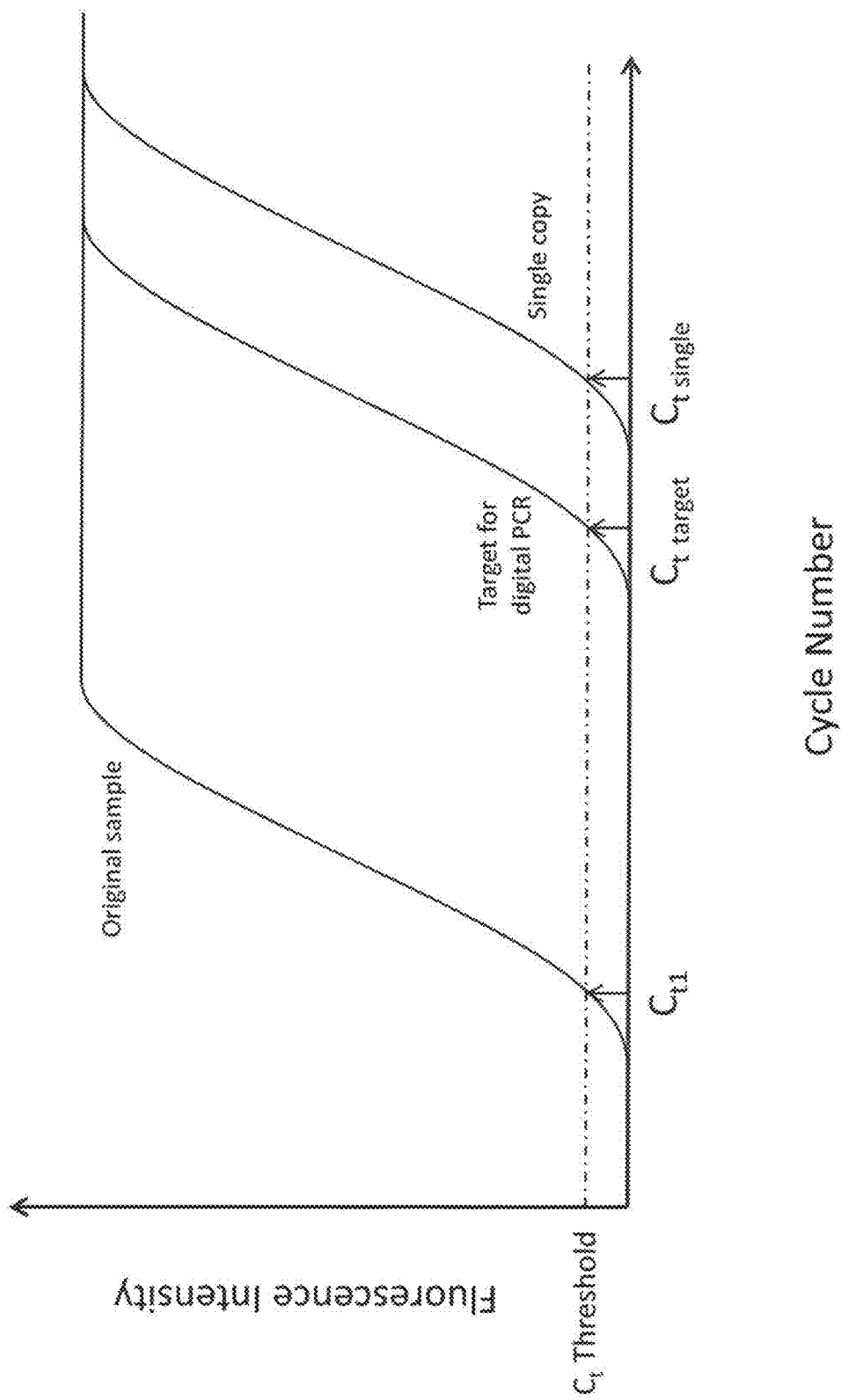
FIG. 16A is a graph depicting an example of a fluorescence intensity curve that may be employed to determine a Ct threshold, Ct1, corresponding to the original sample.
Figure 16B:
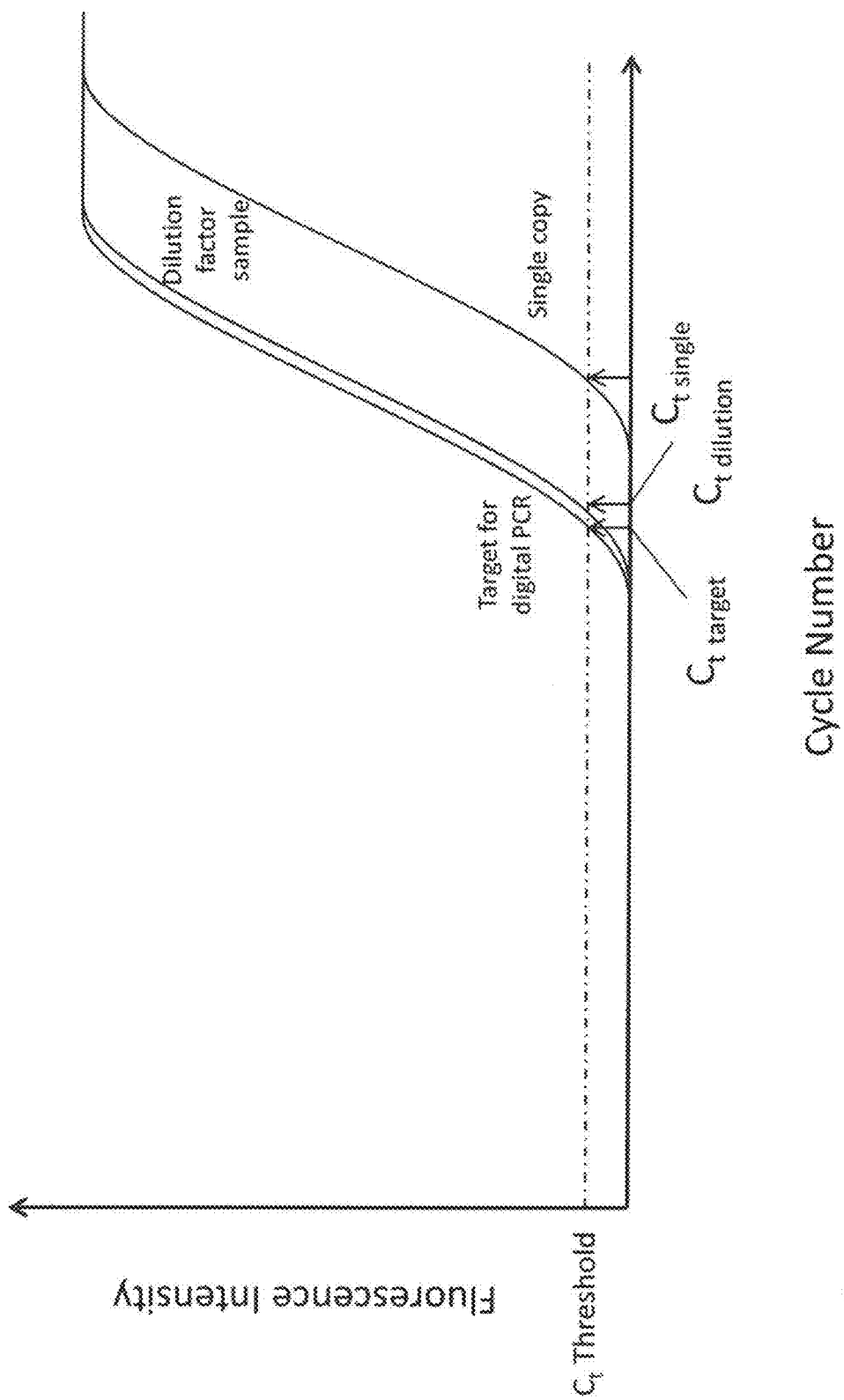
FIG. 16B is a graph depicting an example of a fluorescence intensity curve that may be employed to determine a Ct threshold, the $Ct_{dilution}$, for a diluted sample from the original sample of FIG. 16A.

First, the processes described above with respect to FIGS. 14B-14E are performed to calculate a first dilution factor. FIG. 16A is a graph depicting an example of a fluorescence intensity curve that may be employed to determine a first Ct threshold, Ct1, corresponding to the original sample similarly as shown in FIG. 14E. Next, the processes of FIGS. 15A-15D are performed, to determine another $C_t$ threshold, $Ct_{-dilution}$, for a diluted sample droplet. FIG. 16B is a graph depicting an example of a fluorescence intensity curve that may be employed to determine the $Ct_{-dilution}$.

Once the $Ct_{-dilution}$ value has been determined through the fluorescence intensity curve of FIG. 16B, $Ct_{-dilution}$ can be compared to the Ct for the target concentration, $Ct_{-target1}$, that will support subsequent digital PCR quantification. If the $Ct_{-dilution}$ and $Ct_{-target}$ values are suitably close together, for example within 1-3 cycles, then the system will automatically proceed with sample partitioning and digital PCR thermal cycling as described and depicted with respect to FIGS. 14G-14I above (and further as set forth above when the sample is initially diluted as described with respect to the FIG. 15 series figures). If, in contrast, the $Ct_{-dilution}$ and $Ct_{-target}$ values are further than three cycles apart, and the indication is that the diluted sample is more concentrated than the optimal concentration for digital PCR quantification, then another dilution step can be integrated. If the $Ct_{-dilution}$ indicates that the diluted sample is less concentrated than the optimal concentration for digital PCR quantification, then the partitioning can still proceed as digital PCR can quantify down to single copy numbers.

In the instance that the initial diluted sample droplet actually contains no template DNA, e.g. is a negative partition, then the above processes can be repeated until such time as a positive partition is extracted from the diluted sample. Additionally and/or alternatively, the system can be programmed to dispense an array of daughter droplets from the initial diluted sample and process them all simultaneously in the first amplification zone 188, and the Ct values of the positive partitions are analyzed as described above. In certain exemplary embodiments, between 1 and 100 daughter droplets may be analyzed, or 1-50 daughter droplets or 1-20 daughter droplets may be analyzed to utilize less of the original sample.

FIGS. 17A-17J are drawings depicting a progression of steps constituting another exemplary method of performing a digital PCR reaction protocol in accordance with embodiments of the present invention, including a determination of efficiency of reaction. In such embodiment, the efficiency of the PCR reaction is calculated prior to estimating the concentration of the initial sample volume, particularly if the reaction is generally known to be inefficient. The initial sample may be a DNA sample, or complementary DNA reverse-transcribed from an RNA sample. Generally, for measuring efficiency a preferred embodiment includes a 10-fold dilution and checking the efficiency of the reaction against a reference equation for the reaction and determine if there are any inconsistencies. A range of dilution factors can be calculated taking in account efficiency and a target number of copies per partition, and the dilution factor mid-way between the extremes is a sensible starting point.

Figure 17A:
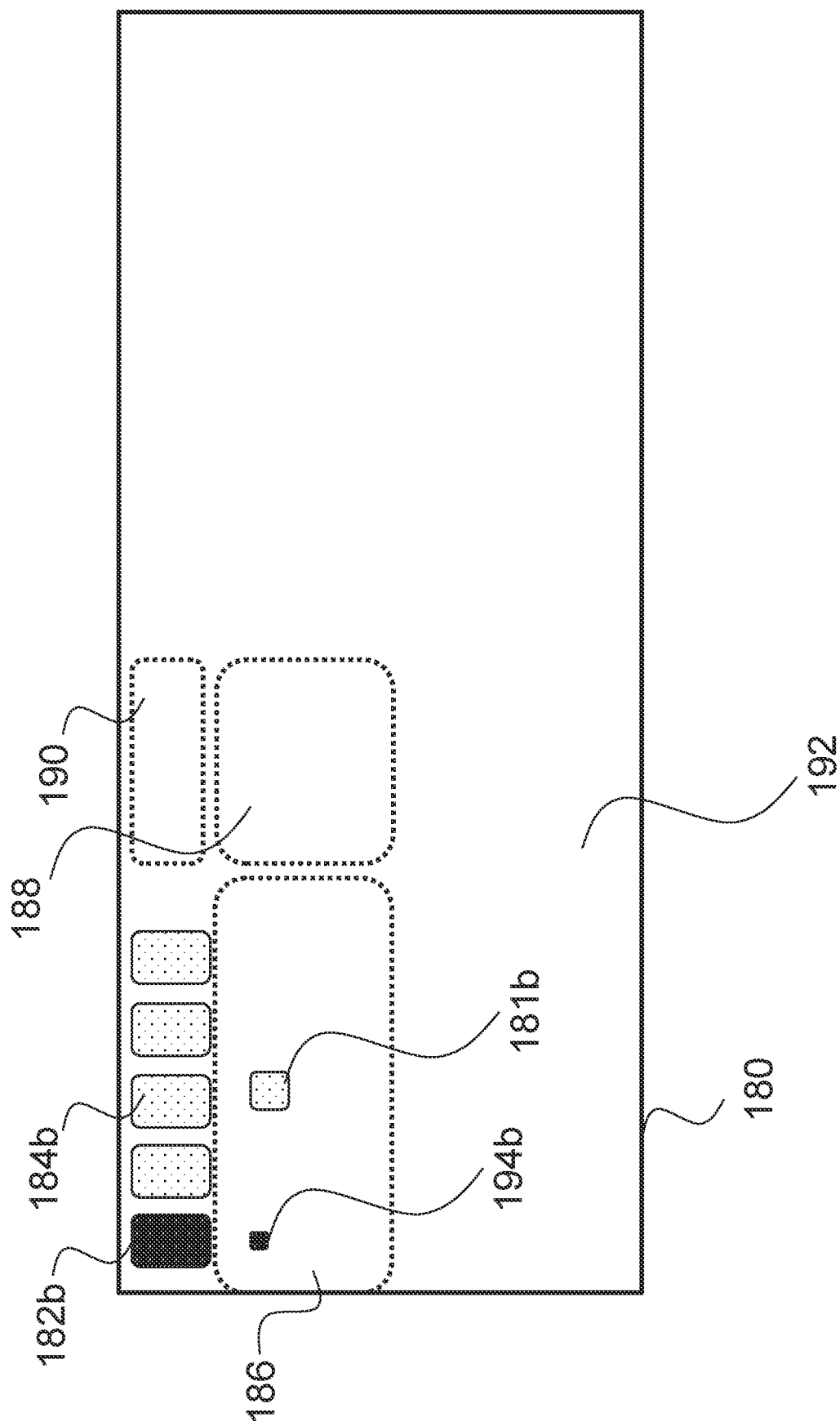
Figure 17C:
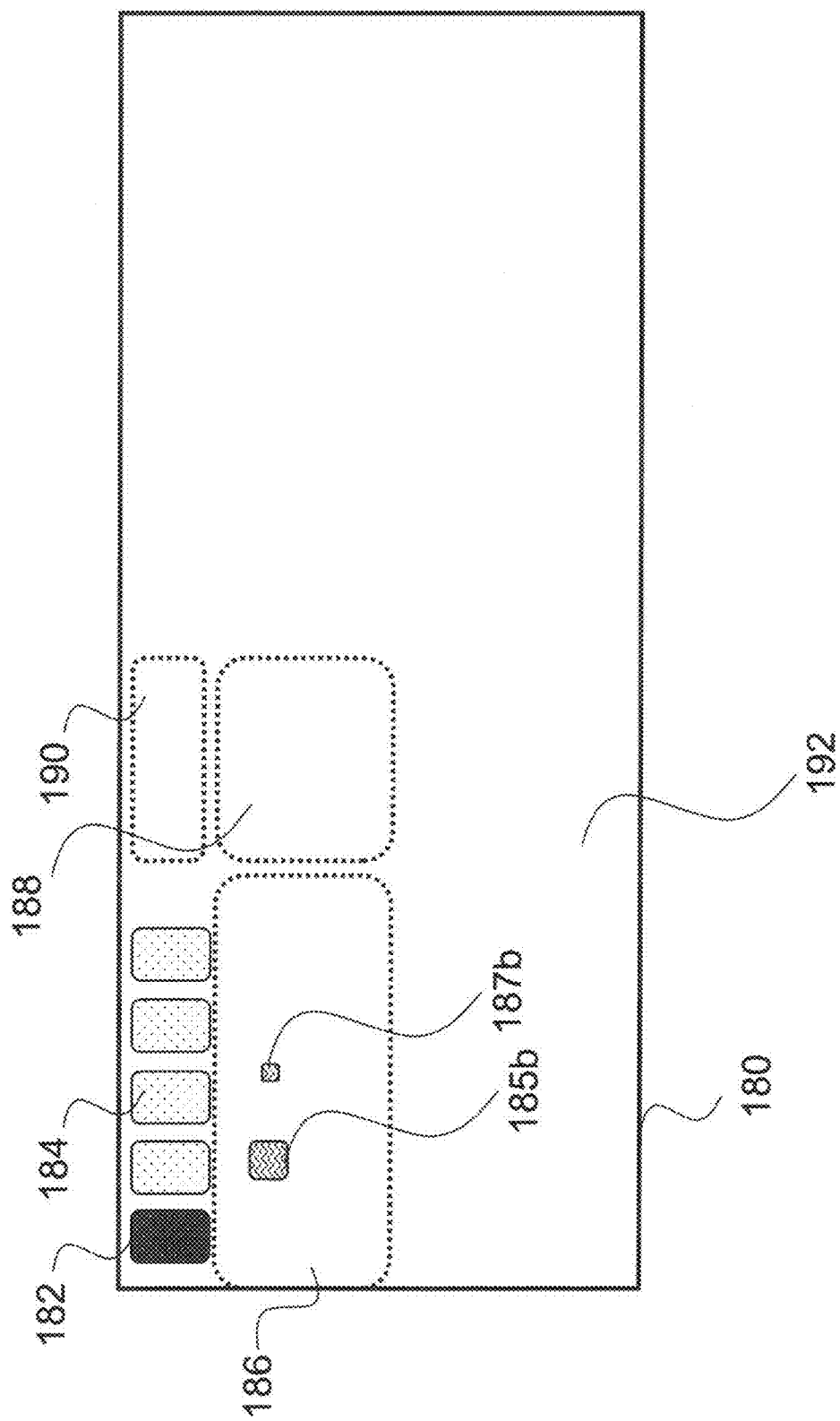

With the example of FIGS. 17A-17J, FIG. 17A is a drawing depicting the EWOD cartridge 180 including the EWOD array into which there has been inputted a sample volume 182b and four diluent volumes 184b, similarly as in the previous embodiments. In a first step of the reaction protocol as shown in FIG. 17A, the electrowetting operation of the EWOD cartridge 180 is used to extract a first sample droplet 194b from the sample volume 182b into the sample preparation zone 186. In this particular example, a diluent droplet 181b also is dispensed into the sample preparation zone 186 using electrowetting forces. As shown in FIG. 17B, the droplets are then mixed and merged into an initial diluted sample droplet 185b using electrowetting forces to perform droplet manipulation operations comparably as referenced above with respect to FIG. 14G. Preferably in this example, the diluted sample droplet 185b will be a 1 in 10, a 1 in 100, or a 1 in 1000 dilution. As shown in FIG. 17C, once the sample droplet 182a and the diluent droplet 181b are mixed thoroughly and merged into the initial diluted sample droplet 185b, the initial diluted sample droplet may be split into one or more diluted sample daughter droplets 187b, or a single daughter droplet 187b is dispensed from the diluted sample droplet 185b.

Figure 17D:
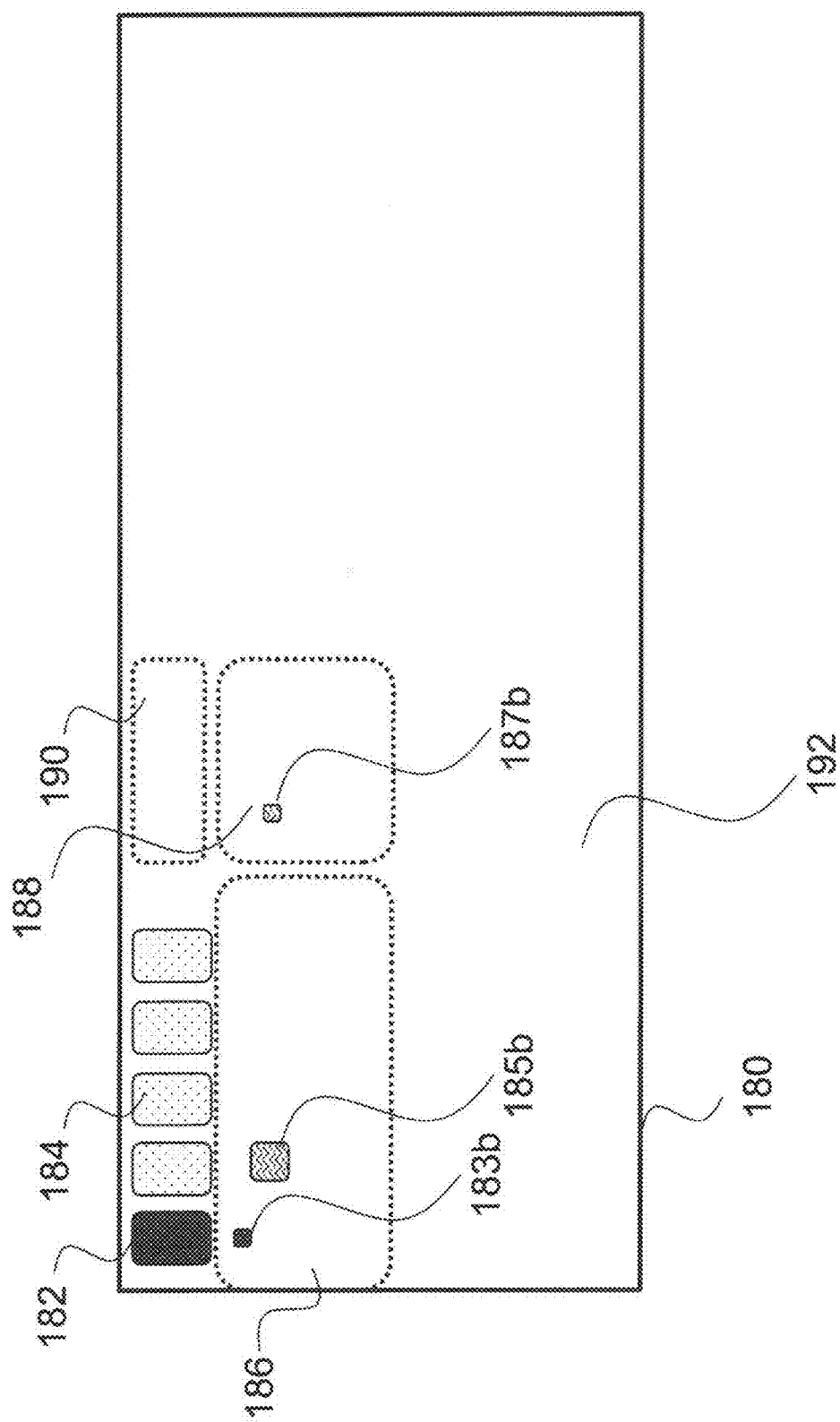
Figure 17E:
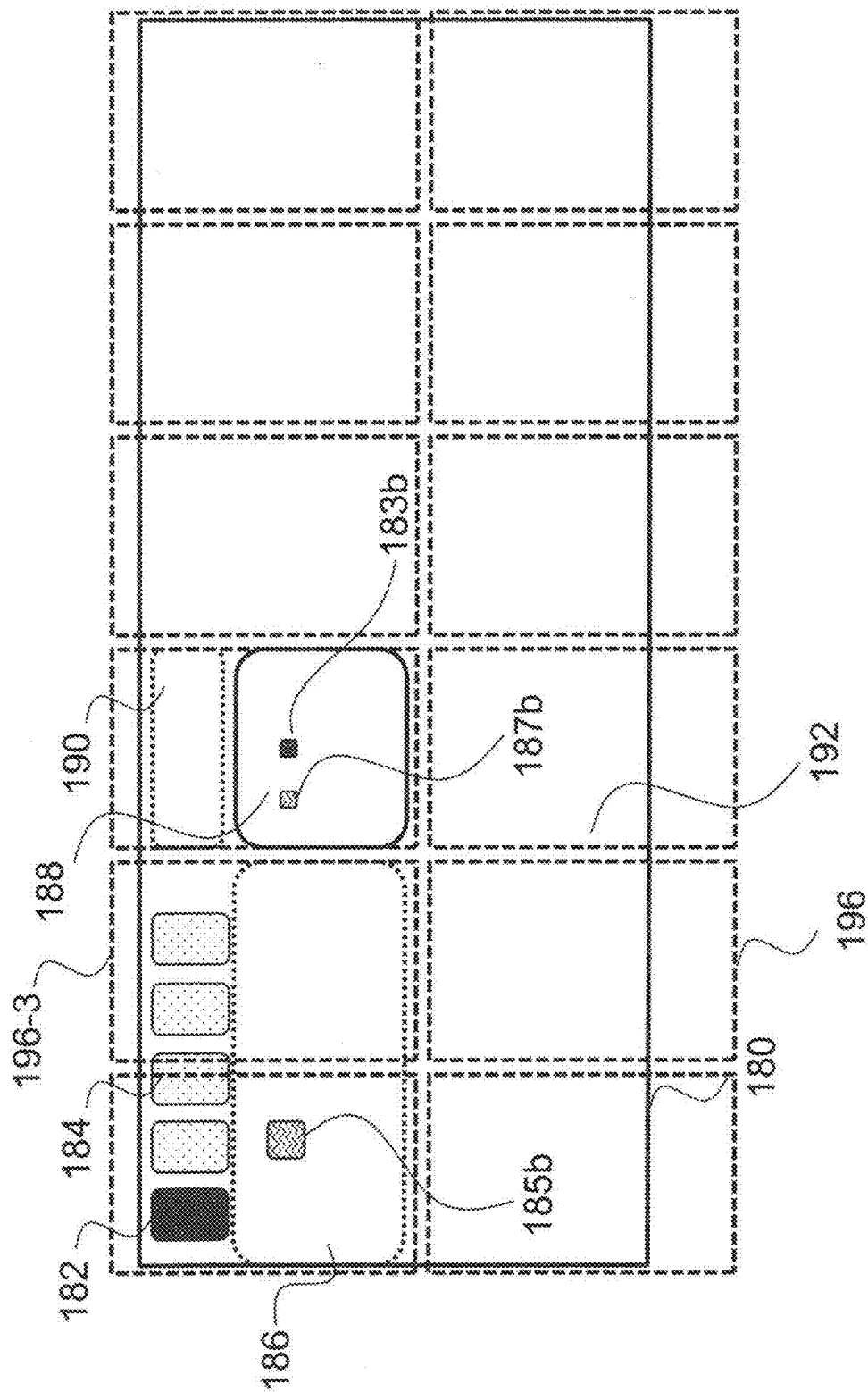

As shown in FIG. 17D, a single, or optionally multiple, daughter droplet 187b is moved into the first nucleic acid amplification zone 188 via electrowetting forces, and a second sample droplet 183b is dispensed into the PCR sample preparation zone 186. FIG. 17E is a drawing depicting the exemplary EWOD cartridge 180 with the EWOD array overlaid onto the plurality of thermal control elements 196. This example again employs the 12-element configuration described above with respect to FIG. 13C. The second sample droplet 183b is then moved into the first nucleic acid amplification zone 188 where thermal control element 196-3 is used to thermally cycle the sample droplet and the diluted daughter droplet between 95° C. and 60° C. to perform a PCR amplification process comparably as in previous embodiments.

Figure 17F:
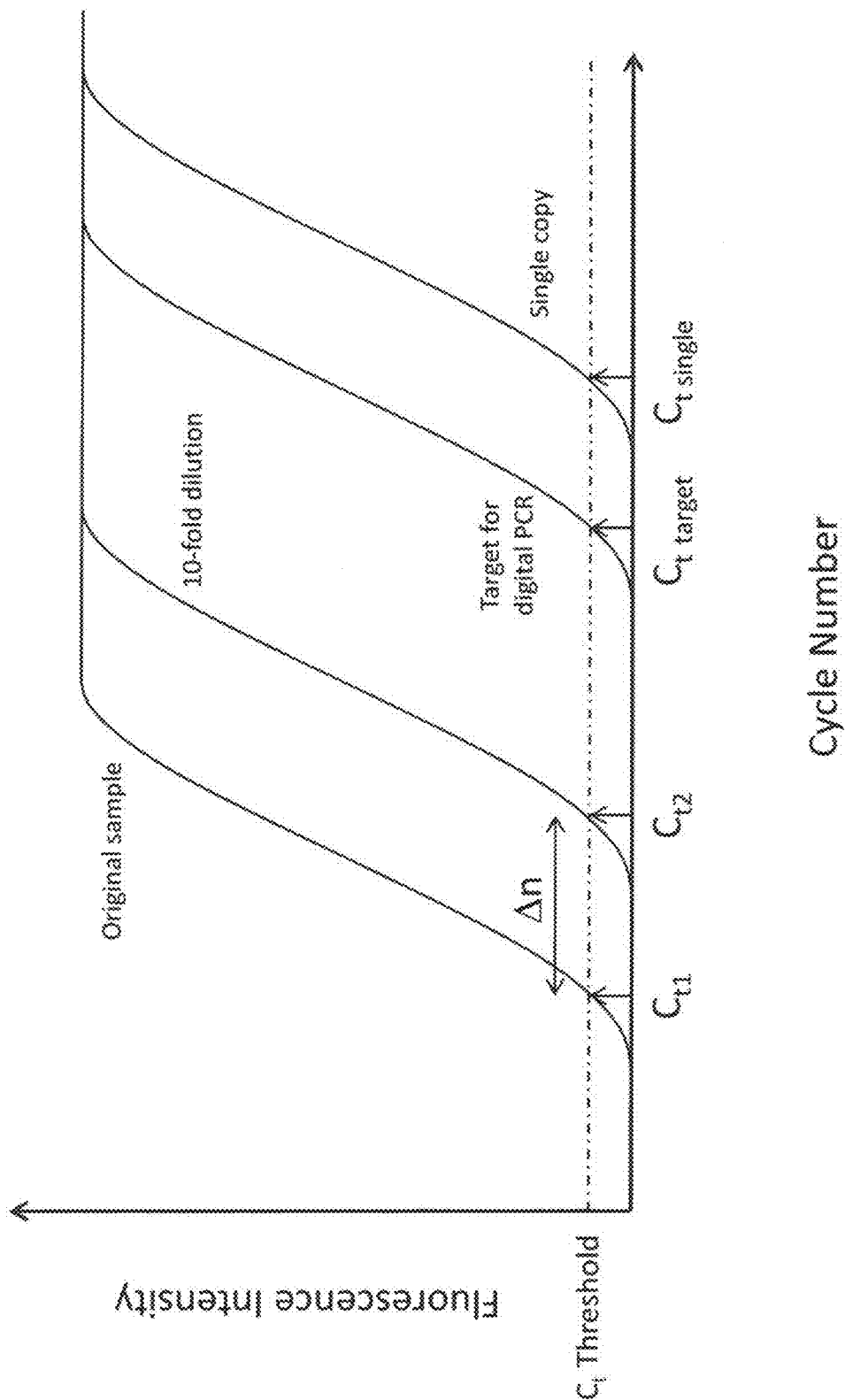
Figure 17G:
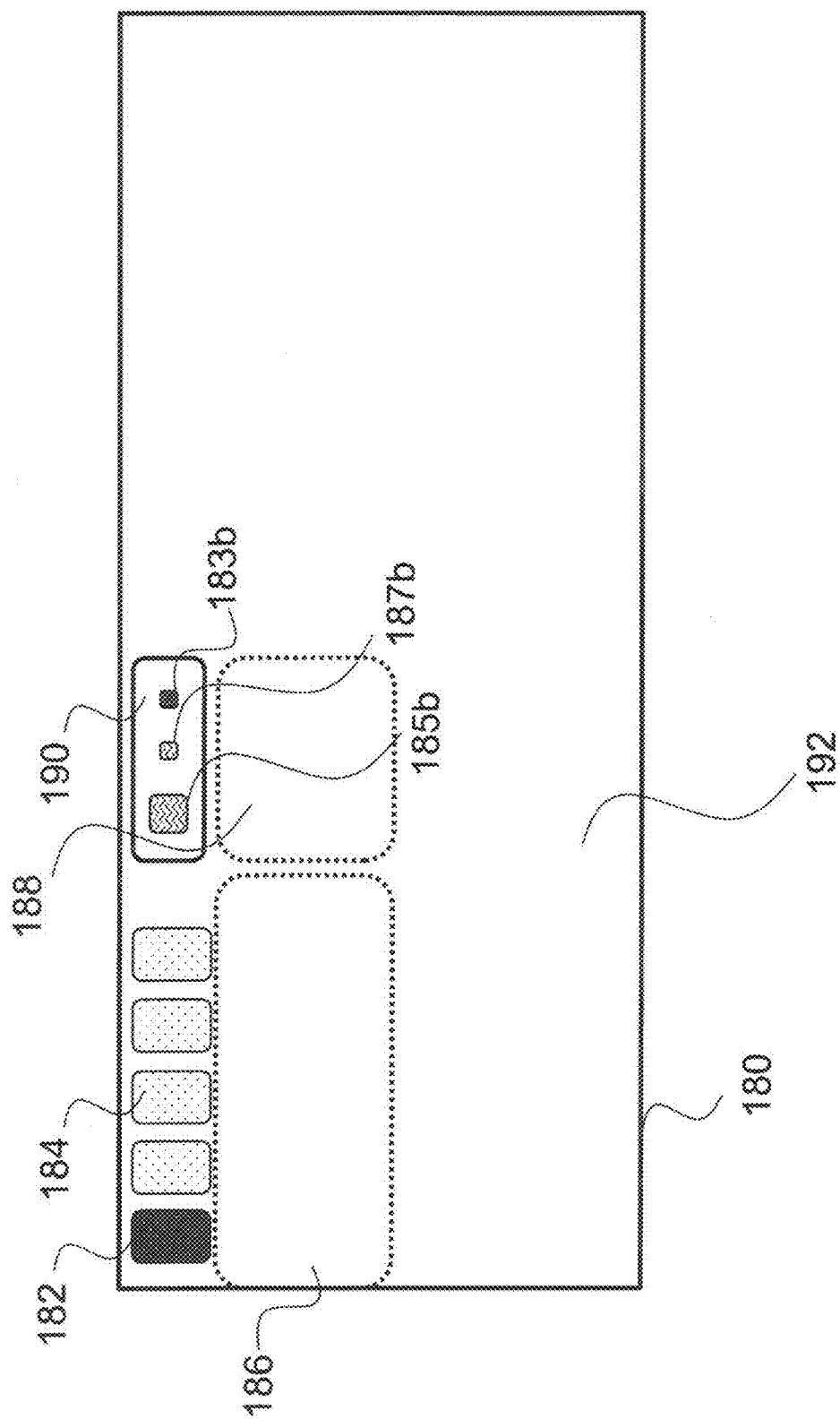

In this embodiment, an optical measurement is taken each time the first amplification zone 188 is at 60° C., and the fluorescence intensity against cycle number is plotted for both the second sample droplet 183b and the daughter droplet 187b, such plots being depicted in the graph of FIG. 17F. As seen in such graph, Ct is measured for each droplet, with Ct1 corresponding to the sample droplet 187b and Ct2 corresponding to the diluted daughter droplet 187b. Once the Ct1 and Ct2 values are determined, thermal cycling is halted and the efficiency of the reaction calculated using Eqn. 1. The system then uses a saved reference equation for the reaction and the measured Ct1 and Ct2 values to estimate the concentration of (a) the diluted sample and (b) therefore the original sample. The Ct1 for the original sample can then be used with the Ct of the optimal concentration for digital PCR quantification, and the calculated efficiency of the reaction in Eqn. 7, to calculate the optimal dilution factor for sample quantification. The second sample droplet 183*b*, the diluted sample droplet 185*b*, and the daughter droplet 187*b*, may then be moved by electrowetting forces to the waste zone 190, as shown in FIG. 17G.

Figure 17H:
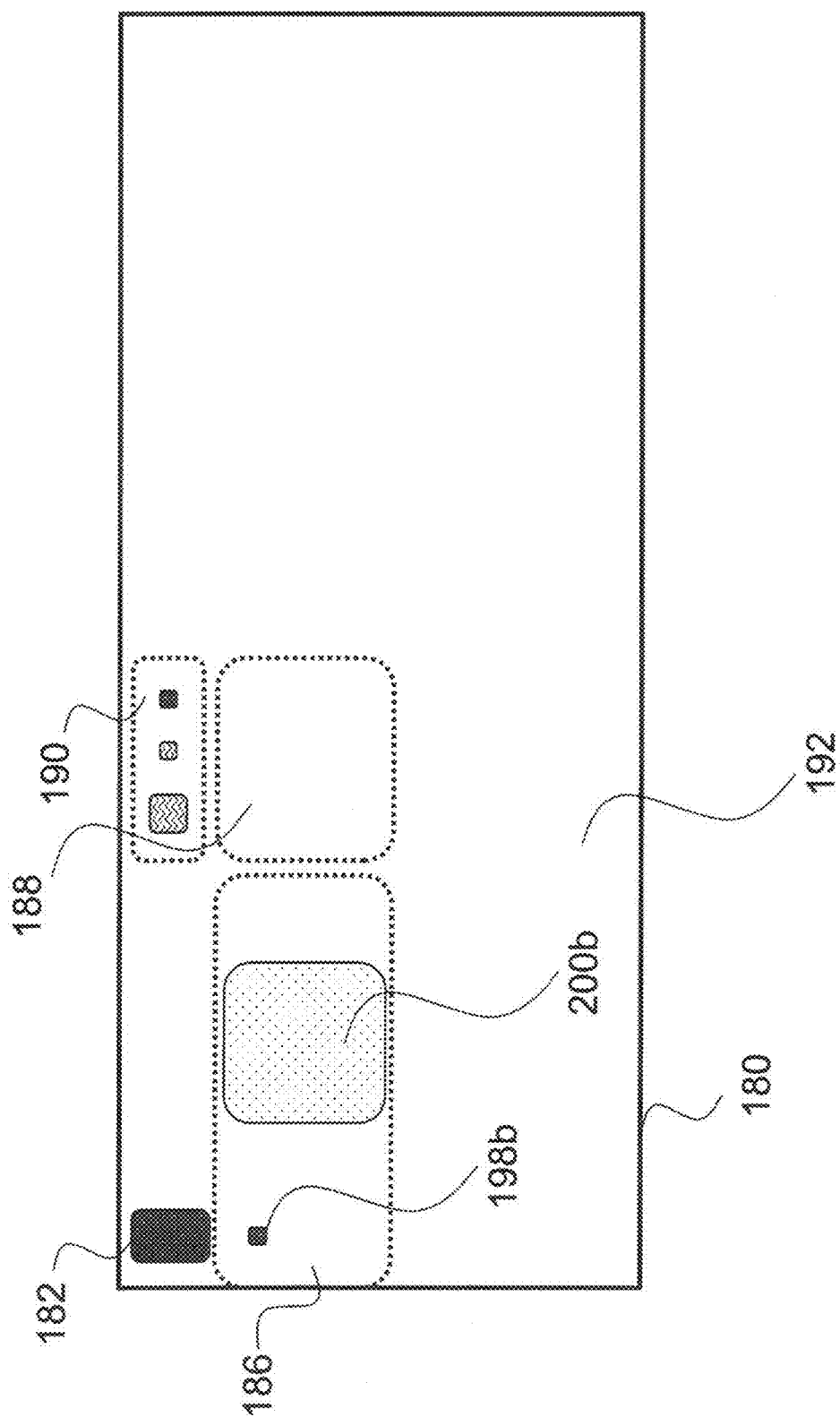
Figure 17I:
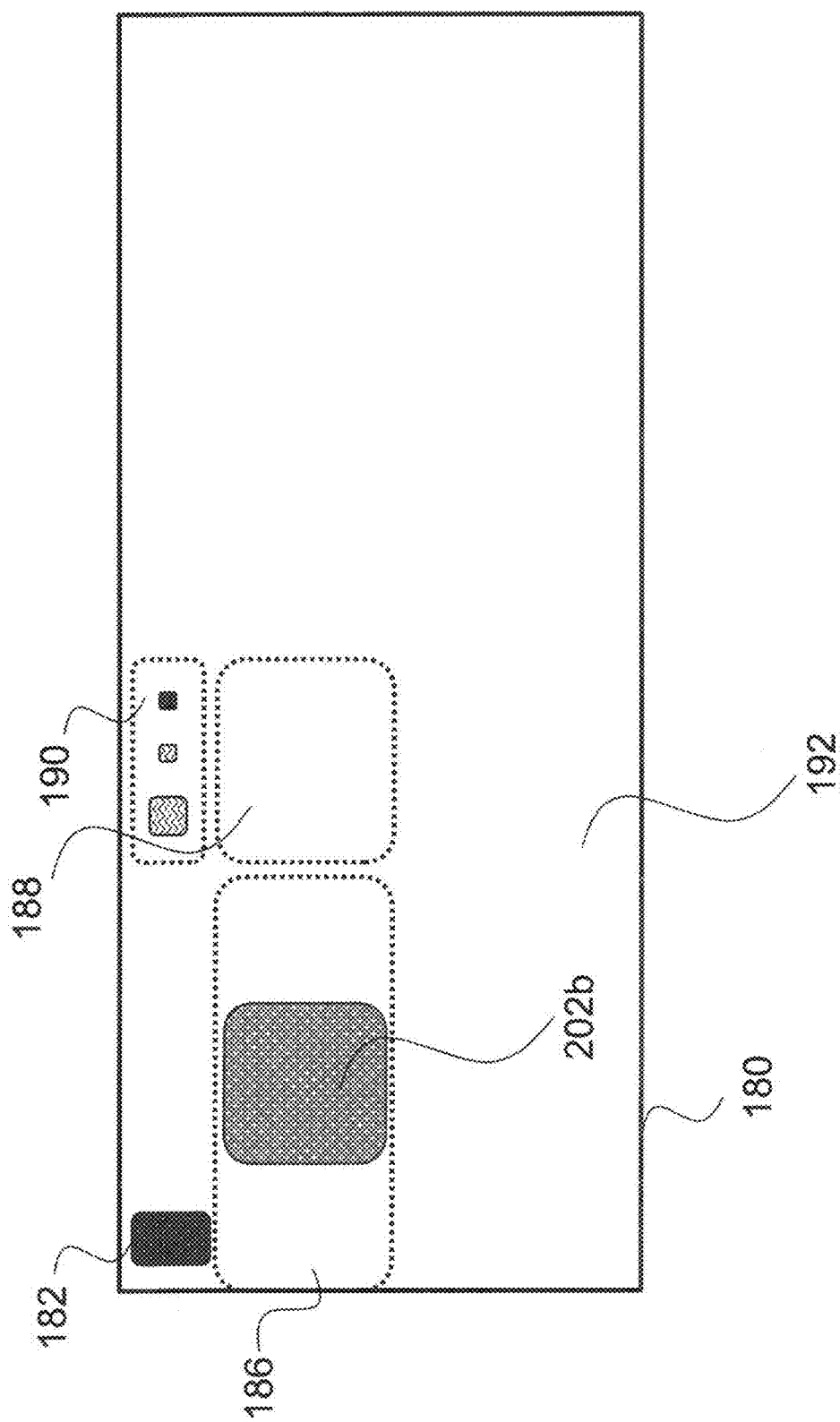

The system then may perform digital amplification, such as digital PCR, based on the calculated dilution factor comparably as described with respect to the previous embodiments. FIG. 17H is a drawing depicting a sample preparation step of digital PCR using the EWOD cartridge 180. In particular, the electrowetting operation of the EWOD cartridge 180 is used to extract another sample droplet 198*b* from the sample volume 182*b* into the sample preparation zone 186, alongside a diluent droplet 200*b* generated from one or more of the diluent volumes 184*b*. The diluent droplet 200*b* is generated to be of a volume sufficient for diluting the second sample droplet 198*b* by the dilution factor calculated using Eqn. 7 as referenced above. As illustrated in FIG. 17I, electrowetting forces are used to the mix and merge the second sample droplet 198*b* and diluent droplet 200*b* into a diluted sample droplet 202*b* within the sample preparation zone 186.

Figure 17J:
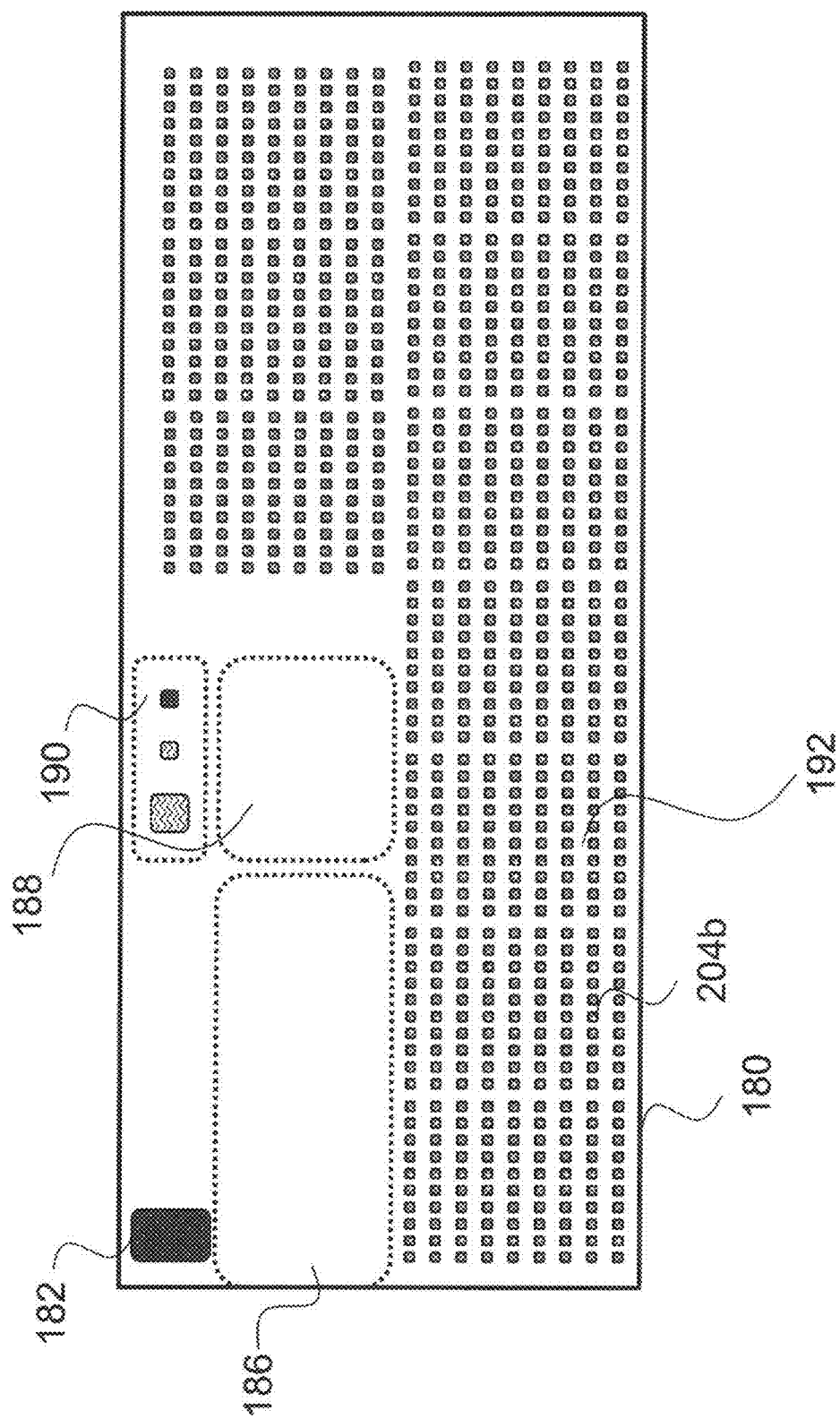

As illustrated in FIG. 17J, once the diluted sample droplet 202*b* has been fully mixed, the diluted sample 202*b* can be split via electrowetting forces into a plurality of partitions 204*b* capable of quantifying the diluted sample droplet 202*b* by digital PCR. The optimal bulk concentration for digital nucleic acid amplification is equivalent to ~0.7-1.6 copies per partition in the final digital assay. The target turn-on value aims to be within the optimal range. The sample is split into the partitions 204*b*, and the partitions are moved into the digital PCR zone 192. In a preferred embodiment, all of the diluted sample droplet 202*b* will be split into partitions 204*b* for quantification. Thermal control elements 4-12 of the thermal control elements 196 can then be set to thermally cycle all of the partitions between 95° C. and 60° C. for the requisite number of cycles. The number of positive and negative partitions can be counted as part of the digital PCR analysis, and Poisson statistics as set forth by Eqns. 3-6 above can then be used to quantify (a) the diluted sample droplet concentration, and therefore (b) the original sample droplet concentration.

In another embodiment, a normalization process is performed to account for fluorescence variations that are not related to performing PCR. Additional and/or alternative methods for normalization include normalizing to a passive reference dye so that non-PCR related fluorescence variations can be compensated. Passive dyes such as ROX are typically used and are present in the sample droplet. This is particularly useful for making the distinction between positive and negative partitions easier, thus reducing the probability of allocating false positive and/or false negative partitions. Normalization is performed using the following calculation.

$$\text{Relative Fluorescence} = \frac{\text{Sample Fluorescence}}{\text{Passive Dye Fluorescence}} \quad \text{(Eqn. 8)}$$

Figure 18A:
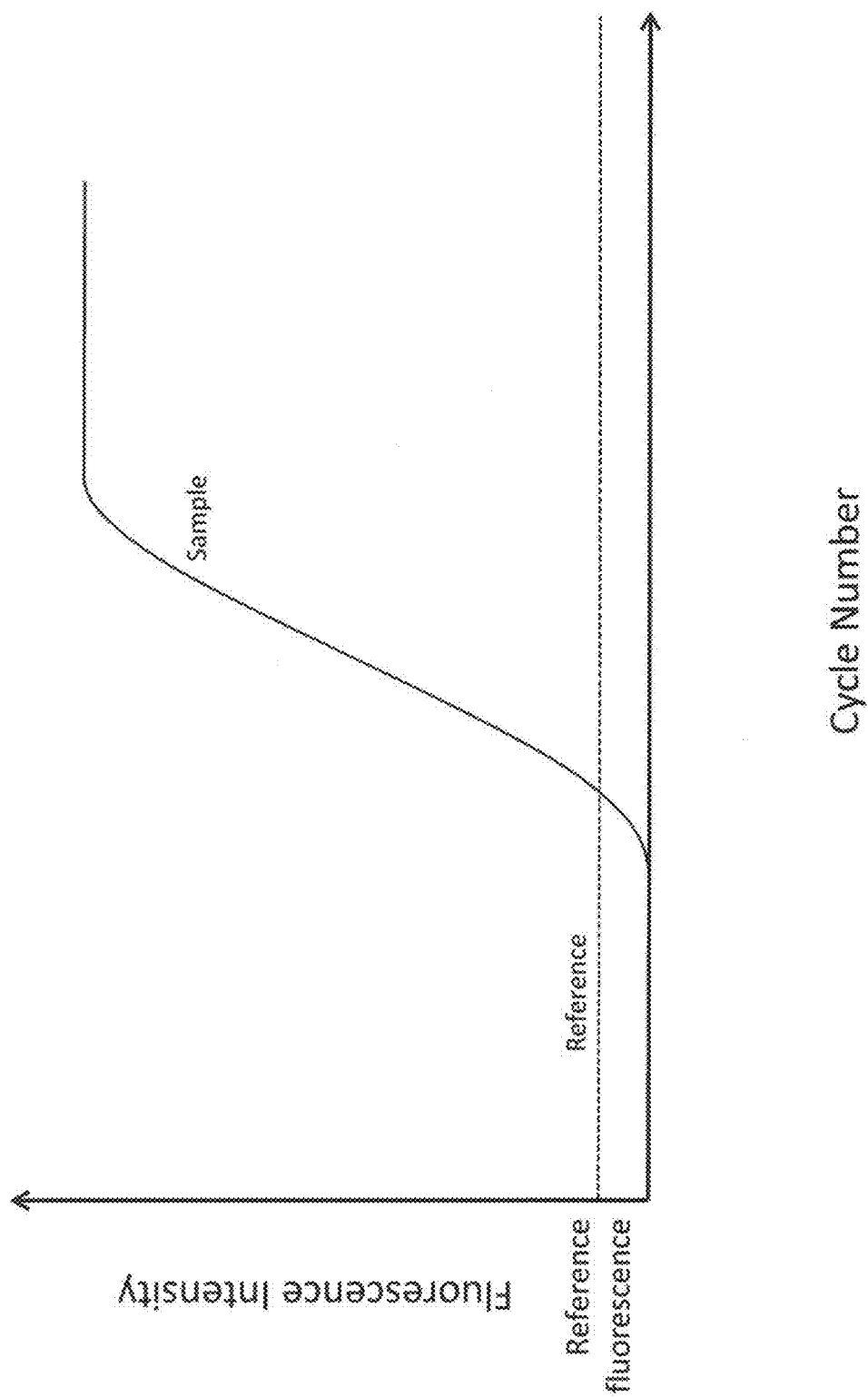
FIG. 18A is a graph illustrating a typical real time amplification curve for a partition containing both the sample material and a passive reference dye.
Figure 18B:
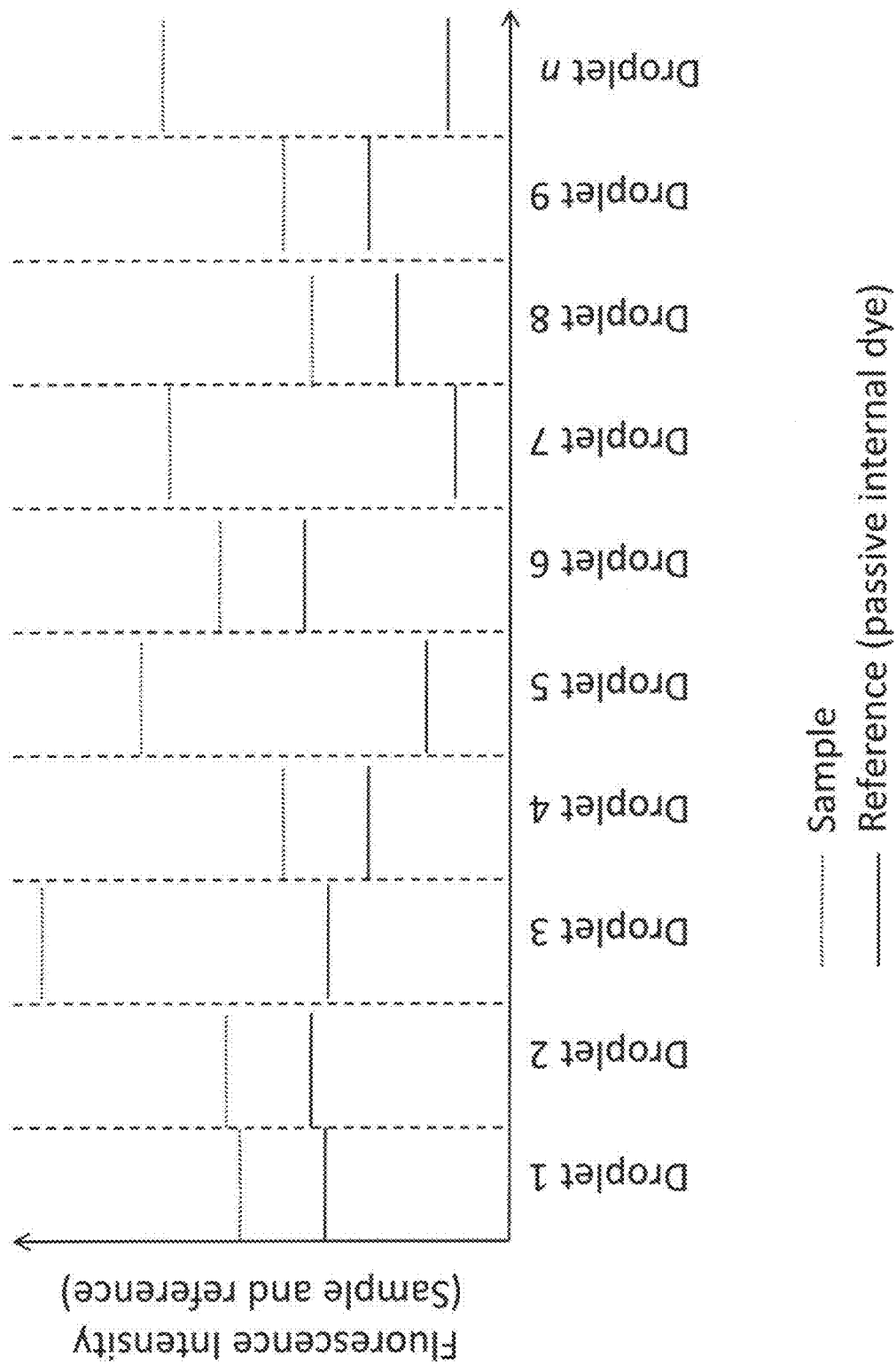
FIG. 18B is a drawing depicting end point sample and passive dye fluorescence values for a number of partitions that have been amplified in a digital PCR reaction protocol.

In a basic normalization process, after digital PCR amplification is completed, the relative fluorescence is calculated for each partition and a threshold is set for discriminating between positive and negative partitions. FIG. 18A is a graph illustrating a typical real time amplification curve for a partition containing both the sample material and a passive reference dye. FIG. 18B is a drawing depicting end point sample and passive dye fluorescence values for a number of partitions that have been amplified in a digital PCR reaction protocol. There is variation in the absolute fluorescence intensity that may be due to non-uniform optical illumination, sub-optimal thermal gradients, and other non-PCR related variations. Under such circumstances, it is difficult to set a threshold value that easily discriminates between positive and negative partitions.

Figure 18C:
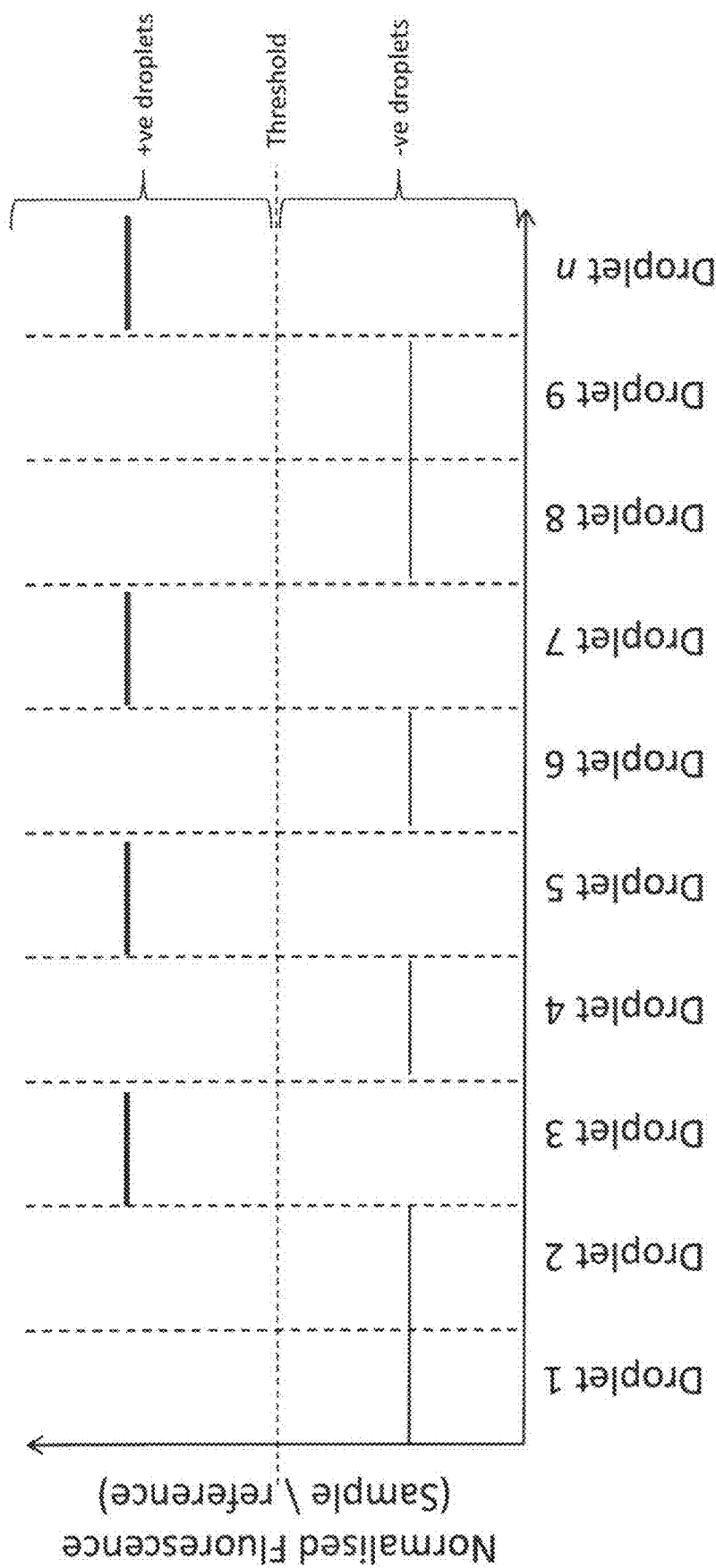
FIG. 18C is a drawing depicting relative fluorescence for the same partitions as in FIG. 18B.

This difficulty is resolved by application of Eqn. 8. Specifically, FIG. 18C is a drawing depicting relative fluorescence for the same partitions calculated using Eqn. 8. As seen in such figure, discrimination between positive and negative partitions is now much more distinct. A threshold therefore can be set that easily and correctly identifies positive from negative partitions, thereby eliminating the difficulty illustrated in FIG. 18B.

FIGS. 19A-19G are drawings depicting a progression of steps constituting another exemplary method of performing a digital PCR reaction protocol in accordance with embodiments of the present invention, including using multiple primers associated with multiple target portions within the DNA sample. FIGS. 19A-19G illustrate and exemplary assay protocol for a single DNA sample screened against four different primer targets, processed on a single EWOD device such as the EWOD cartridge 180. Each of the targets may have the same or different readout mechanisms, and may or may not have fluorescence excitation and emission wavelengths that are the same.

Figure 19A:
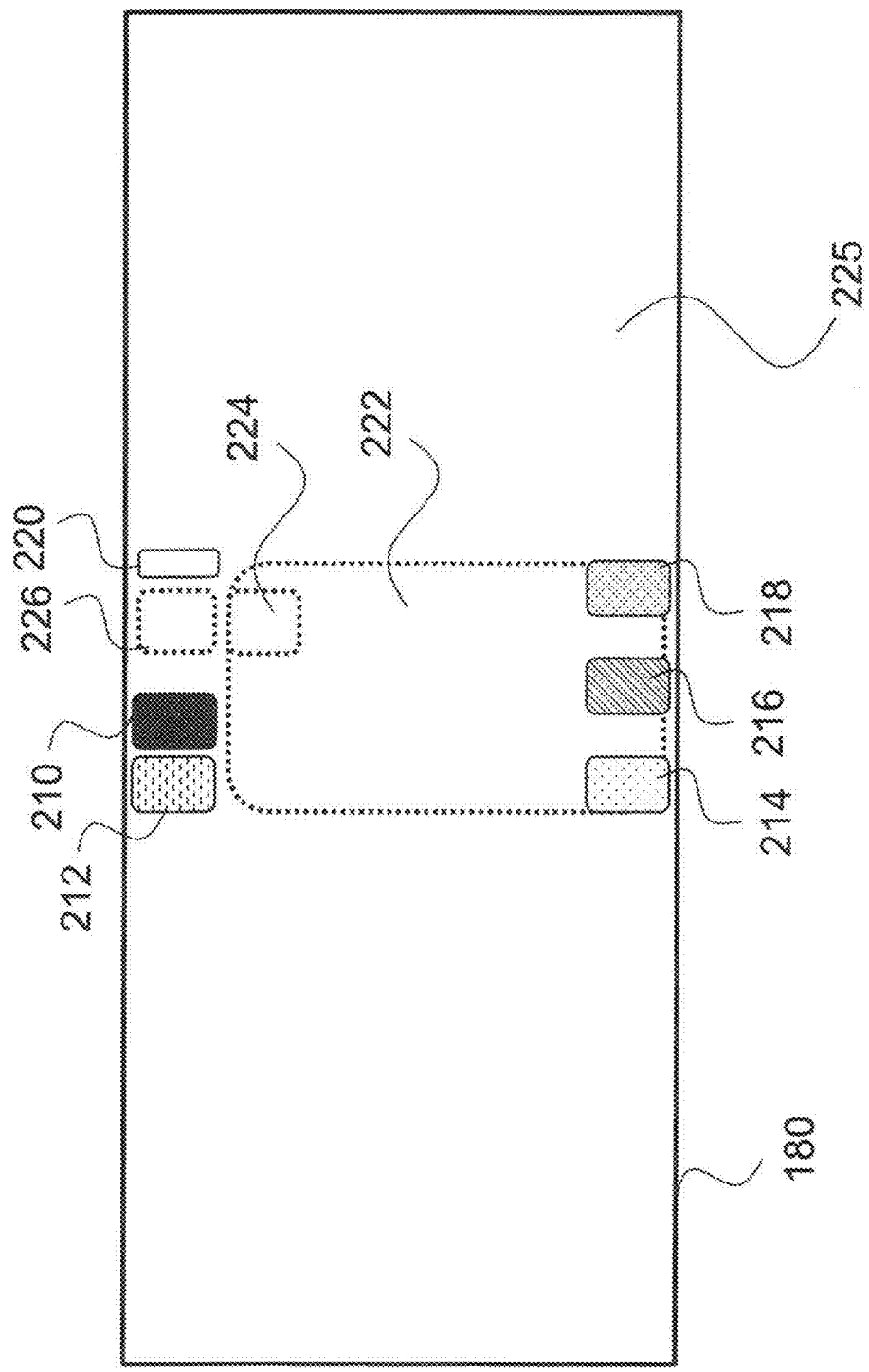
FIG. 19A, FIG. 19B, FIG. 19C, FIG. 19D, FIG. 19E, FIG. 19F, FIGS. 19G, and 19H are drawings depicting a progression of steps constituting another exemplary method of performing a digital PCR reaction protocol in accordance with embodiments of the present invention, including using multiple primers associated with multiple target portions within the nucleic acid sample.

FIG. 19A is a drawing depicting the EWOD device 180 into which there is inputted a DNA sample input volume 210, four target input volumes 212, 214, 216, and 218, and a quantification target input volume 220. The electrowetting elements may be actuated so as to form a sample preparation zone 222, a first nucleic amplification zone 224, a digital PCR zone 225, and a waste zone 226. The four target input volumes each contains the mastermix, primers and probes required for PCR amplification, but the primers target a different region on the strand of the DNA in the DNA sample input volume 210. Although four target input volumes are used in this example, any suitable number of target input volumes may be employed. The quantification target input volume 220 contains the mastermix, primers and probes required for PCR amplification against a quantification target which can be used to measure a Ct value and estimate the concentration of the original sample.

Figure 19B:
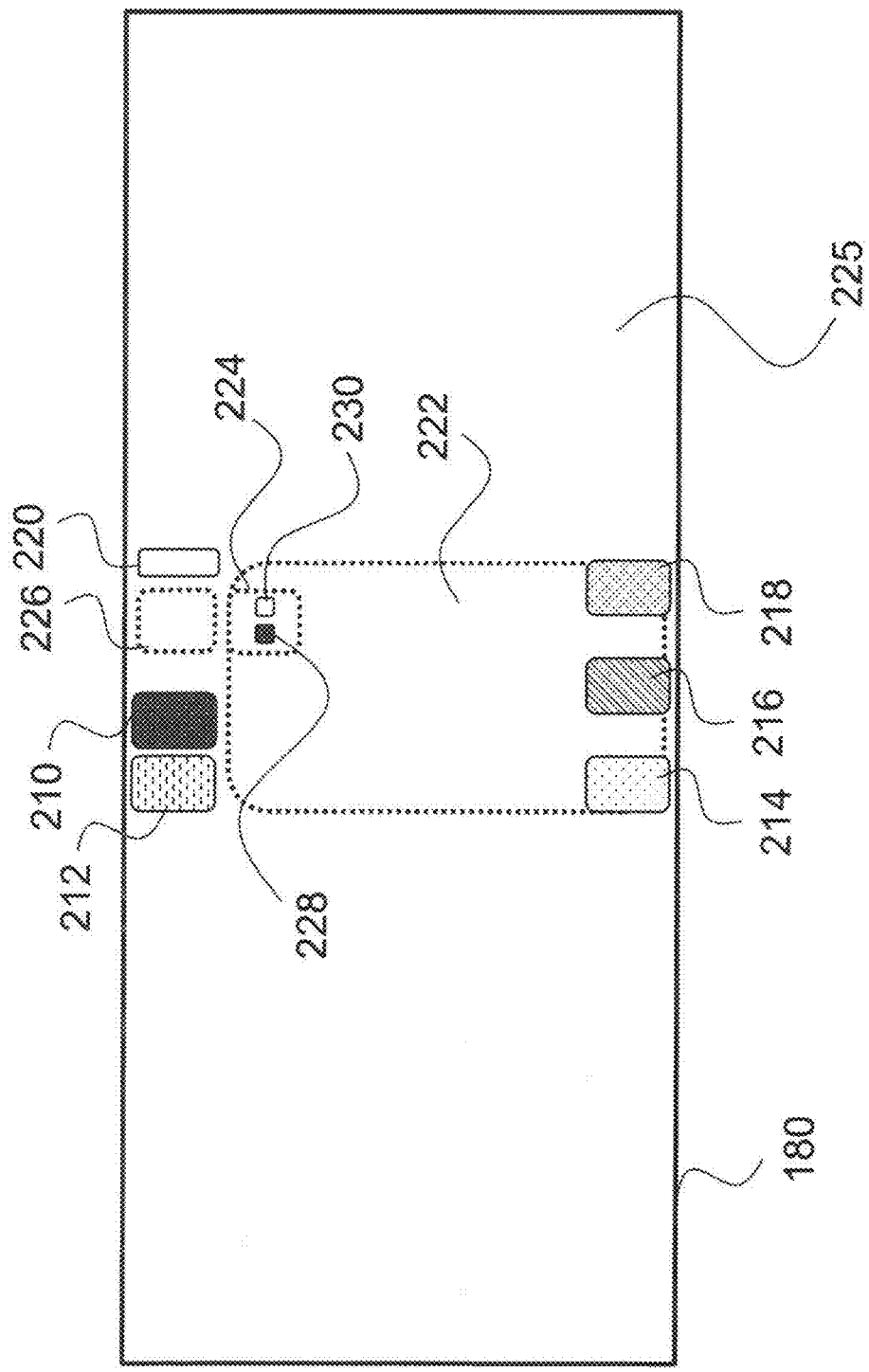
Figure 19C:
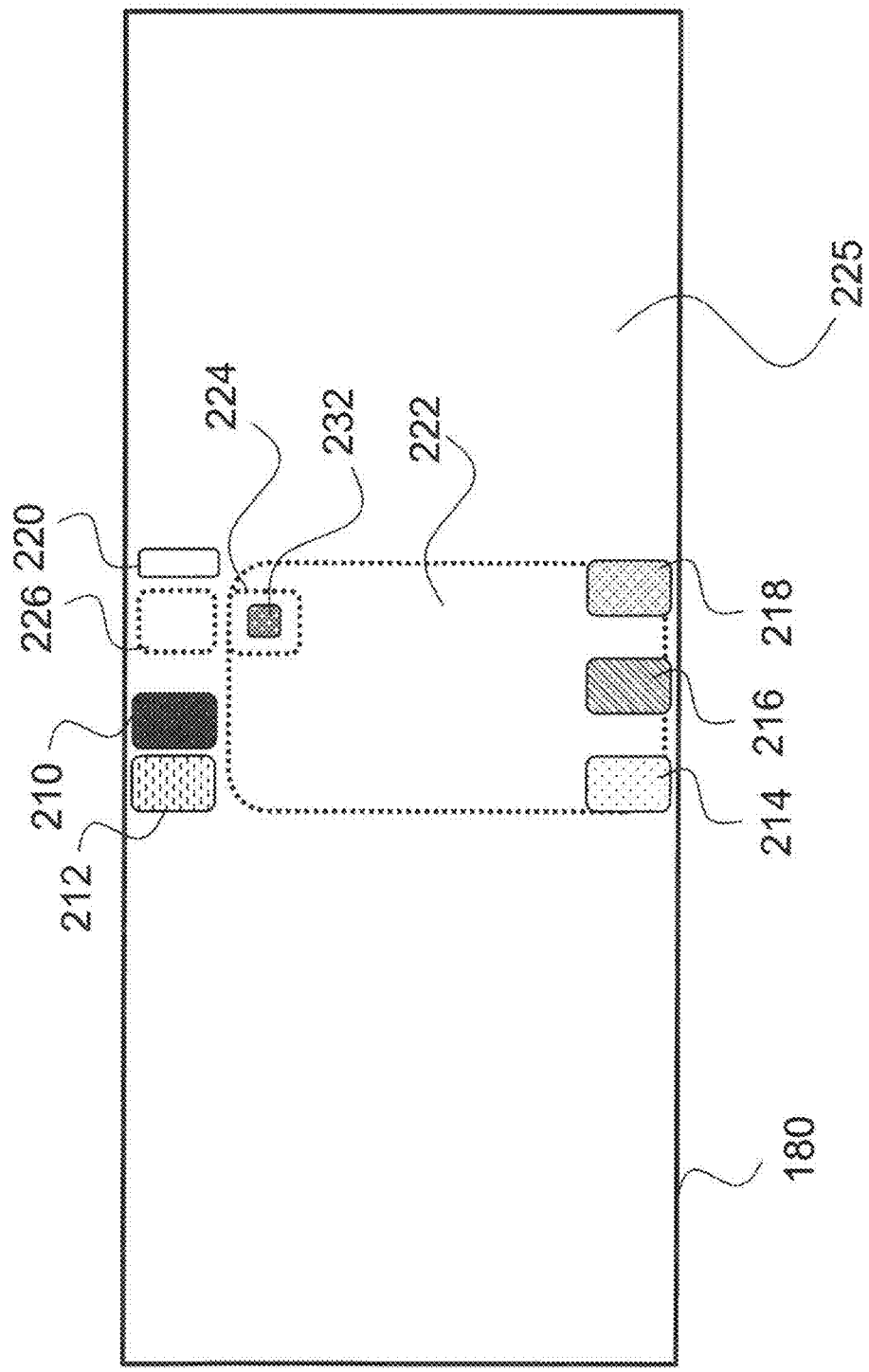
Figure 19D:
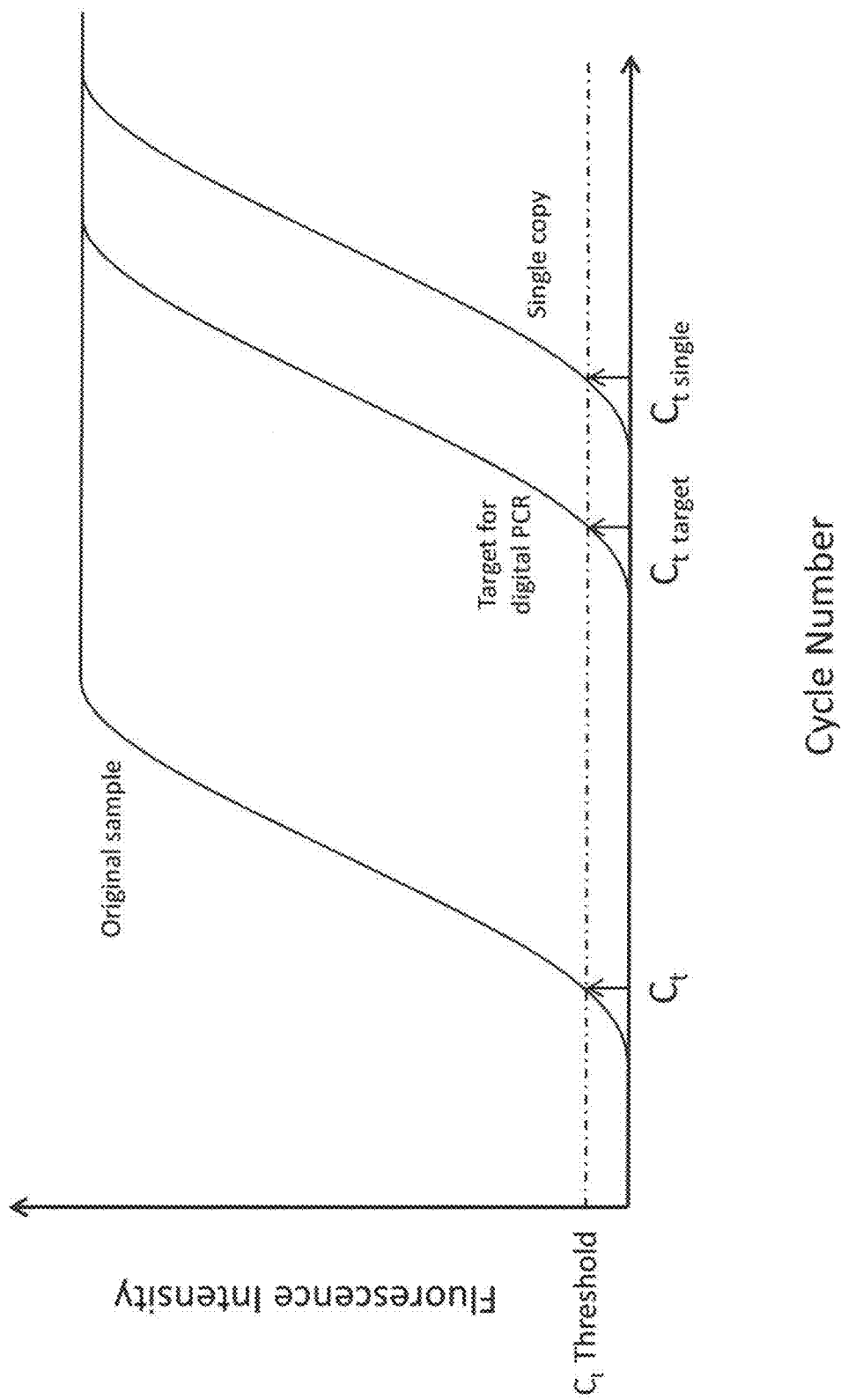

In an initial preparation step as illustrated in FIG. 19B, a first sample droplet 228 is dispensed from the sample input volume 210, and a quantification droplet 230 is dispensed from quantification target input volume 220, which is used to determine the appropriate dilution factor. Such droplets are moved into the first nucleic acid amplification zone 224. As illustrated in FIG. 19C, the first sample droplet 228 and quantification droplet 230 are mixed and merged within the first amplification zone 224 to form an amplifying droplet 232. Referring back to the drawings illustrating a 12-element configuration of the thermal control elements, the thermal control element corresponding to the first amplification zone 224 is element four in this example. Such thermal control element is controlled to thermally cycle the amplifying droplet 232 between 95° C. and 60° C. to perform a PCR amplification process. An optical measurement is taken each time the fourth thermal control element is at 60° C., and the fluorescence intensity against cycle number is plotted comparably as in the previous embodiments. FIG. 19D therefore is a graph depicting the fluorescence intensity used to determine the Ct value of the DNA sample. Once the fluorescence value is greater than the pre-defined threshold and the Ct value can be determined, thermal cycling is halted, and the amplified droplet 232 is moved to the waste zone 226 as shown in FIG. 19E.

The system then uses a saved reference Ct-target for the reaction and the measured Ct value from FIG. 19D to estimate the concentration of the original DNA sample. The Ct for the original sample can then be used with the Ct-target of the target concentration for digital PCR quantification in Eqn. 7 to calculate the dilution factor for sample quantification.

Figure 19E:
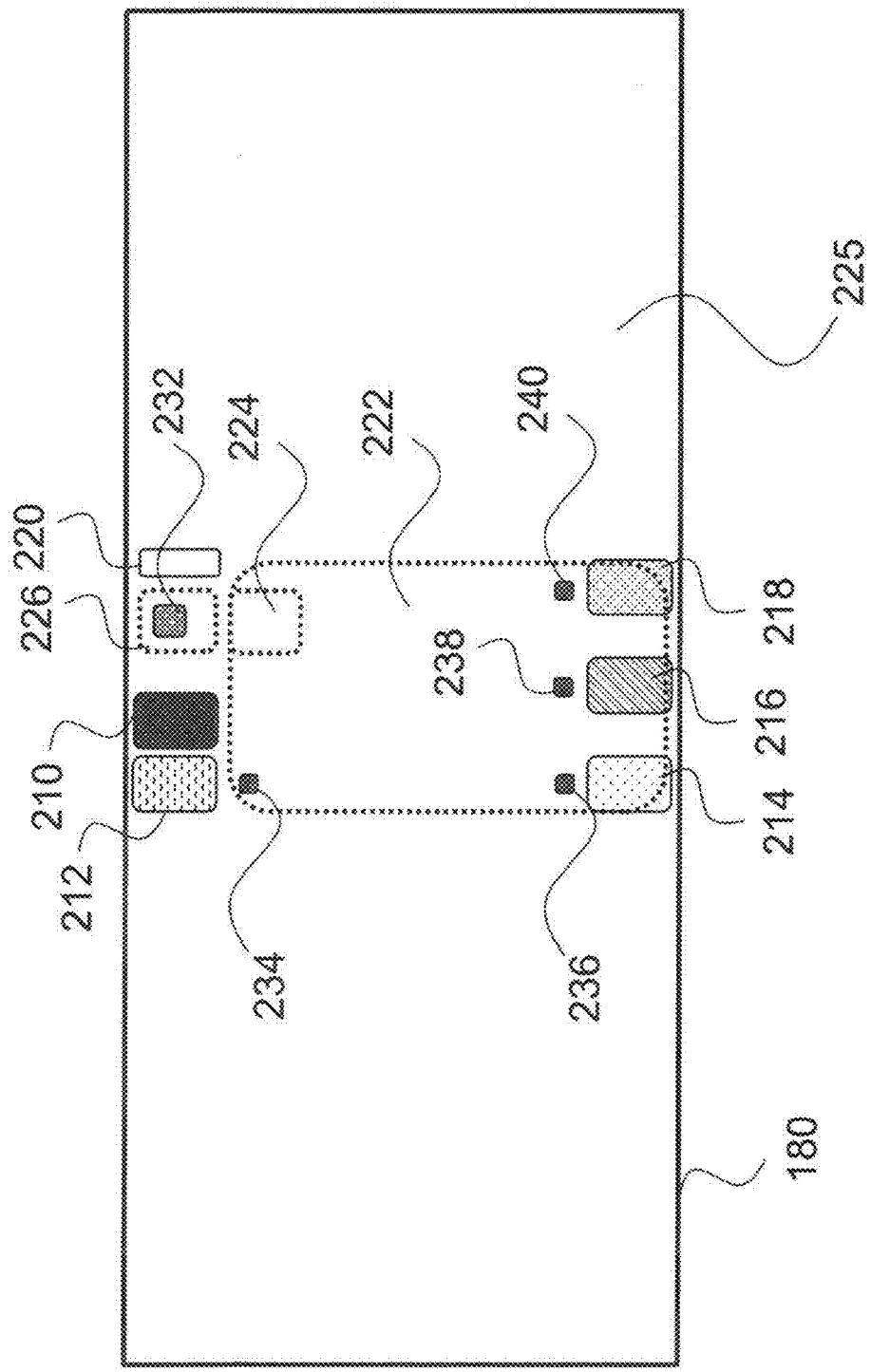
Figure 19F:
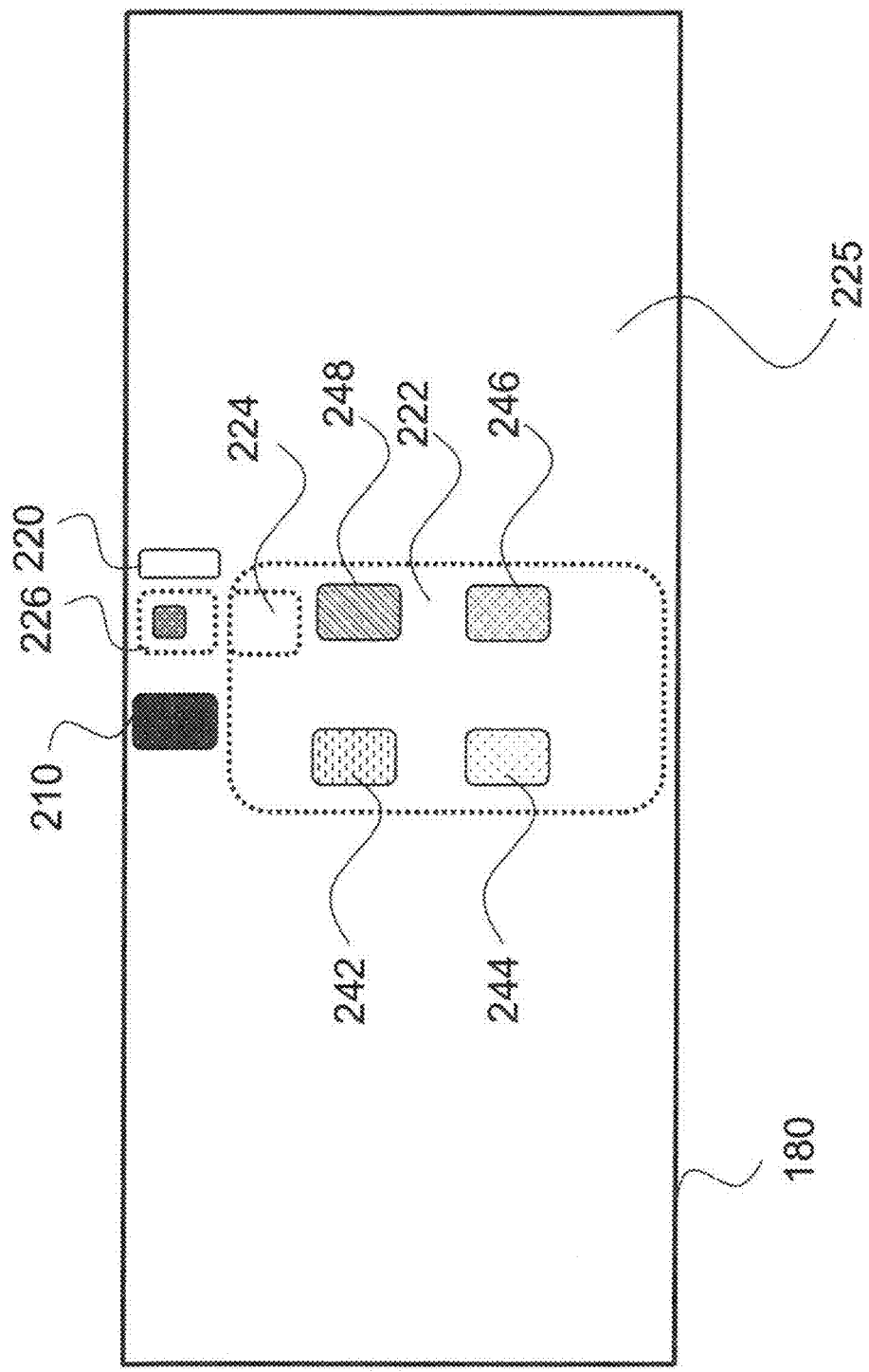
Figure 19G:
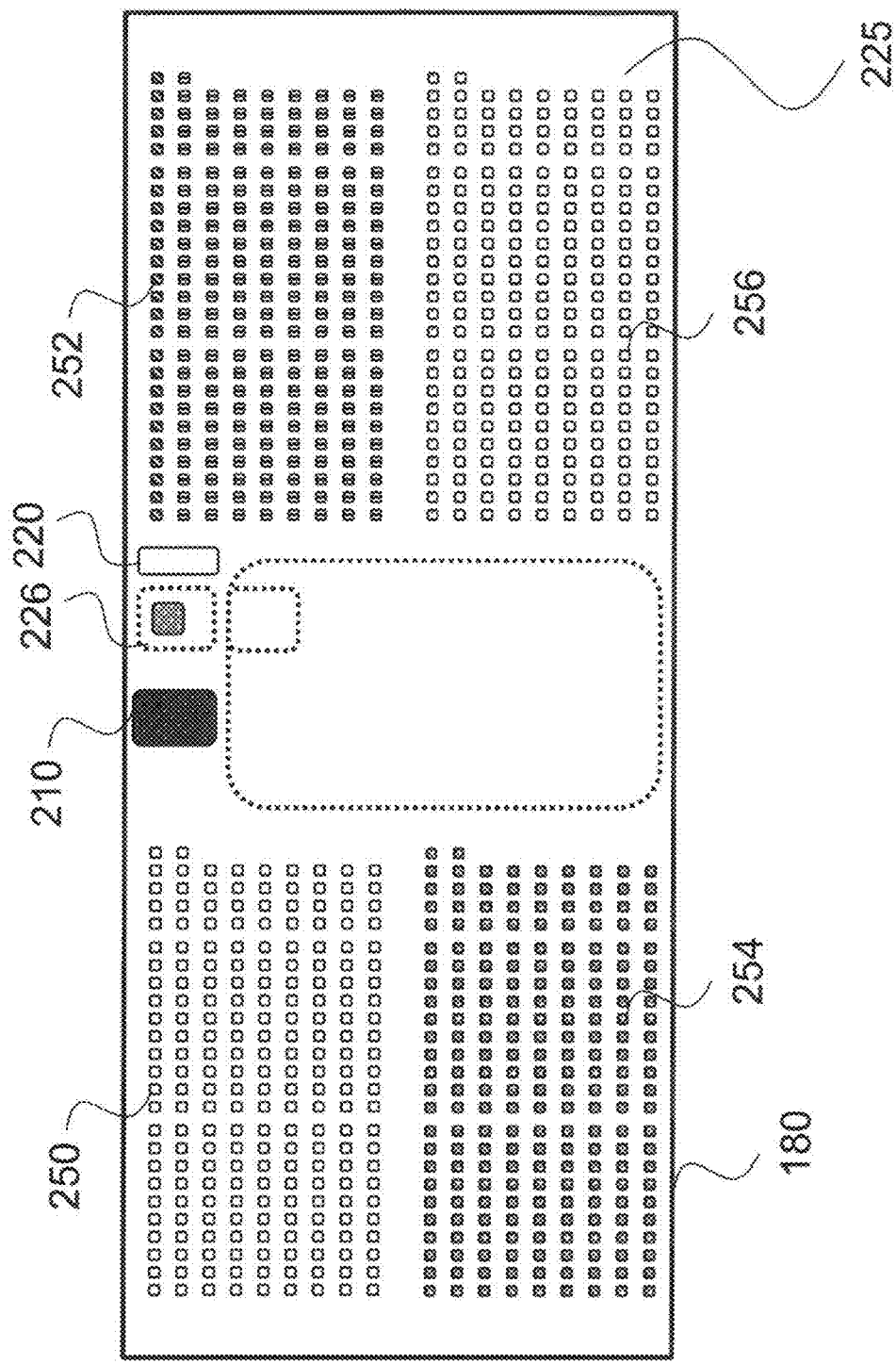

As further shown in FIG. 19E, the system automatically dispenses by electrowetting forces four sample daughter droplets 234, 236, 238, and 240 into the sample preparation zone 222. As illustrated in FIG. 19F, in accordance with the calculated dilution factor from the previous step, the sample daughter droplets respectively are diluted with the four target input volumes to create four respective diluted sample/target combinations 242, 244, 246, and 248. As illustrated in FIG. 19G, each of the four diluted sample/target combinations is partitioned into a number of partitions and moved into the digital PCR zone 225 by electrowetting. Again, the digital PCR zone 225 preferably excludes the first amplification zone 224 so that any possible contamination issues can be avoided.

Figure 19H:
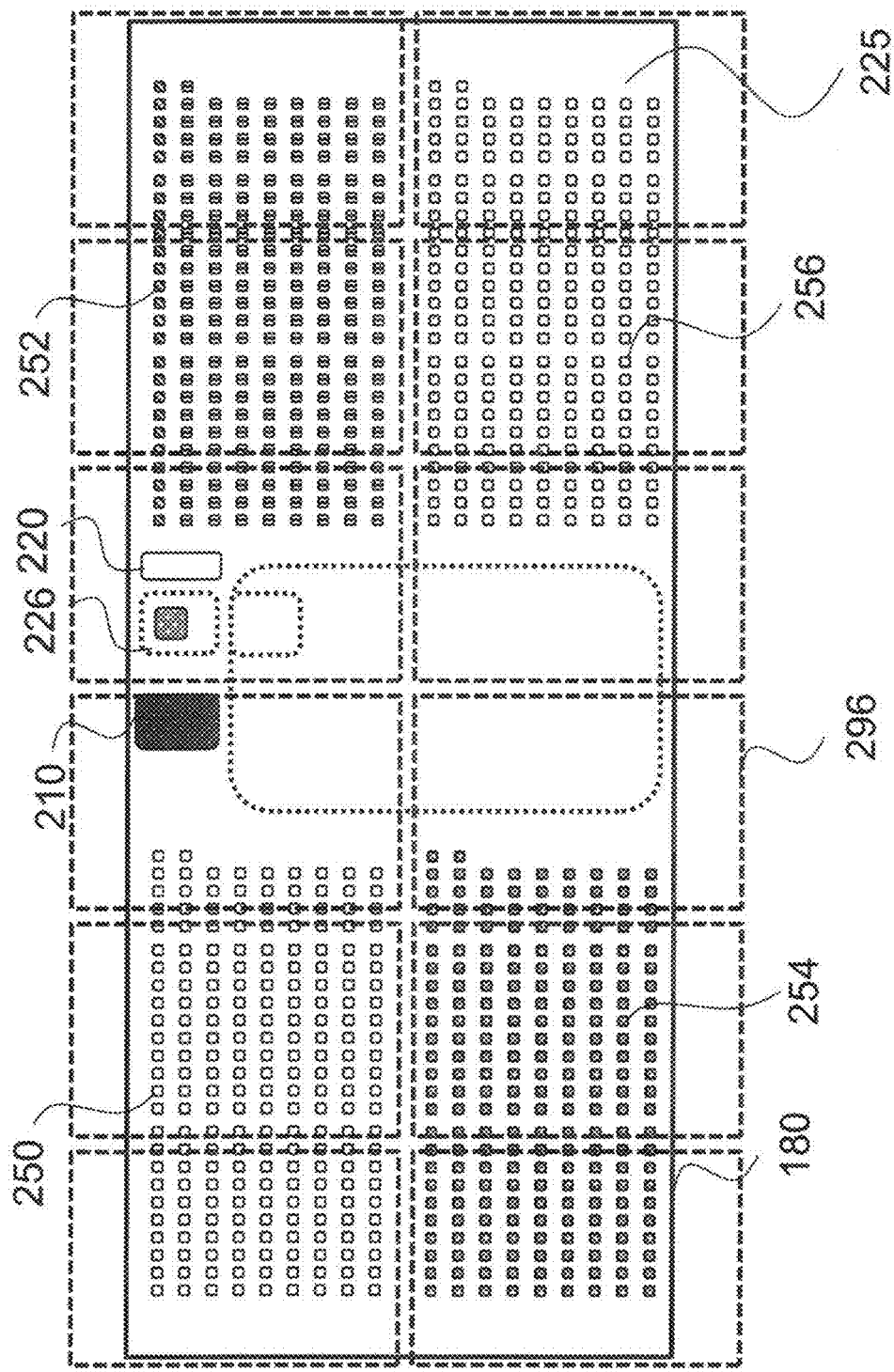

As illustrated in FIG. 19H, in a preferred embodiment, each of the diluted sample/target combinations 242, 244, 246, and 248 is split into respective partitions 250, 252, 254, and 256 for quantification. To perform the digital PCR, referring back to the drawings illustrating a 12-element configuration of the thermal control elements, thermal control elements 1-3 can then be set to thermally cycle all of the partitions between 95° C. and 60° C. for the partitions 250 containing target 212; thermal control elements 4-6 can then be set to thermally cycle all of the partitions between 95° C. and 60° C. for the partitions 252 containing 216; thermal control elements 7-9 can then be set to thermally cycle all of the partitions between 95° C. and 60° C. for the partitions 254 containing target 214; and thermal control elements 10-12 can then be set to thermally cycle all of the partitions 256 between 95° C. and 60° C. for the sample containing target 218. After, typically 35-45 cycles, the number of positive and negative partitions can be counted. Poisson statistics (Eqns. 3-6) can then be used to absolutely quantify the original sample concentration relative to each target portion of the sample DNA. Each sample/target combination may be quantified using as few as 218 droplets.

It will be understood that the above exemplary embodiments are not meant to be limiting. The various embodiments may be combined and utilized with different EWOD platform technologies. One skilled in the art will recognize that any number of different assay geographies may achieve the desired outcomes using the general principles set forth herein. For example, in some instances, the DNA sample may be dispensed separately from the primers, probes and mastermix, which can then be mixed on the EWOD device prior to the first amplification stage. Examples are set forth in, but not limited to, the following Table I.

TABLE I

| | Fluid input 1 | Fluid input 2 | Fluid input 3 | Fluid input 4 |
| --- | --- | --- | --- | --- |
| Combination 1 | DNA sample, mastermix, primers & probe(s) | | | |
| Combination 2 | DNA sample | Mastermix with primers & probe(s) | | |
| Combination 3 | DNA sample | Mastermix | Primers & probe(s) | |
| Combination 4 | DNA sample | Mastermix | Primers | Probe(s) |

Principles of the present invention also are applicable for reaction protocols in which the nucleic acid input is RNA. Complementary DNA is prepared from RNA using a reverse-transcription (RT) step. This is then followed by nucleic acid amplification. Reagents for RT and PCR may be mixed in a 1-step RT-PCR protocol, or added in two steps. The two-step protocol adds the RT reagents and performs reverse-transcription before adding the PCR reagents for amplification. For a 1-step RT-PCR protocol, the mastermix in the above Table I would be replaced by a 1-step RT-PCR mastermix.

It will also be understood by those of ordinary skill in the art that principles of the present invention are not limited to digital PCR assays, and that the principles of the present invention are fully compatible with digital assays in biology, such as for example digital nucleic acid quantitation, ELISA for protein biomarker quantitation, enzymatic assays for quantitation of enzymatic turnover and cell based assays for phenotyping and genotyping.

It will be further understood by those of ordinary skill in the art that principles of the present invention are fully compatible with isothermal qPCR techniques and isothermal digital PCR techniques. Isothermal techniques do not require traditional thermal cycling between 95° C. and 60° C. during the reaction cycles. Instead, isothermal amplification is performed at a fixed temperature. In the present invention, the fixed temperature required for isothermal techniques can be provided by the programmable thermal control elements under the cartridge in the EWOD system. The current invention is compatible with isothermal techniques including, but not limited to, recombinase polymerase amplification (RPA), loop-mediated isothermal amplification (LAMP), strand displacement amplification (SDA), helicase-dependent amplification (HAD), rolling circle amplification (RCA), and nicking enzyme amplification reaction (NEAR).

In isothermal methods, the fluorescence intensity of the reaction is monitored with respect to time rather than "per cycle" as is done in PCR. The time at which the sample fluorescence is greater than a given threshold is called the "time to positive" or Tp value. Samples of different concentrations produce different Tp values. Using standards, e.g. samples of known concentration, Tp values can be established for a range of sample concentrations. A correlation between "Tp" and "sample concentration" can then be determined in a way analogous to "Ct" against "sample concentration" in qPCR.

It will be further understood by those of ordinary skill in the art that principles of the invention are fully compatible with digital protein assays. Digital protein assays may be used to quantify proteins in samples, particularly low abundance biomarker proteins in serum samples using the ELISA. (ELISA is a widely used technique to detect any protein that can be bound to an antibody) or to quantify enzymes that have enzymatic activity.

It will be further understood by those of ordinary skill in the art that principles of the invention are fully compatible with digital cell based assays. Digital cell based assays involve the encapsulation of discrete numbers of cells in partitions and the measuring of features of cell phenotype and genotype e.g. cell secretions, cell surface biomarkers, cell metabolites etc usually by partitioning cells into partitions containing fluorogenic substrates for enzymatically amplified detection.

Figure 20:
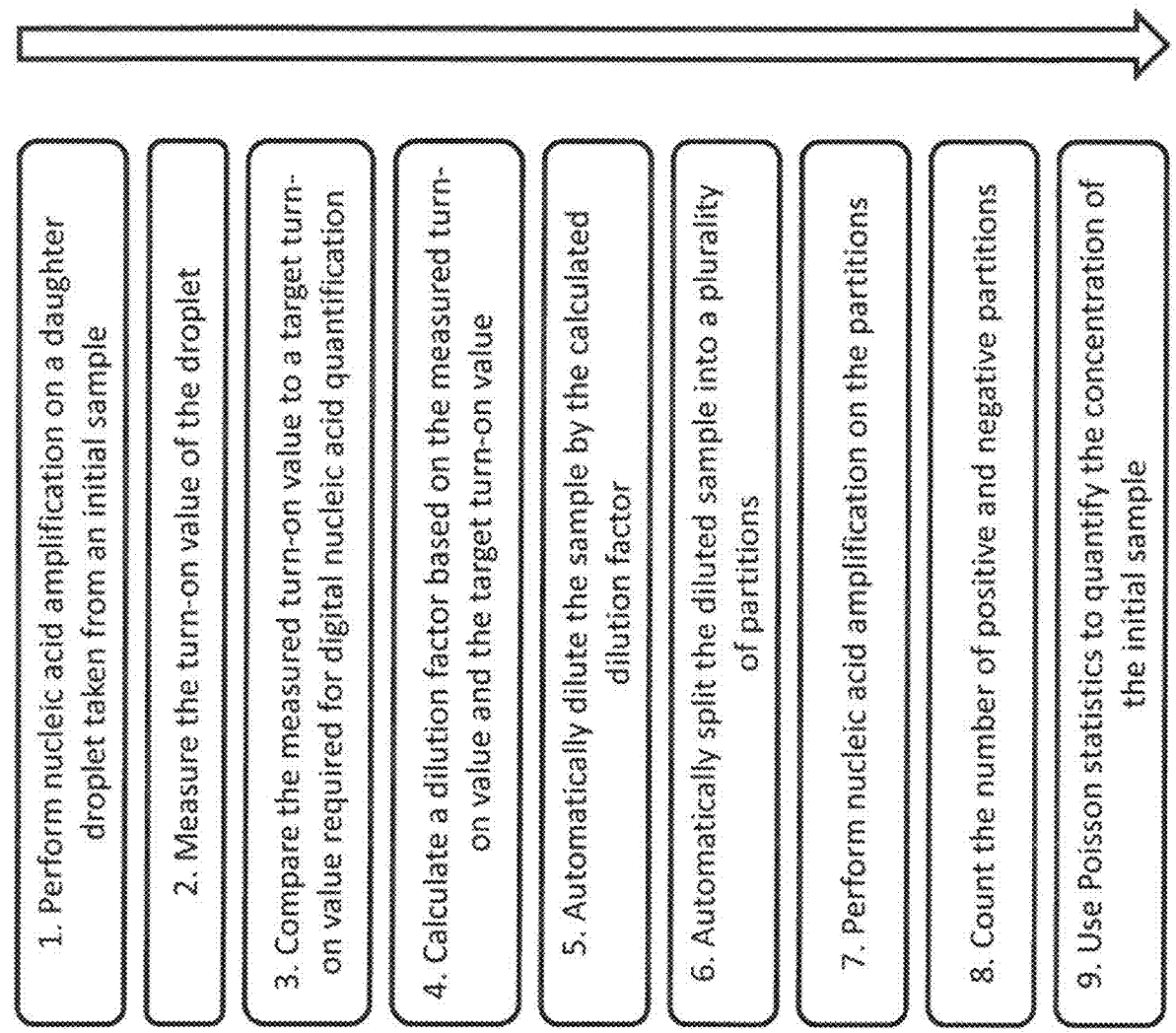
FIG. 20 is a flow chart diagram depicting an exemplary method of quantifying a concentration of a target nucleic acid in a sample volume.

To encapsulate the general principles of the invention, FIG. 20 is a flow chart diagram depicting an exemplary method of quantifying a concentration of a target DNA in a sample volume. Exemplary methods and any related sub-steps may be programmed into the control systems and computer based elements incorporated into the EWOD system, such as, for example, the control elements described previously with respect FIGS. 2, 8, and 12. The steps of the method may include the following: (1) performing an amplification on a sample droplet dispensed from an initial sample volume; (2) measuring the turn-on value (e.g. Ct, Tp, copies/20 uL, copies/uL or copies/partition) of the sample droplet; (3) comparing the measured turn-on value to a target turn-on value for supporting subsequent digital nucleic acid quantification (e.g. 0.7-1.6 copies/partition); (4) calculating a dilution factor based on the measured turn-on value and the target turn-on value; (5) automatically diluting a portion of the sample volume by the calculated dilution factor; (6) automatically splitting the diluted sample portion into a plurality of partitions; (7) performing a digital amplification process on the partitions; (8) counting the number of positive and negative partitions; and (9) using Poisson statistics to quantify the concentration of the initial sample. Principles of the invention are further quantified in the following examples.

Example 1: qPCR Measurement on a Droplet to Determine Sample Concentration and Dilution Factor Approximately ~1 uL of a DNA sample of an unknown concentration is loaded onto an EWOD device. A 2×2 droplet, 0.0229 uL, is split from the sample using electrowetting and is transferred to an amplification zone. The fluorescence of the droplet is measured after each thermal cycle, and the fluorescence intensity as a function of PCR cycle number is recorded and analyzed in the system control software. When the intensity of the fluorescence signal amplifies above the threshold value, the Ct value for the sample is calculated automatically. The Ct value for the sample of unknown concentration is compared to a reference database of reactions saved on the systems' computer. The Ct value is used to estimate the concentration of the original sample using a reference standard curve for the reaction being performed.

In this example, for a given reaction, the Ct value of the unknown starting sample is measured to be 21. For said given reaction, the system computer includes a reference relationship of:

$$Y=-3.3x+34.8$$

where y is the Ct value and x is the log of DNA concentration (copies/20 ul).

For a sample measured with a Ct value of 21, the concentration of the unknown sample would be estimated as ~15,199 copies per 20 ul (or 756 copies per uL). Given that it is known that the system will partition 20 uL of the final sample volume into 873×0.0229 uL partitions, and that the optimal concentration for digital PCR is typically between 1-1.6 copies per partition, the system can calculate that the target sample concentration is between 873 and (873*1.6=) 1,396 copies in the 20 uL that will be analyzed (43.62-69.6 copies/uL). The reference standard curve equation above can be used to calculate the $Ct_{target\ digital\ PCR\ concentration}$ of between 24.4 and 25.1.

Assuming that the efficiency of the reaction is 100%, e.g. the DNA concentration doubles every PCR cycle and efficiency in the equation is therefore 2, and the target copy number is 1.6 copies per partition (Ct=24.4), the dilution factor required would be:

$$\text{Dilution Factor} = \text{Efficiency}^{\wedge}(Ct_{target} - Ct)$$
$$= 2^{\wedge}(24.4 - 21)$$
$$= 2^{\wedge}3.4$$
$$= 10.55$$

The system can then calculate the optimal diluent amount based on the smallest droplet size, 0.0229 uL. Under these circumstances, 10.55*0.0229=0.241595 uL=>0.241595-0.0229=0.218695 uL diluent is required for each 0.0229 uL sample droplet. If 20 uL has to be processed, 20/0.241595=82.78 repeats of this basic unit; 82.78*0.0229=1.895 uL of sample and 82.78*0.218695=18.10 uL of diluent. Given that 10 uL is approximately equivalent to a 42×42 pixel droplet, it would be possible to mix two 10 uL final dilution volumes in parallel to achieve the 20 uL required for digitization, e.g. two parallel dilutions of 0.9475 uL sample into (10−0.9475=)9.0525 PCR reagent.

After dilution, the concentration will be ~1.6 copies per partition. Using Poisson statistics, the digital PCR output would yield 696 out of the 873 partitions as being positive, and 177 out of the 873 partitions as negative. In this example, just over $\frac{2}{3}^{rd}$ of the cartridge is required to accommodate the 873 partitions for thermal cycling, enabling approximately another $\frac{1}{3}^{rd}$ to be dedicated to sample preparation and dilution.

The digital quantification step identifies which partitions are positive and which are negative. In one aspect, the digital quantification step counts the number of positive partitions and/or the number of negative partitions. In this example, there are 696 positive partitions and 177 negative partitions from a total of 873 partitions.

In a further aspect, Poisson's statistics (Eqns 3-6) are used to calculate the concentration of the diluted sample droplet. Using a partition volume of 0.0229 uL with 551 positive partitions, 322 negative partitions, the diluted sample concentration k is calculated to be 69.68 copies/uL.

In yet further aspects, the concentration of the diluted sample droplet (as calculated via Poisson's statistics) can be used with the dilution factor data to calculate the concentration of the initial sample. In this instance, the initial sample concentration would be calculated as 69.68*10.55=735 copies/uL, or 14,702 copies/20 uL. Additionally and/or alternatively, the target copy number may be set as 1 copy per partition (Ct=25.1). Assuming that the efficiency of the reaction is 100%, e.g. it doubles every PCR cycle and efficiency in the equation is therefore 2, the dilution factor required would be:

$$\text{Dilution Factor} = \text{Efficiency}^{\wedge}(Ct_{target} - Ct)$$
$$= 2^{\wedge}(25.1 - 21)$$
$$= 2^{\wedge}4.1$$
$$= 17.15$$

The system can then calculate the best dilution ratio based on the smallest droplet size, in this instance assumed to be 0.0229 uL.

Additionally and/or alternatively, the dilution factor can be calculated as follows:

$$\text{Dilution Factor} = \text{measured copies per } ul \text{ in sample} / \text{target copies per } ul \text{ for digital PCR}$$
$$= 756/43.62$$
$$= 17.33$$

The differences are predominantly due to rounding errors in the respective calculations. Under such circumstances, 17.15*0.0229=0.392735 uL=>0.392735-0.0229=0.369835 uL diluent is required for each 0.0229 uL sample droplet. If 20 uL has to be processed, 20/0.392735=50.92 repeats of this basic unit; 50.92*0.0229=1.166 uL of sample and 50.92*0.369835=18.83 uL of diluent. Given that 10 uL is approximately equivalent to a 42×42 pixel droplet, it would be possible to mix two 10 uL final dilution volumes in parallel to achieve the 20 uL required for digitization, e.g. two parallel dilutions of 0.583 uL sample into (10-0.583=) 9.417 uL PCR reagent.

After dilution, the concentration will be ~1 copy per partition. Using Poisson statistics, the digital PCR output would yield 551 out of the 873 partitions as positive, and 322 out of the 873 partitions as negative. In this example, just over $\frac{1}{3}^{rd}$ of the cartridge is required to accommodate the 873 partitions for thermal cycling, enabling approximately another $\frac{1}{3}^{rd}$ to be dedicated to sample preparation and dilution. Additionally and/or alternatively, the target copy number may be set as any value between 1 and 1.6 copies per partition (Ct=24.4 and 25.1), or more broadly, set to any value between 0.7 and 2.5 copies per partition, or even more broadly set to any value between 0.002 and 9 copies per partition where 873 partitions of 0.0229 uL volume are used.

The digital quantification step identifies which partitions are positive and which are negative. In one aspect, the digital quantification step counts the number of positive partitions and/or the number of negative partitions. In this example, there are 551 positive partitions and 322 negative partitions from a total of 873 partitions.

In a further aspect, Poisson's statistics (Eqns 3-6) are used to calculate the concentration of the diluted sample droplet. Using a partition volume of 0.0229 uL with 551 positive partitions, 322 negative partitions, the diluted sample concentration k is calculated to be 43.55 copies/uL.

In a further aspect, the concentration of the diluted sample droplet (as calculated via Poisson's statistics) can be used with the dilution factor data to calculate the concentration of the initial sample. In this instance, the initial sample concentration would be calculated as 43.55*17.15=747 copies/uL, or 14,938 copies/20 uL.

Example 2: Inefficient Reactions

A first sample droplet shows a Ct1 of 21 and a 10-fold dilution of the sample has a Ct2 of 24.5. The efficiency of the reaction is:

$$\text{Efficiency} = 10^{\wedge}(1/(Ct2 - Ct1)) = 10^{\wedge}(1/\Delta n)$$
$$= 10^{\wedge}(1/24.5 - 21)$$
$$= 10^{\wedge}(0.2857)$$
$$= 1.93$$

The system computer has a reference Ct value for the target concentration for digital PCR quantification for the specific reaction, $Ct_{target}$=25.0. The dilution factor can then be calculated as follows:

$$\text{Dilution Factor} = \text{Efficiency}^{\wedge}(Ct_{target} - Ct)$$
$$= 1.93^{\wedge}(25 - 21)$$
$$= 1.93^{\wedge}4$$
$$= 13.87$$

Additionally and/or alternatively, if the system database has a reference equation for the reaction, the system can calculate the target dilution factor by estimating the concentration of the initial sample and knowing what the optimal copy number range is for digital PCR quantification. An example reference standard equation is:

$$Y=-3.5x+36$$

where y is the Ct value and x is the log of DNA concentration.

The system can then calculate the concentration of the initial sample; approximately 19,307 molecules/20 uL or 965 copies/uL. Given that it is known that the system will partition 20 uL of the final sample volume into 873×0.0229 uL partitions, and that the optimal concentration for digital PCR is between 1-1.6 copies per partition, the system can calculate that the target sample concentration is between 873 and (873*1.6=) 1,396 copies in the 20 uL that will be analyzed (43.62-69.6 copies/uL). The reference equation for the reaction above can be used to calculate the Ct target at between 25.0 and 25.7 further taking into account the calculated efficiency of reaction.

$$\text{Dilution Factor} = \text{Efficiency}^{\wedge}(Ct_{target} - Ct)$$

| | |
|---|---|
| $= 1.93^{\wedge}(25 - 21)$ | $= 1.93^{\wedge}(25.7 - 21)$ |
| $= 1.93^{\wedge}(4)$ | $= 1.93^{\wedge}(4.7)$ |
| $= 13.87$ | $= 21.98$ |

Example 3: Dilutions on EWOD to Extend the Dynamic Range of Digital PCR Using a Restricted Number of Droplets Consider an example in which 20 uL is partitioned into 873 droplets and analyzed on the EWOD platform, and the sample and diluent/PCR amplification reagents are all stored on the EWOD device. Applying Poisson statistics and assuming that you need 20% or more droplets to be negative for optimal results, then 873×0.0229 uL partitions (or 36×0.0229 uL partitions totaling 10 uL) will allow samples up to a bulk concentration of ~70 molecules/uL to be quantified. This is equivalent to 1,400 molecules per 20 uL. The dynamic range can be calculated as follows:

No of logs=log(70)−log(1)=1.845−0=1.85

To extend the dynamic range of the platform, sample dilutions can be performed on the EWOD device. 10 uL of diluent/PCR reagent occupy 42×42 pixels. The smallest partition allowed is 2×2 pixels, or 0.0229 uL. If an area of ~6,825 pixels (e.g. 105*65 pixels or similar) is dedicated to diluting samples, then it is possible to achieve a maximum sample dilution of 0.0229 uL into 10 uL, or a 437-fold dilution. This means that a maximum bulk sample concentration of 437*70=30,590 molecules/uL (equivalent to ~6×10$^5$ molecules per 20 uL) to be quantified digitally once the dilution factor is taken into consideration. The dynamic range of the system is:

No of logs=log(30,590)−log(1)=4.486−0=4.49

Given the capacity of the cartridge, the system can perform a second 437-fold dilution using a further 10 uL of diluent/PCR reagent, enabling 437*30,590=13,367,830 molecules/uL (equivalent to ~2.7×10$^8$ molecules per 20 uL) to be quantified digitally, taking both dilution factors into consideration. The dynamic range of the system is calculated as follows:

No of logs=log(13,367,830)−log(1)=7.126−0=7.13

The dilution is performed twice to get the 20 uL worth of diluted sample for partitioning, e.g. process the 2×10 uL dilution steps twice.

More dilutions can be performed as required.
The dynamic range of the EWOD system is now greater than that specified for a digital PCR system that divides ~25 uL into 5 million partitions.

Example 4: Mutant:Wildtype Ratio 1:1000

In a particular sample, the ratio of mutant:wildtype is 1:1000. To ensure confidence in an end result, a researcher decides that a minimum of 5 mutants must be positively identified. Therefore, an EWOD device is employed to digitize a given input sample volume (a) to the optimal digital PCR concentration and (b) into a sufficient number of partitions to detect 5 mutants. For a sample to contain ~5 mutants on average, it will also contain ~5000 wildtype molecules. This results in requiring at least 5005 molecules in an analysis sample.

The qPCR quantification step could look for amplification of both the wildtype (dominant) and mutant (if sample already sufficiently dilute). For a mutant:wildtype of 1:1,000, then the system knows that, to detect at least 5 mutants, the wildtype will have to be present at approximately 5000 molecules/20 uL (250 molecules/uL). Therefore, the dilution factor in this instance is determining the dilution required to bring the wildtype down to 250 molecules/uL.

For digital PCR, it has been estimated that between 0.7-1.6 copies/partition is the optimal concentration. Taking the two extremes, between (5005/0.7=)7,150 partitions and (5005/1.6=)3,128 partitions are required for analysis. This is equivalent to a partition volume of between 2.8 nL and 6.4 nL assuming a 20 uL sample processing volume. The EWOD platform uses 105 um×105 um pixels with a 75 um cell gap. Each pixel has a volume of 0.827 nL, so a minimum droplet size of 2×2 pixels would support a 3.3 nL partition volume. The footprint of the active area is 632×260=164,320 pixels.

If each 2×2 droplet requires a 2-pixel space between it and its nearest neighbor, then each 2×2 droplet requires 16 pixels. The highest density of partitions that could be accommodated would therefore be 164,320/16=10,270 partitions. If ¾ of the cartridge is dedicated to amplification of the partitions, then a maximum of 7,702 droplets could be accommodated. The remaining ¼ of the active area would be dedicated to sample prep and the first qPCR quantification step. A 20 ul volume on the cartridge would occupy an area ~156×156 pixels square and partition into 6,060×3.3 nL partitions.

Using Poisson statistics, for digital PCR performed on a 20 uL sample containing 5000 wildtype molecules per 20 uL (equivalent to 250 molecules/uL), then 6,060 partitions of 3.3 nL would yield 2,656 negative partitions, 3,404 positive partitions and a measured λ of 250 molecules/uL. There would be 5 mutant molecules in the mixture (equivalent to 0.25 molecules/uL) resulting in 5 positive partitions.

Example 5: Scaling Factor

In some embodiments, it is preferable to ensure the number of positive partition droplets is between 0.0001-90%, 0.001-80% or 0.01-50% of the total number of partitions. The present invention can be used to calculate a dilution factor that will ensure a minimum or preferred number of positive partitions.

For example, the Ct value of the unknown starting sample droplet is measured to be 21. For said given reaction, the system computer has a reference equation for the sample of:

$Y = -3.3x + 34.8$ where y is the Ct value and x is the log of DNA concentration. For a sample measured with a Ct value of 21, the concentration of the unknown sample would be estimated as ~15,199 copies per 20 ul (or 756 copies per uL). Assuming a minimum droplet volume of 0.0229 ul, a 20 ul sample could be partitioned into a maximum of (20/0.0229=) 873 partitions.

In this particular example, the end user requires that 40% of the total number of partitions be positive, e.g. (0.4*873=) 349 droplets are positive. Using Poisson statistics, it can be calculated that this requires an average concentration of 446 molecules/20 ul (or 22.3 molecules/ul). Using the reference equation, the Ct value for 446 molecules/20 ul would be 26.06. Assuming the reaction is 100% efficient, the dilution factor is calculated as follows:

$$\text{Dilution Factor} = \text{Efficiency}^{\wedge}(Ct_{target} - Ct)$$
$$= 2^{\wedge}(26.06 - 21)$$
$$= 2^{\wedge}5.06$$
$$= 33.4$$

Alternatively, assuming that the reaction is 100% efficient, the dilution factor can be calculated approximately as 15,199/446=34.08. After digital PCR amplification, this dilution would provide the required ~40% positive droplets (349 positive droplets) and 524 negative droplets.

Knowing the partition volume and the number of positive and negative partitions enables the concentration of the diluted sample to be calculated using Poisson's statistics (Eqns 3-6). Given a partition volume of 0.0229 uL, 873 total partitions comprising 349 positive partitions, and 524 negative partitions, the diluted sample concentration k is calculated to be 22.29 copies/uL.

In a further aspect, the concentration of the diluted sample droplet (as calculated via Poisson's statistics) can be used with the dilution factor data to calculate the concentration of the initial sample. In this instance, the initial sample concentration would be calculated as 22.29*33.4=744 copies/uL, or 14,890 copies/20 uL.

Example 6: Calculating a Standard Curve without Standards

In some embodiments, there might not be a reference equation stored on or otherwise accessible by the system for the automatic determination of a copy number from a measured Ct value. Under such circumstances, assuming that an approximate Ct value for single copy turn on is known, a reference equation can be calculated.

The steps involve performing at least two, and preferably at least three, 10-fold dilutions of the initial sample, and amplifying the droplets until the Ct value for each droplet is determined. Provided that the Ct value for a single copy droplet is known, then a reference equation can be calculated by fitting a line to a plot of Ct value against the log of DNA concentration. For example, a probe based assay might have a single copy turn on expected at cycle 27.5. The resulting reference equation can then be used to determine the initial concentration of the sample, and hence the dilution factor as per previous examples. In yet further embodiments, the efficiency of the reaction can be included or determined, and the standard curve equation modified accordingly.

Example 7: Minimizing the Number of Partitions Required for Quantification Using Digital PCR In some embodiments, a sample might be accurately quantified by processing a 20 uL into 873 partitions, each 0.0229 uL in volume. However, it may also be feasible to accurately quantify the sample using a much smaller volume, for example only 2-3 uL.

Table II below shows an example of how a sample with ~10 copies/uL (~0.23 copies per partition) could be quantified using digital PCR processing with different processed sample volumes. Generally, the smaller the total volume processed, the higher the error associated with the calculated sample concentration. However, if a user only requires a sample to be quantified to within a <5% accuracy, then the system can calculate this by processing as little at 3 uL. If 4 uL or more is processed, an error of <2% from the actual concentration can be achieved. This leads to a reduction in the amount of sample volume that has to be processed from a standard 20 uL down to as little as 3 or 4 uL.

TABLE II

| Volume per Sample | No of Partitions (0.0229 uL) | No of Positive Partitions | No of Negative Partitions | Error from Actual (%) |
|---|---|---|---|---|
| 20 | 873 | 178 | 695 | 0.4 |
| 10 | 436 | 89 | 347 | 0.3 |
| 6.67 | 291 | 59 | 232 | 1.0 |
| 5 | 218 | 44 | 174 | 1.6 |
| 4 | 174 | 35 | 139 | 1.9 |
| 3 | 131 | 26 | 105 | 3.4 |

TABLE II-continued

| Volume per Sample | No of Partitions (0.0229 uL) | No of Positive Partitions | No of Negative Partitions | Error from Actual (%) |
|---|---|---|---|---|
| 2 | 87 | 17 | 70 | 5.1 |
| 1 | 43 | 8 | 35 | 10.1 |

Thus, the present invention further enables opportunities to minimize the number of partitions, and hence sample volume, required for quantification, which will help maximize the number of samples that can be quantified on a single device. After calculating the sample concentration, the system can use Poisson statistics to calculate the minimum number of partitions required within a given accuracy (% error from actual), and sample and/or diluted sample volume available for digital PCR processing. It will be understood by one of ordinary skill in the art that the number of sample partitions depends on several factors including, but not limited to, the sample concentration, the number and volume of partitions, the volume of available sample, the volume of available dilutent, the ratio of any rare to abundant alleles, and the like.

Example 8: Multiplexing

Examples 1-7 above are all compatible with multiplexing, whereby different sample and target sequence combinations can be quantified using digital PCR in a single cartridge. Following on from previous examples, two 10 uL sample/target combinations may be processed rather than a single 20 uL sample. The two or more sample/target sequence combinations may be (a) the same sample but different target sequences, (b) different samples and the same target sequence, (c) different samples and different target sequences, or (d) multiple repeats of the same sample/target sequence combination. It will be further be understood by one of ordinary skill in the art that, if the maximum capacity of the cartridge is 20 uL, one ×20 uL, two ×10 uL, three ×6.67 uL, four ×5 uL, five ×4 uL, and so forth, sample/target sequence combinations may be processed in parallel.

Table III below shows an example of how a sample with ~10 copies/uL (~0.23 copies per partition) could be quantified against up to 5 different target sequences using digital PCR each with <2% error from the actual concentration.

TABLE III

| No of sample/target sequence combinations | Volume per Sample | No of Partitions (0.0229 uL) | No of Positive Partitions | No of Negative Partitions | Error from Actual (%) |
|---|---|---|---|---|---|
| 1 | 20 | 873 | 178 | 695 | 0.4 |
| 2 | 10 | 436 | 89 | 347 | 0.3 |
| 3 | 6.67 | 291 | 59 | 232 | 1.0 |
| 4 | 5 | 218 | 44 | 174 | 1.6 |
| 5 | 4 | 174 | 35 | 139 | 1.9 |

Example 9: Melt Analysis

Examples 1-8 are all fully compatible with a melt analysis after the digital PCR quantification step. In certain preferred embodiments, a melt curve and/or a high resolution melt curve may be achieved by gradually cooling all the thermal control elements from 95° C. down to 60° C. in <1° C. steps, preferably <0.5° C. steps and more preferably in <0.1° C.

steps. The fingerprint obtained from the melt profile provides further information on the content of each amplified droplet, which is particularly useful where rare alleles are being identified, or a sample is being run against multiple different target sequences.

Example 10: Set Baseline and Calculate Threshold

The threshold for automatically determining the Ct value of the amplified products can be calculated either by:
- Using a control droplet, e.g. a droplet containing all the reagents required for PCR but without the nucleic acid sample. The fluorescence of the control droplet should not change as a function of amplification. The threshold is normally set at 10 times the standard deviation of the baseline fluorescence, in this case the fluorescence of the control droplet.
- For droplets containing nucleic acid samples that are not highly concentrated, e.g. Ct value is >15, the baseline can be taken to be between, typically, cycles 1 and 12, where there is little variation in the fluorescence intensity. The threshold is set at a suitable multiple, e.g. ×10, of the standard deviation of the fluorescence values between these cycles.
- For droplets containing a passive reference dye, the threshold can be set as a suitable multiple of the standard deviation of the passive reference dye fluorescence.

It will be understood by one of ordinary skill in the art that the baseline does not have to be 10 times the standard deviation of the baseline and can be modified accordingly to take into account factors such as the readout dye used, background fluorescence, uniformity of optical illumination and so forth. When control droplet(s) are used to determine the baseline and threshold values, the control droplet(s) will follow the same PCR preparation and PCR thermal cycling as the sample droplet(s) and be moved to waste at the appropriate point in the workflow.

Example 11: Normalizing to a Reference Control

FIGS. 21A-21G are drawings depicting a progression of steps constituting another exemplary method of performing a digital PCR reaction protocol in accordance with embodiments of the present invention, including the use of internal reference target sequences for more accurate determinations. Internal reference or "housekeeping" target sequences may be used to more accurately determine the initial sample concentration and/or efficiency of the reaction being analyzed. These reference target sequences can be used for sample specific normalization, with the normalization process controlling for outliers and compensating, for example, for differences in expression levels between the reference target sequences. The most common normalization techniques are the "double delta Ct", also known as the "ΔΔCt" method, or the "Pffafl" method, both of which are well known to one skilled in the art and are governed by the following equations.

$$\Delta\Delta Ct = \Delta Ct_{(target\ sample)} - (Ct_{(reference\ sample)})$$

$$\Delta\Delta Ct = (Ct_{(target\ gene, target\ sample)} - Ct_{(reference\ gene, target\ sample)}) - (Ct_{(target\ gene, reference\ sample)} - Ct_{(reference\ gene, reference\ sample)})$$

where:

$Ct_{(target\ gene,\ target\ sample)}$=Ct value of target gene in a target sample;

$Ct_{(reference\ gene,\ target\ sample)}$=Ct value of reference gene in a target sample;

$Ct_{(target\ gene,\ reference\ sample)}$=Ct value of target gene in a reference sample; and $Ct_{(reference\ gene,\ reference\ sample)}$=Ct value of reference gene in a reference sample.

In some instances, the ΔΔCt method can be used to validate the accuracy of sample dilutions on an EWOD device. Preferably, probes will be used as the readout mechanism.

Figure 21A:
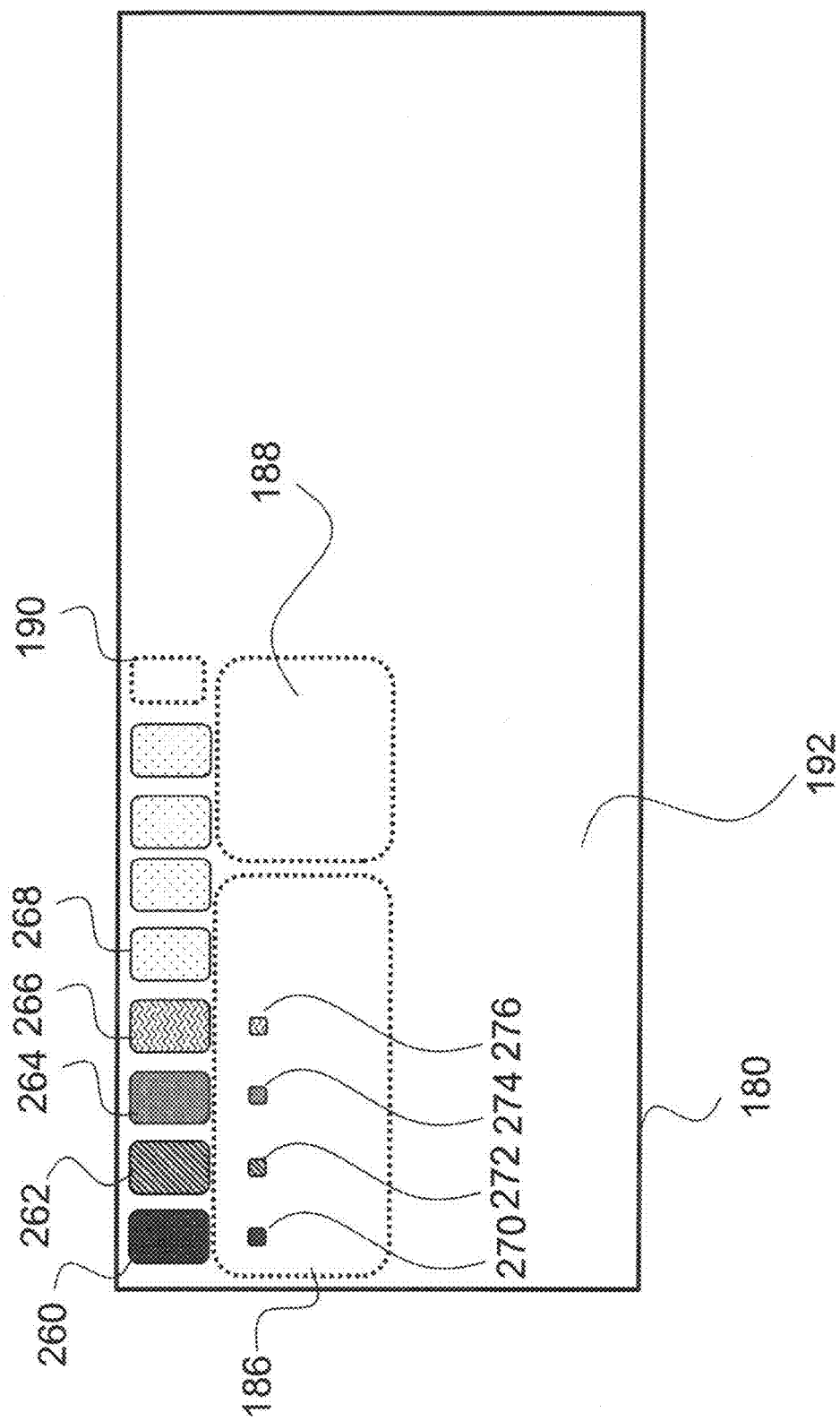
Figure 21B:
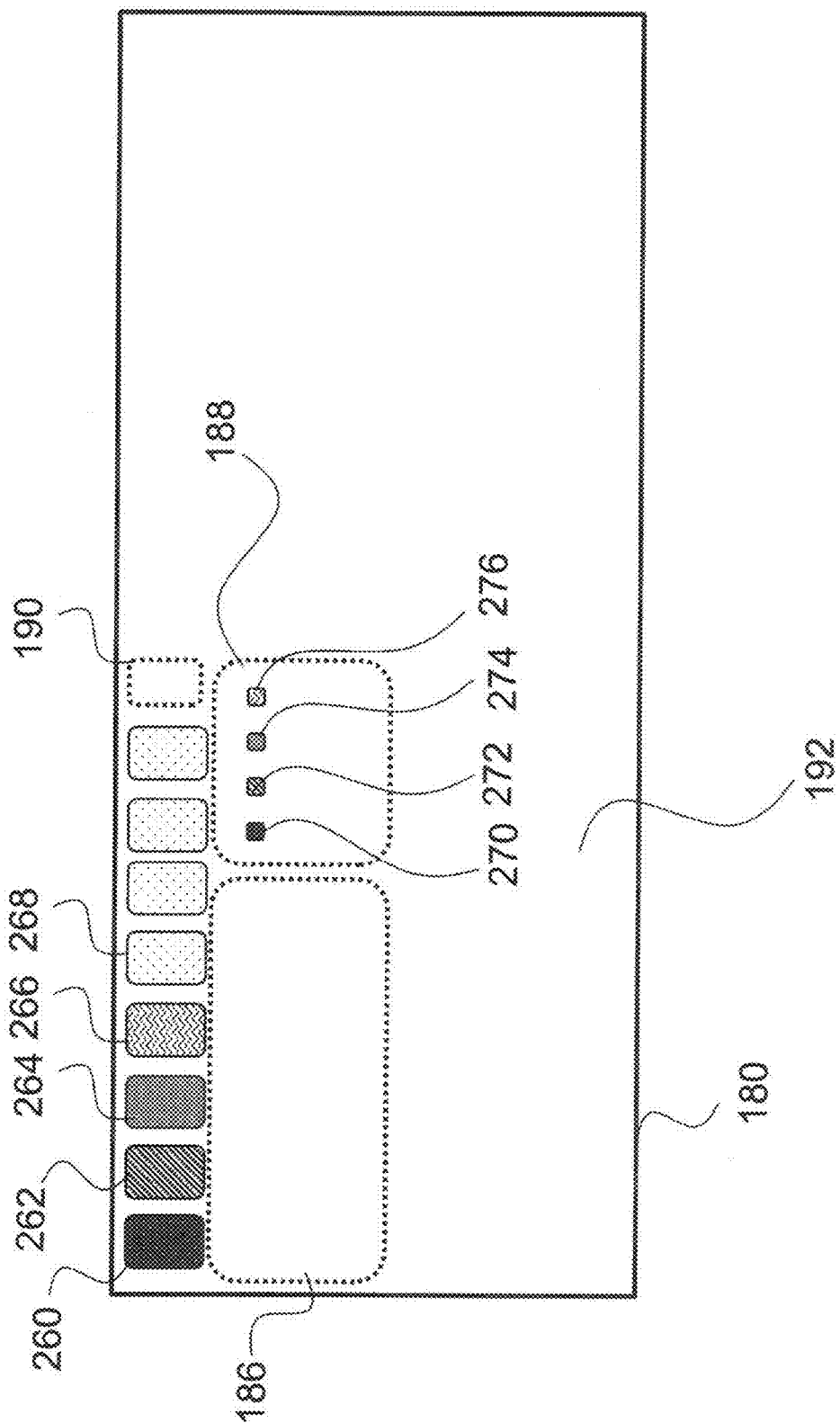
Figure 21C:
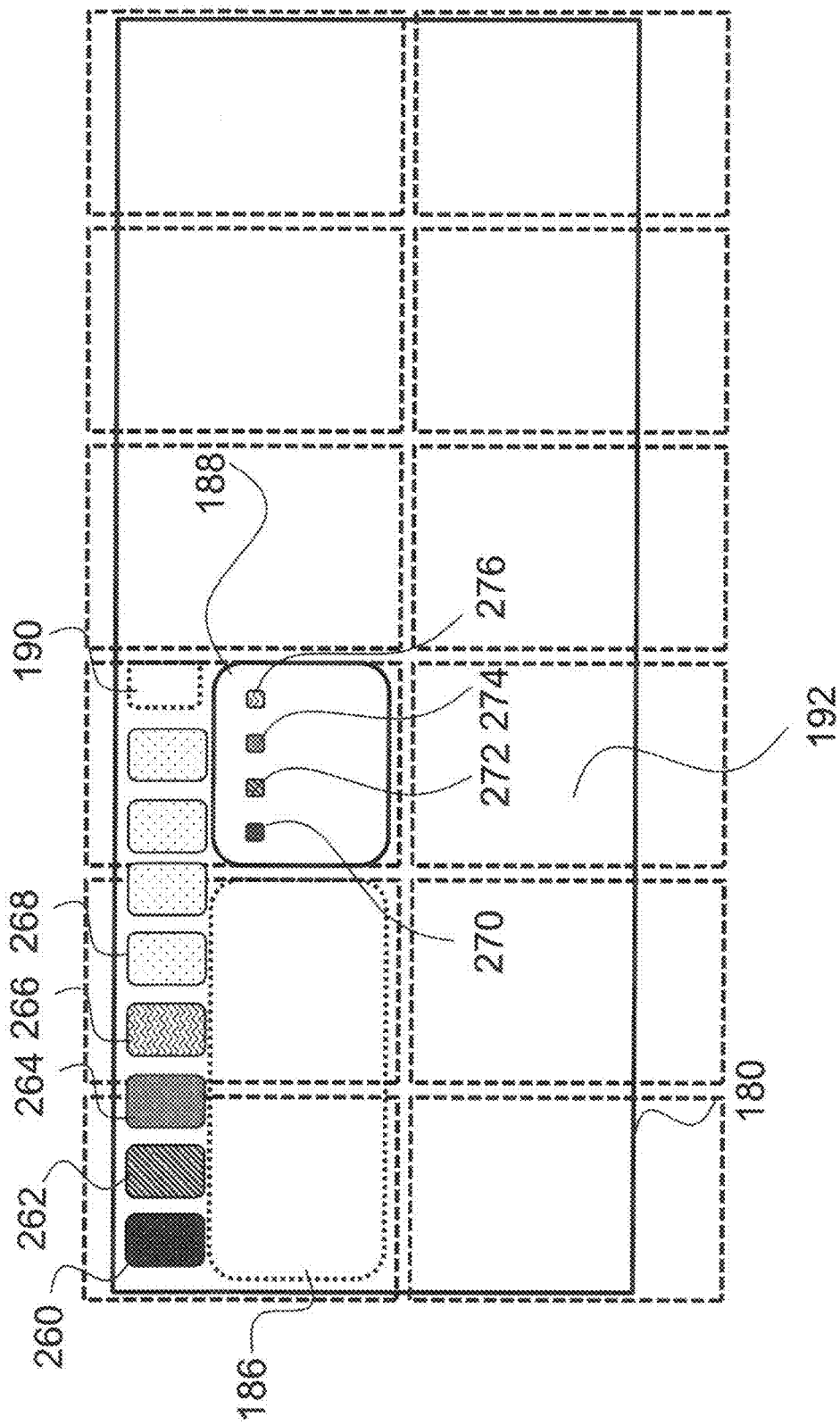

FIG. 21A depicts the EWOD cartridge 180 into which there are inputted a (target gene, target sample) volume 260, a (reference gene, target sample) volume 262, a (target gene, reference sample) volume 264, a (reference gene, reference sample) volume 266, and four diluent volumes 268. A droplet from each of the (target gene, target sample) volume 260, (reference gene, target sample) volume 262, (target gene, reference sample) volume 264, and (reference gene, reference sample) volume 266 is dispensed via electrowetting forces into the sample preparation zone 186. Each volume contains the necessary reagents for performing PCR amplification. The dispensed droplets respectively are identified by reference numerals 270, 272, 274, and 276. As shown in FIG. 21B, such droplets are moved into the first amplification zone 188. As shown in FIG. 21C, similarly as in previous embodiments, the first amplification zone 188 is located in correspondence with the third thermal control element 196-3, and such thermal control element is used to thermally cycle the sample and reference droplet between 95° C. and 60° C. to perform PCR, FIG. 12C. After the PCR amplification, these droplets are moved by electrowetting forces to the waste zone 190 (see FIG. 21E).

Figure 21D:
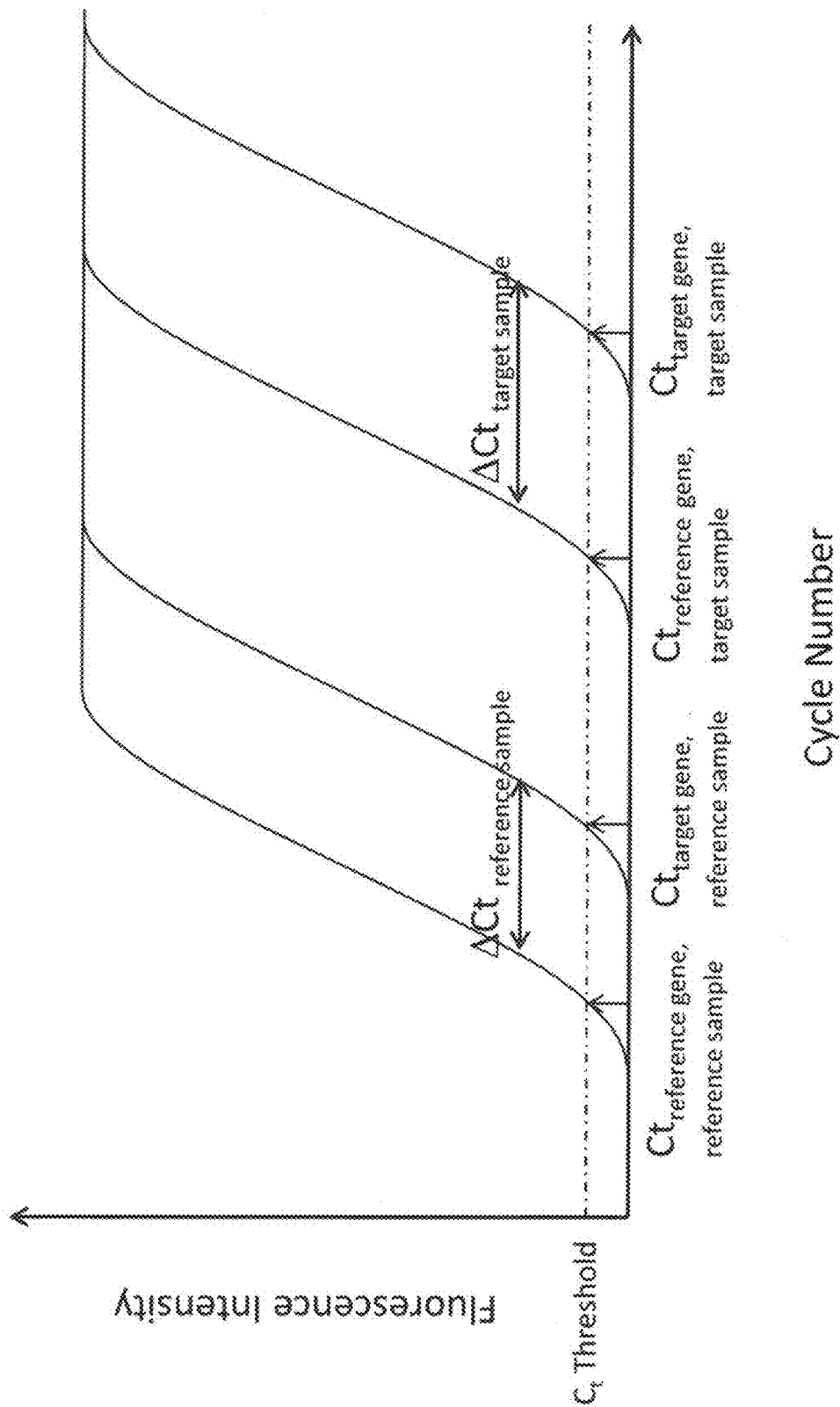

FIG. 21D is a graph depicting an example of a fluorescence intensity curve that illustrates representative calculations associated with this example. A fluorescence image is taken each cycle during the 60° C. anneal/extension step until both $\Delta Ct_{-target\ sample}$ and $\Delta Ct_{-reference\ sample}$ can be established, as shown in FIG. 21D. The individual Ct values can be used to calculate a dilution factor so that each of the four gene/sample inputs can be quantified using digital nucleic acid amplification techniques. The diluent volumes 268 contain all the reagents necessary for PCR amplification.

Figure 21E:
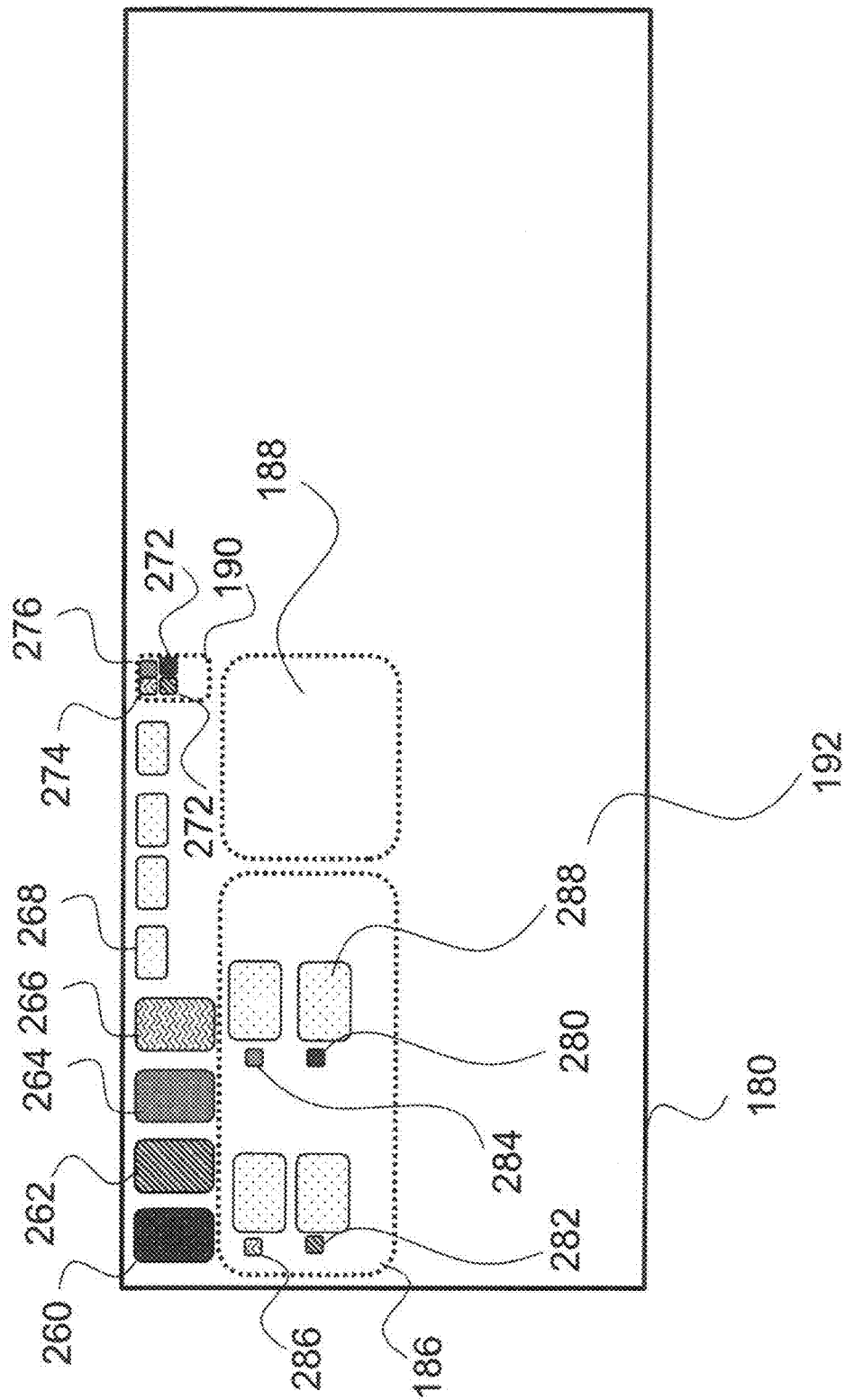
Figure 21G:
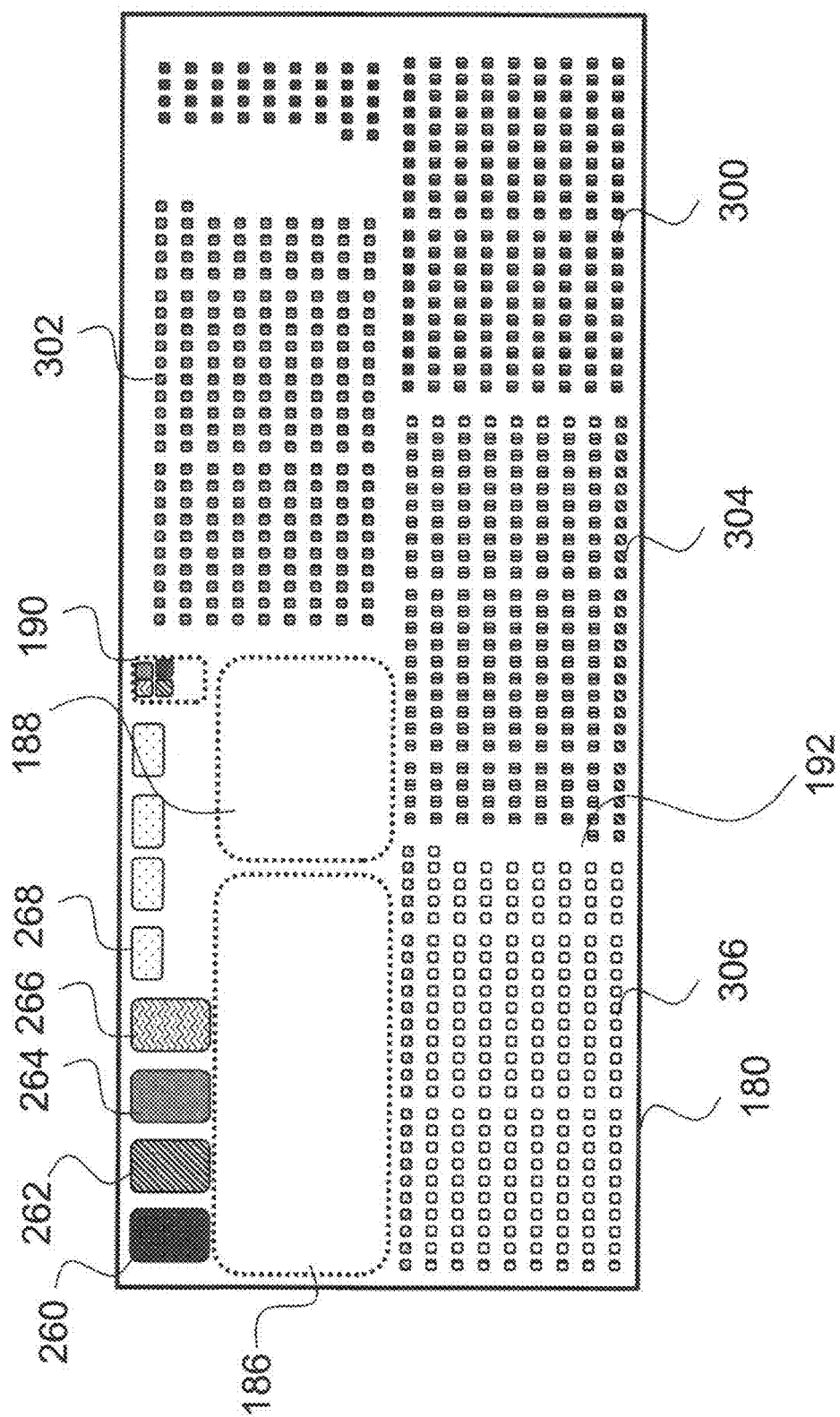

Referring to FIG. 21E, second sample droplets are dispensed into the sample preparation zone 186 from the original volumes, which are identified in FIG. 20E respectively as sample droplets 280, 282, 284, and 286, along with the appropriate diluent droplets 288 from the diluent volumes 268. As shown in FIG. 21F, the sample droplets each are mixed and merged with the respective diluent droplets to form respective four gene/sample combinations 290, 292, 294, and 296. As shown in FIG. 21G, each of the four gene/sample combinations is partitioned and moved by electrowetting into the digital amplification zone 192 into respective partition zones 300, 302, 304, and 306. A digital amplification process, such as digital PCR, is performed, and the system automatically determines which partitions are positive and negative for each of the four gene/sample combinations and quantifies each concentration using Poisson statistics similarly as in the previous embodiments.

Example 12: RT-PCR

The embodiments and examples of the present invention may be employed for reverse-transcription qPCR and digital PCR assays. In these examples, the starting sample is an RNA sample. Complementary DNA is prepared from RNA using a reverse-transcription (RT) step. This is then followed by PCR. Reagents for RT and PCR may be mixed as in a 1-step RT-PCR protocol, or added in two steps. The two-step protocol adds the RT reagents and performs reverse-transcription before adding the PCR reagents for amplification. Methods for sample dilution, sample partitioning, normalizing, and multiplexing broadly remain the same as described previously in Examples 1-11 and the various embodiments of FIGS. 14-21.

Example 13: Isothermal Amplification

The embodiments and examples of the present invention are compatible with isothermal amplification techniques. For applications using isothermal amplification, the thermal control elements in the system can be programmed to heat the sample partitions to the fixed temperature required for isothermal amplification at the correct point in the workflow. Isothermal reactions are typically performed at between 37-70° C. depending on the type of isothermal amplification process being used.

In isothermal methods, the fluorescence intensity of the reaction is monitored with respect to time rather than "per cycle" as is done in PCR. The time at which the sample fluorescence is greater than a given threshold is called the "time to positive" or Tp value. Samples of different concentrations produce different Tp values. Using standards, e.g. samples of known concentration, Tp values can be established for a range of sample concentrations. A correlation between "Tp" and "sample concentration" can then be determined in a way analogous to "Ct" against "sample concentration" in qPCR.

The relationship between Tp and sample concentration will be stored internally within the system for a given reaction so that an optimal dilution factor can be calculated. Additionally and/or alternatively, the optimized Tp value for digital nucleic acid quantification will be stored on the system computer of the present invention for a given reaction to calculate required dilution factors.

For example, a ~1 uL of a DNA sample of an unknown concentration is loaded onto an EWOD device. A 2×2 droplet, 0.0229 uL, is split from the sample using electrowetting and transferred to the first amplification zone. The fluorescence of the droplet is measured as a function of time and analyzed by the control system. When the intensity of the fluorescence signal amplifies above the threshold value, the Tp value for the sample is calculated automatically. The Tp value for the sample of unknown concentration is compared to either the optimal Tp value, and/or the reference equation for the reaction, stored in the systems' computer. The data is then used to calculate the dilution factor for the sample to be quantified using digital nucleic acid amplification techniques.

In one example, for a given reaction, the Tp value of the unknown starting sample is measured to be 11 mins. For said given reaction, the system database has a reference equation of:

$$Y=-2.5x+22.5$$

where y is the Tp value (mins) and x is the log of DNA concentration (copies/20 ul).

For a sample with a measured Tp of 11 mins, the concentration can be calculated to be ~39,811 copies/20 ul, or ~1,991 copies/ul. For optimal digital nucleic acid amplification, the target concentration is ~0.7-1.6 copies/partition. Given that, for a particular configuration, the system will partition 20 uL of the final sample volume into 873×0.0229 uL partitions, and assuming that the target optimal concentration for digital PCR is set to ~1 copy per partition, the system can calculate that the optimal sample concentration is approximately 873 copies in the 20 uL that will be analyzed. The dilution factor can be calculated as follows:

$$\text{Dilution Factor} = 39,811/873$$
$$= 45.6$$

Example 14: Sorting, Pooling and Extracting of Amplified Samples

In the embodiments and examples of the present invention, amplified partitions can be identified as being either positive or negative. The system can then sort the droplets and pool them into "positive" and "negative" volumes, moving the partitions and merging them by electrowetting as required. The pooled volumes can then be extracted through extract ports for further downstream analysis.

In this example, it is optional whether Poisson statistics are used to quantify the concentration of the sample; in some circumstances it is sufficient simply to identify which partitions are positive and which are negative.

An aspect of the invention, therefore, is an enhanced electrowetting on dielectric (EWOD) device and a related method of performing a digital assay amplification technique in an EWOD device. In exemplary embodiments, the method of performing a digital quantification of a species in an electrowetting on dielectric (EWOD) device includes the steps of: inputting a sample volume into the EWOD device; inputting a diluent volume into the EWOD device; performing an electrowetting operation to generate a first sample droplet from the sample volume; performing an amplification process on the first sample droplet within the EWOD device; measuring a turn-on value for the sample droplet; comparing the measured turn-on value of the sample droplet to a target turn-on value for digital quantification; calculating a dilution factor based on the comparison of the measured turn-on value of the sample droplet to the target turn-on value; performing an electrowetting operation to extract a second sample droplet from the sample volume; performing an electrowetting operation to dilute the second sample droplet with the diluent volume in accordance with the dilution factor to form a diluted second sample droplet; and performing a digital quantification on the diluted second sample droplet to quantify an initial concentration of the species in the sample volume. The method may include one or more of the following features, either individually or in combination.

In an exemplary embodiment of the method, the first sample droplet is moved by electrowetting forces into a sample preparation zone, and further is moved by electrowetting forces into a first amplification zone in which the amplification of the species of interest on the first sample droplet is performed, and the first amplification zone is separate from the sample preparation zone.

In an exemplary embodiment of the method, the method further includes using electrowetting forces to dilute the first sample droplet with a portion of the diluent volume when the first sample droplet is in the sample preparation zone to form an initial diluted sample droplet, and moving the initial diluted sample droplet into the first amplification zone to perform amplification on the initial diluted sample droplet.

In an exemplary embodiment of the method, performing the digital amplification comprises using electrowetting forces to split the diluted second droplet into partitions that are moved into a digital amplification zone that is separate from the sample preparation zone and the first amplification zone.

In an exemplary embodiment of the method, the EWOD device includes a fluorescence measurement apparatus, and the turn-on value of the sample droplet is determined using a fluorescence intensity curve.

In an exemplary embodiment of the method, performing the digital amplification includes performing a normalization process by detecting fluorescence relative to fluorescence of a reference dye contained in the sample volume.

In an exemplary embodiment of the method, performing the digital amplification includes: partitioning the diluted sample droplet into a plurality of partitions; performing an amplification process on the plurality of partitions; counting a number of positive partitions and a number of negative partitions; and using Poisson statistics to quantify an initial concentration of the species in the sample volume.

In an exemplary embodiment of the method, the method further includes adding a scaling factor to ensure a proportion of positive partitions is between 0.01%-90%.

In an exemplary embodiment of the method, the method further includes determining an efficiency of reaction of the amplification process of the first sample droplet to calculate the dilution factor.

In an exemplary embodiment of the method, determining the efficiency of reaction comprises the steps of: performing an electrowetting operation to extract another sample droplet from the sample volume; performing amplification on the another sample droplet within the EWOD device; measuring a second turn-on value for the another sample droplet; determining an efficiency of reaction using the turn-on value and the second turn-on value; and calculating the dilution factor using the efficiency of reaction applied to the comparison of the measured turn-on value of the sample droplet to the target turn-on value.

In an exemplary embodiment of the method, the method further includes inputting a plurality of target input volumes into the EWOD device having respective primers corresponding to a plurality of respective targets in the sample volume; performing an electrowetting operation to extract a respective daughter sample droplet from the sample volume corresponding to each of the plurality of target input volumes; performing an electrowetting operation to dilute the daughter droplets with the respective target input volumes in accordance with the dilution factor to form a plurality of respective diluted sample/target volume combinations; and performing the amplification process on the diluted sample/target volume combinations to quantify an initial concentration of the respective targets on the species in the sample volume.

In an exemplary embodiment of the method, the method further includes inputting a quantification volume into the EWOD device; dispensing the first sample droplet and a quantification droplet from the quantification volume into a zone of the EWOD device and mix said droplets together to form an amplifying droplet; performing the amplification process on the amplifying droplet; measuring a turn-on value for the amplifying droplet; comparing the measured turn-on value of the amplifying droplet to the target turn-on value; and calculating the dilution factor based on the comparison of the measured turn-on value of the amplifying droplet to the target turn-on value.

In an exemplary embodiment of the method, the sample volume contains a nucleic acid species, the EWOD device includes a plurality of thermal control elements, and the amplification process performed on the first sample droplet and/or the digital amplification is a polymerase chain reaction (PCR) nucleic acid amplification.

In an exemplary embodiment of the method, the turn-on value is a threshold cycle value (Ct) for the sample droplet.

In an exemplary embodiment of the method, the sample volume contains a nucleic acid species, and the nucleic acid amplification performed on the first sample droplet and/or the digital nucleic acid amplification is an isothermal nucleic acid amplification.

In an exemplary embodiment of the method, the turn-on value is a time to positive value (Tp) for the sample droplet.

In an exemplary embodiment of the method, the sample volume contains a protein species.

In an exemplary embodiment of the method, the sample volume contains a cell species.

In an exemplary embodiment of the method, the sample volume comprises a plurality of sample volumes inputted into the EWOD device including a (target gene, target sample) volume, a (reference gene, target sample) volume, a (target gene, reference sample) volume, and a (reference gene, reference sample) volume, the method further comprising: performing an electrowetting operation to extract a respective daughter sample droplet from each of the plurality of sample input volumes; performing nucleic acid amplification on the daughter sample droplets within the EWOD device; measuring a $\Delta Ct_{\text{-target sample}}$ and a $\Delta Ct_{\text{-reference sample}}$ for the daughter sample droplets; and calculating the dilution factor based on the measured $\Delta Ct_{\text{-target sample}}$ and $\Delta Ct_{\text{-reference sample}}$. (FIG. 21 series, claims 15-16)

In an exemplary embodiment of the method, the method further includes performing an electrowetting operation to extract a second respective daughter sample droplet from each of the plurality of sample volumes; performing an electrowetting operation to dilute the second daughter droplets with the diluent volume in accordance with the dilution factor to form a plurality of respective gene/sample combinations; and performing the digital nucleic acid amplification on the gene/sample combinations to quantify an initial concentration of the respective gene/sample combinations in the plurality of sample volumes.

Another aspect of the invention is a microfluidic system including an electro-wetting on dielectric (EWOD) device comprising an element array configured to receive one or more liquid droplets, the element array comprising a plurality of individual array elements; and a control system configured to control actuation voltages applied to the element array to perform manipulation operations as to the liquid droplets to perform the method of digital quantification of a species according to any of the embodiments. The system further may include a plurality of thermal control elements located at different spatial locations along the EWOD device, at least one of the thermal control elements being variable in temperature with respect to time; wherein the control system includes a thermal control unit configured to control temperatures of the plurality of thermal control elements to generate a plurality of thermal zones located at different spatial locations along the EWOD device.

In an exemplary embodiment of the microfluidic system, the control system controls the actuation voltages applied to the element array to form separate zones includes a sample preparation zone to prepare the first sample droplet, a first amplification zone in which the amplification process on the first sample droplet is performed, and a digital amplification zone in which the amplification process is performed; wherein the sample preparation zone, the first amplification zone, and the digital amplification zone spatially correspond to different thermal control elements.

Another aspect of the invention is a non-transitory computer-readable medium storing program code which is executed by a processing device for controlling actuation voltages applied to array elements of an element array of an electro-wetting on dielectric (EWOD) device for performing droplet manipulations on droplets on the element array, the program code being executable by the processing device to perform the steps of the method of performing a digital amplification technique in an EWOD device according to any of the embodiments.

Although the invention has been shown and described with respect to a certain embodiment or embodiments, equivalent alterations and modifications may occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or embodiments of the invention. In addition, while a particular feature of the invention may have been described above with respect to only one or more of several embodiments, such feature may be combined with one or more other features of the other embodiments, as may be desired and advantageous for any given or particular application.

INDUSTRIAL APPLICABILITY

The described embodiments could be used to provide enhanced AM-EWOD device and EWOD device operation. The EWOD device can be employed to provide enhanced nucleic acid amplification techniques for increasing the dynamic range of sample concentrations that can be quantified using digital nucleic acid amplification techniques, such as for example digital PCR and isothermal amplification techniques, on an EWOD device, and may be applied in connection with either DNA or RNA amplification techniques. The AM-EWOD or EWOD device could form a part of a lab-on-a-chip system. Such devices could be used in manipulating, reacting and sensing chemical, biochemical or physiological materials.

What is claimed is:

1. A method of performing a digital quantification of a species in an electrowetting on dielectric (EWOD) device comprising the steps of:
    inputting a sample volume into the EWOD device;
    inputting a diluent volume into the EWOD device;
    performing an electrowetting operation to generate a first sample droplet from the sample volume;
    performing an amplification process on the first sample droplet within the EWOD device;
    measuring a turn-on value for the sample droplet, wherein the turn-on value comprises a point at which fluorescence crosses above a threshold value relative to a baseline fluorescence;
    comparing the measured turn-on value of the sample droplet to a target turn-on value for digital quantification;
    calculating a dilution factor based on the comparison of the measured turn-on value of the sample droplet to the target turn-on value;
    performing an electrowetting operation to extract a second sample droplet from the sample volume;
    performing an electrowetting operation to dilute the second sample droplet with the diluent volume in accordance with the dilution factor to form a diluted second sample droplet;
    performing a digital quantification on the diluted second sample droplet to quantify an initial concentration of the species in the sample volume; and
    determining an efficiency of reaction of the amplification process of the first sample droplet to calculate the dilution factor.

2. The method of claim 1, wherein the first sample droplet is moved by electrowetting forces into a sample preparation zone, and further is moved by electrowetting forces into a first amplification zone in which the amplification of the species of interest on the first sample droplet is performed, and the first amplification zone is separate from the sample preparation zone.

3. The method of claim 2, further comprising using electrowetting forces to dilute the first sample droplet with a portion of the diluent volume when the first sample droplet is in the sample preparation zone to form an initial diluted sample droplet, and moving the initial diluted sample droplet into the first amplification zone to perform amplification on the initial diluted sample droplet.

4. The method of claim 3, wherein performing the digital amplification comprises using electrowetting forces to split the diluted second droplet into partitions that are moved into a digital amplification zone that is separate from the sample preparation zone and the first amplification zone.

5. The method of claim 1, wherein the EWOD device includes a fluorescence measurement apparatus, and the turn-on value of the sample droplet is determined using a fluorescence intensity curve.

6. The method of claim 1, wherein performing the digital quantification includes performing a normalization process by detecting fluorescence relative to fluorescence of a reference dye contained in the sample volume.

7. The method of claim 1, wherein performing the digital quantification includes:
    partitioning the diluted sample droplet into a plurality of partitions;
    performing an amplification process on the plurality of partitions;
    counting a number of positive partitions and a number of negative partitions; and
    using Poisson statistics to quantify an initial concentration of the species in the sample volume.

8. The method of claim 7, further comprising adding a scaling factor to ensure a proportion of positive partitions is between 0.01%-90%.

9. The method of claim 1, wherein determining the efficiency of reaction comprises the steps of:
    performing an electrowetting operation to extract another sample droplet from the sample volume;
    performing amplification on the another sample droplet within the EWOD device;
    measuring a second turn-on value for the another sample droplet;
    determining an efficiency of reaction using the turn-on value and the second turn-on value; and calculating the dilution factor using the efficiency of reaction applied to the comparison of the measured turn-on value of the sample droplet to the target turn-on value.

10. The method of claim 1, further comprising:
inputting a plurality of target input volumes into the EWOD device having respective primers corresponding to a plurality of respective targets in the sample volume;
performing an electrowetting operation to extract a respective daughter sample droplet from the sample volume corresponding to each of the plurality of target input volumes;
performing an electrowetting operation to dilute the daughter droplets with the respective target input volumes in accordance with the dilution factor to form a plurality of respective diluted sample/target volume combinations; and
performing the amplification process on the diluted sample/target volume combinations to quantify an initial concentration of the respective targets on the species in the sample volume.

11. The method of claim 10, further comprising:
inputting a quantification volume into the EWOD device;
dispensing the first sample droplet and a quantification droplet from the quantification volume into a zone of the EWOD device and mix said droplets together to form an amplifying droplet;
performing the amplification process on the amplifying droplet;
measuring a turn-on value for the amplifying droplet;
comparing the measured turn-on value of the amplifying droplet to the target turn-on value; and
calculating the dilution factor based on the comparison of the measured turn-on value of the amplifying droplet to the target turn-on value.

12. The method of claim 1, wherein the sample volume contains a protein species.

13. The method of claim 1, wherein the sample volume contains a cell species.

14. A method of performing a digital quantification of a species in an electrowetting on dielectric (EWOD) device comprising the steps of:
inputting a sample volume into the EWOD device;
inputting a diluent volume into the EWOD device;
performing an electrowetting operation to generate a first sample droplet from the sample volume;
performing an amplification process on the first sample droplet within the EWOD device;
measuring a turn-on value for the sample droplet;
comparing the measured turn-on value of the sample droplet to a target turn-on value for digital quantification;
calculating a dilution factor based on the comparison of the measured turn-on value of the sample droplet to the target turn-on value;
performing an electrowetting operation to extract a second sample droplet from the sample volume;
performing an electrowetting operation to dilute the second sample droplet with the diluent volume in accordance with the dilution factor to form a diluted second sample droplet; and
performing a digital quantification on the diluted second sample droplet to quantify an initial concentration of the species in the sample volume
wherein the sample volume contains a nucleic acid species, the EWOD device includes a plurality of thermal control elements, and the amplification process performed on the first sample droplet and/or the digital amplification is a polymerase chain reaction (PCR) nucleic acid amplification; and
wherein the turn-on value is a threshold cycle value (Ct) for the sample droplet.

15. A method of performing a digital quantification of a species in an electrowetting on dielectric (EWOD) device comprising the steps of:
inputting a sample volume into the EWOD device;
inputting a diluent volume into the EWOD device;
performing an electrowetting operation to generate a first sample droplet from the sample volume;
performing an amplification process on the first sample droplet within the EWOD device;
measuring a turn-on value for the sample droplet;
comparing the measured turn-on value of the sample droplet to a target turn-on value for digital quantification;
calculating a dilution factor based on the comparison of the measured turn-on value of the sample droplet to the target turn-on value;
performing an electrowetting operation to extract a second sample droplet from the sample volume;
performing an electrowetting operation to dilute the second sample droplet with the diluent volume in accordance with the dilution factor to form a diluted second sample droplet; and
performing a digital quantification on the diluted second sample droplet to quantify an initial concentration of the species in the sample volume;
wherein the sample volume contains a nucleic acid species, and the nucleic acid amplification performed on the first sample droplet and/or the digital nucleic acid amplification is an isothermal nucleic acid amplification; and
wherein the turn-on value is a time to positive value (Tp) for the sample droplet.

16. A method of performing a digital quantification of a species in an electrowetting on dielectric (EWOD) device comprising the steps of:
inputting a sample volume into the EWOD device;
inputting a diluent volume into the EWOD device;
performing an electrowetting operation to generate a first sample droplet from the sample volume;
performing an amplification process on the first sample droplet within the EWOD device;
measuring a turn-on value for the sample droplet, wherein the turn-on value comprises a point at which fluorescence crosses above a threshold value relative to a baseline fluorescence;
comparing the measured turn-on value of the sample droplet to a target turn-on value for digital quantification;
calculating a dilution factor based on the comparison of the measured turn-on value of the sample droplet to the target turn-on value;
performing an electrowetting operation to extract a second sample droplet from the sample volume;
performing an electrowetting operation to dilute the second sample droplet with the diluent volume in accordance with the dilution factor to form a diluted second sample droplet; and
performing a digital quantification on the diluted second sample droplet to quantify an initial concentration of the species in the sample volume;
wherein:
the sample volume comprises a plurality of sample volumes inputted into the EWOD device including a (target gene, target sample) volume, a (reference gene, target sample) volume, a (target gene, reference sample) volume, and a (reference gene, reference sample) volume, the method further comprising:

performing an electrowetting operation to extract a respective daughter sample droplet from each of the plurality of sample input volumes;

performing nucleic acid amplification on the daughter sample droplets within the EWOD device;

measuring a $\Delta Ct_{\text{-target sample}}$ and a $\Delta Ct_{\text{-reference sample}}$ for the daughter sample droplets; and calculating the dilution factor based on the measured $\Delta Ct_{\text{-target sample}}$ and $\Delta Ct_{\text{-reference sample}}$.

17. The method of claim 16, further comprising:

performing an electrowetting operation to extract a second respective daughter sample droplet from each of the plurality of sample volumes;

performing an electrowetting operation to dilute the second daughter droplets with the diluent volume in accordance with the dilution factor to form a plurality of respective gene/sample combinations; and performing the digital quantification on the gene/sample combinations to quantify an initial concentration of the respective gene/sample combinations in the plurality of sample volumes.

* * * * *